United States Patent
Wu et al.

(10) Patent No.: US 9,586,939 B2
(45) Date of Patent: Mar. 7, 2017

(54) QUINAZOLINE DERIVATIVE AS TYROSINE-KINASE INHIBITOR, PREPARATION METHOD THEREFOR AND APPLICATION THEREOF

(75) Inventors: Frank Wu, Jinan (CN); Aichen Wang, Jinan (CN)

(73) Assignee: XUANZHU PHARMA CO., LTD., Jinan (CN)

( * ) Notice: Subject to any disclaimer, the term of this patent is extended or adjusted under 35 U.S.C. 154(b) by 350 days.

(21) Appl. No.: 14/119,945

(22) PCT Filed: May 28, 2012

(86) PCT No.: PCT/CN2012/000737
§ 371 (c)(1),
(2), (4) Date: Nov. 25, 2013

(87) PCT Pub. No.: WO2012/159457
PCT Pub. Date: Nov. 29, 2012

(65) Prior Publication Data
US 2014/0161801 A1    Jun. 12, 2014

(30) Foreign Application Priority Data
May 26, 2011  (CN) .................... 2011 1 0138115

(51) Int. Cl.
| | |
|---|---|
| *C07D 403/12* | (2006.01) |
| *C07D 401/14* | (2006.01) |
| *C07D 405/14* | (2006.01) |
| *C07D 403/14* | (2006.01) |
| *C07D 239/94* | (2006.01) |
| *C07D 451/02* | (2006.01) |
| *C07D 453/02* | (2006.01) |
| *C07D 471/08* | (2006.01) |
| *C07D 487/08* | (2006.01) |
| *C07D 491/107* | (2006.01) |
| *C07D 493/08* | (2006.01) |
| *C07D 498/08* | (2006.01) |
| *A61K 31/517* | (2006.01) |
| *A61K 31/5377* | (2006.01) |

(Continued)

(52) U.S. Cl.
CPC .......... *C07D 403/12* (2013.01); *A61K 31/517* (2013.01); *A61K 31/5377* (2013.01); *A61K 45/06* (2013.01); *C07D 239/94* (2013.01); *C07D 401/14* (2013.01); *C07D 403/14* (2013.01); *C07D 405/14* (2013.01); *C07D 451/02* (2013.01); *C07D 453/02* (2013.01); *C07D 471/08* (2013.01); *C07D 487/08* (2013.01); *C07D 491/107* (2013.01); *C07D 493/08* (2013.01); *C07D 498/08* (2013.01)

(58) Field of Classification Search
CPC .................................................. A61K 31/517
See application file for complete search history.

(56) References Cited

U.S. PATENT DOCUMENTS

| | | | |
|---|---|---|---|
| 2009/0306004 A1 | 12/2009 | Etrych et al. | |
| 2009/0306044 A1 | 12/2009 | Solca et al. | |
| 2013/0184297 A1* | 7/2013 | Huang ................ | C07D 403/14 514/266.22 |

FOREIGN PATENT DOCUMENTS

| | | |
|---|---|---|
| CN | 101918390 | 12/2010 |
| CN | 101918390 A | 12/2010 |
| CN | 102382106 | 3/2012 |

(Continued)

OTHER PUBLICATIONS

Pinedo et al. (2000).*
McMahon et al. (2000).*
International Application No. PCT/CN2012/000737, International Search Report mailed Sep. 6, 2012, 9 pages.
Chinese Patent Application No. 201280025324.X , Office Action dated Sep. 5, 2014.
Chen , "Computational Study of the Binding Mode of Epidermal Growth Factor Receptor Kinase Inhibitors", Chemical Biology & Drug Design, vol. 71, No. 5, pp. 434-446, May 2008.

(Continued)

*Primary Examiner* — Paul V Ward
(74) *Attorney, Agent, or Firm* — Kilpatrick Townsend & Stockton LLP

(57) ABSTRACT

The invention relates to a quinazoline derivative represented by the general formula (I), a pharmaceutical acceptable salt and a stereoisomer thereof as tyrosine kinase inhibitor, wherein $R^1$, $R^2$, $R^3$, $R^{3'}$, $R^4$, $R^5$, $R^6$, X, L, T, Z and q are as defined in the specification. The invention also relates to a process for preparing the same, a pharmaceutical composition and a pharmaceutical formulation containing the derivative, use of the derivative for treating excessive proliferative diseases and chronic obstructive pulmonary disease and use of the derivative in the manufacture of a medicament for treating excessive proliferative diseases and chronic obstructive pulmonary disease.

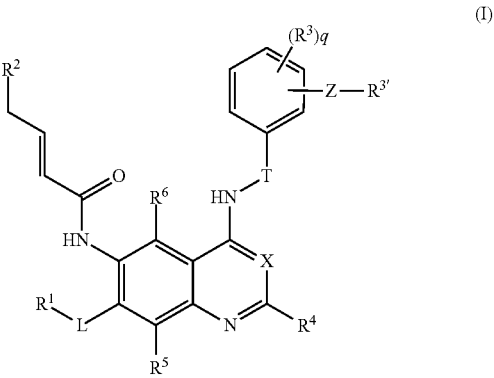

12 Claims, No Drawings

(51) Int. Cl.
  *A61K 45/06* (2006.01)
  *C07D 491/08* (2006.01)

(56) References Cited

FOREIGN PATENT DOCUMENTS

| | | |
|---|---|---|
| CN | 102382106 A | 3/2012 |
| EP | 2612860 | 7/2013 |
| JP | 2002525359 | 8/2002 |
| JP | 2003530395 | 10/2003 |
| JP | 2005526837 | 9/2005 |
| JP | 2013536253 | 9/2013 |
| WO | 0018740 | 4/2000 |
| WO | 0177104 | 10/2001 |
| WO | 03089439 | 10/2003 |
| WO | 2005107758 | 11/2005 |
| WO | 2012159457 | 11/2012 |

OTHER PUBLICATIONS

European Application No. EP12788871.7, European Search Report dated Sep. 29, 2014.
Japanese Application No. JP2014-511709, Office Action dated Dec. 24, 2014.
International Application No. PCT/CN2012/000737, "International Preliminary Report on Patentability", Dec. 5, 2013, 19 pages.
Tsou et al., "Optimization of 6, 7-disubstituted-4-(arylamino) quinoline-3-carbonitriles as orally active, irreversible inhibitors of human epidermal growth factor receptor-2 kinase activity", Journal of medicinal chemistry 48.4 (2005): 1107-1131.

* cited by examiner

QUINAZOLINE DERIVATIVE AS TYROSINE-KINASE INHIBITOR, PREPARATION METHOD THEREFOR AND APPLICATION THEREOF

PRIOR RELATED APPLICATIONS

This application is a National Phase application of International Application No. PCT/CN2012/000737 filed May 28, 2012, which claims priority to Chinese Patent Application No. 201110138115.3 filed May 26, 2011, each of which is incorporated herein by reference in its entirety.

TECHNICAL FIELD

The present invention belongs to the field of pharmaceutical technology, more specifically relates to a quinazoline derivative as tyrosine kinase inhibitor, a pharmaceutically acceptable salt thereof and a stereoisomer thereof, a preparation method thereof, a pharmaceutical composition containing said derivative and a pharmaceutical formulation containing said derivative, a use of said compound in treating an excessive proliferative disease and a chronic obstructive pulmonary disease, and a use of said compound in the manufacture of a medicament for treating an excessive proliferative disease and a chronic obstructive pulmonary disease.

BACKGROUND ART

The protein tyrosine kinase is an enzyme that catalytically transfers the phosphate group from ATP to the tyrosine residue located at the protein substrate, and has a play in the normal cell growth. Many growth factor receptor proteins operate via the tyrosine kinase, and influence the conduction of signal passage and further regulate the cell growth by this process. However, in some circumstances, these receptors become abnormally due to either the mutation or the overexpression, which cause the uncontrolled cell multiplication, cause the tumor growth, and finally initiate the well-known disease, i.e., cancer. The growth factor receptor protein tyrosine kinase inhibitor, via the inhibition of the above phosphorylation process, may treat cancers and other diseases characterized by the uncontrolled or abnormal cell growth.

An epidermal growth factor receptor (EGFR) is a multifunction glycoprotein that is widely distributed on the cell membranes of the tissues of the human body, and is an oncogene analog of avian erythroblastic leukemia viral (v-erb-b). Human EGFR/HER1/ErbB-1 and HER2 (human epidermal growth factor receptor-2)/ErbB-2/Teu/p185, HER3/ErbB-3, HER4/ErbB-4 and the like are grouped into the HER/ErbB family, and belong to protein tyrosine kinases (PTKs). It is indicated in the clinical study that EGFR and the like are expressed in the epithelia-derived tumors such as squamous cell carcinoma of head and neck, mammary cancer, rectal cancer, ovarian cancer, prostate carcinoma, non-small cell lung cancer, and the like. Pan-HER tyrosine kinase inhibitor, via the competitive binding the kinase catalytic sites in the intracellular region against ATP, blocks the autophosphorylation of intramolecular tyrosine, blocks the tyrosine kinase activation, inhibits HER family activation, and therefore inhibits cell cycle progression, accelerates cell apoptosis, and exerts the therapeutic action.

EGFR, after binding the ligand, forms a dimer with a subgroup of HER family, and then combines with ATP to activate the tyrosine kinase activity of the EGFR itself. Therefore, the autophosphorylation occurs in several tyrosine sites of the intracellular kinase region. Pan-HER tyrosine kinase inhibitor, via simultaneity acting on EGFR, and HER2/4, inhibits the activation of HER family, and play a good role in the tumor growth inhibition.

It is indicated in the study that Pan-HER tyrosine kinase irreversible inhibitor has an inhibition effect on HER2/4, besides it effectively inhibits EGFR. The pharmaceutical drugs of this kind, having an irreversible inhibition to both of HER/ErbB families, not only increase the drug activity, but also reduce the drug resistance, and have a substantial inhibition effect on H1975 cell lines which are resistant to Erlotinib.

The pharmaceutical drugs that are now commercially available include selective EGFR tyrosine kinase inhibitor Gefitinb (Iressa, ZD1839), Erlotinib (Tarceva, OSI-774) and double EGFR/HER2 inhibitor Lapatinib (Tykerb, GW572016), and their structures are shown below. The above three drugs are all reversible EGF receptor tyrosine phosphorylation kinase inhibitor. It is found in the study that they have good therapeutic response to some tumors initially. However, several months after the treatment, the disease progression appears again and therefore a natural or secondary drug resistance forms.

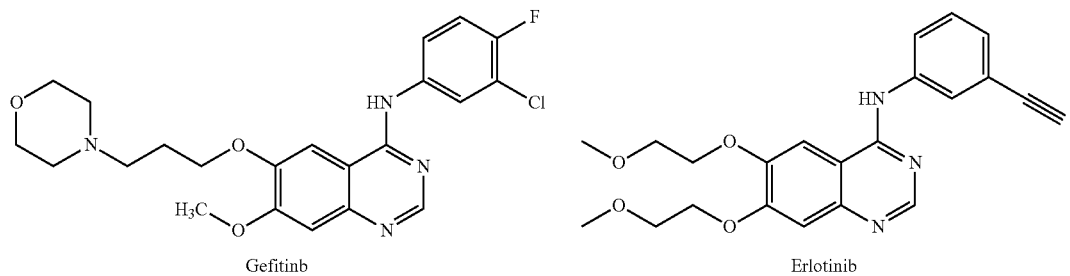

Gefitinb

Erlotinib

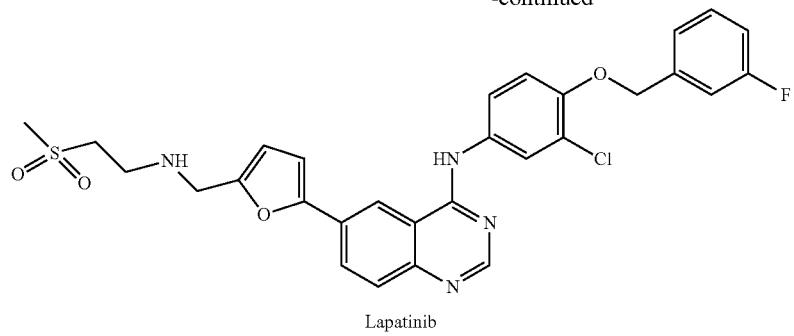

Lapatinib

It is reported in the literature (Bioorganic & Medicinal Chemistry (2008) 16 pages 3482-3488) that the commercially available drugs such as gefitinb and erlotinib have been widely used clinically. The long-term treatment of the late NSCLC (non-small cell lung cancer) may create an acquired drug-resistance, which has a negative effect on the therapeutical effect.

It is believed that the reversible EFG receptor tyrosine kinase inhibitor competes with ATP for the combination with EFG receptor tyrosine kinase. Due to the relative high concentration of the intracellular ATP (in order of mM), the reversible EGF receptor tyrosine kinase inhibitor, which shows a high activity in an in-vitro assay, is difficult to show the effect in the animal pathologic model. The irreversible EGF receptor tyrosine kinase inhibitor does not compete with ATP, and therefore it is expected that the non-reversible EGF receptor tyrosine kinase inhibitor may have a better in-vivo activity.

WO97/38983 discloses irreversible EGF receptor tyrosine kinase inhibitors. For these inhibitors, one Michael receptor is introduced at 6-position of quinazoline, and therefore a Michael addition reaction can be conducted between this receptor and —SH of the cysteine on the pouch wall of the EGF receptor tyrosine kinase activity center (Cys773). Moreover, the activities of these inhibitors and the complexity of the Michael addition reaction between these inhibitors and —SH of the cysteine are in a positive structure-function correlation.

US20010044435 A1 discloses a quinazoline derivative which has a lactone structure at 6-position of quinazoline. It is believed that it has an inhibition activity for the signal transduction mediated by the tyrosine kinase.

US20040044014 A1 discloses a quinazoline derivative which has a bridged ring structure at 6-position of quinazoline. It is believed that it has an inhibition activity for the signal transduction mediated by the tyrosine kinase.

It is reported in the reference (Adv Ther (2011) 28(2) p. 1-8) that PF-299 (Pfizer) and Afatinib (BIBW2992) (Boehringer Ingelheim) are in the clinical stage III, and Neratinib (HKI292) is in the clinical stage II. It is believed that these compounds are irreversible tyrosine kinase inhibitor, and can solve the EGFR resistance.

It is reported in the references (Cancer Res (2007); 67: (24) p. 11924-11932 and Mol Cancer Ther (2008); 7(7) p. 1880-1889) that PF-00299804 has an activity for some types of tumour. PF-00299804 has a structure of:

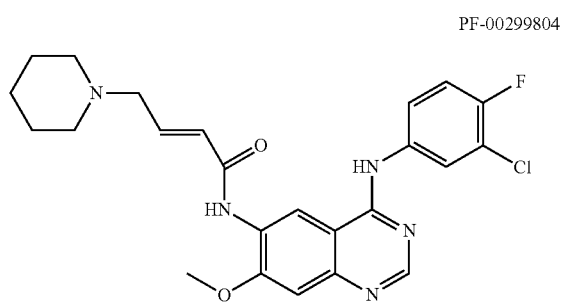 [SMILES: COc1cc2ncnc(Nc3ccc(F)c(Cl)c3)c2cc1NC(=O)/C=C/CN1CCCCC1]

PF-00299804

Upon developing the drug having a good antineoplastic effect, being able to reduce the drug resistance and having a good tolerance, the present inventors discover a quinazoline derivative as tyrosine kinase inhibitor having a Pan-HER irreversible inhibition function.

SUMMARY OF THE INVENTION

Therefore, the present invention provides a compound represented by the general formula (I), a pharmaceutically acceptable salt thereof and a stereoisomer thereof:

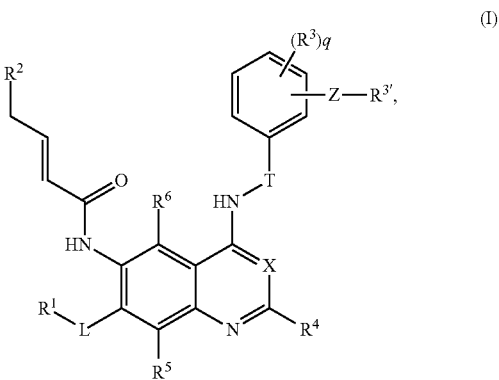

(I)

wherein:
$R^1$ is selected from the group consisting of the following groups that are unsubstituted or substituted by 1-3 same or different $Q^1$: $C_{1-6}$alkyl, $C_{3-6}$alkenyl, $C_{3-6}$alkynyl, $C_{3-8}$cycloalkyl-$C_{0-6}$alkyl, 6-10-membered fused ring-$C_{0-6}$alkyl, 7-10-membered spiro ring-$C_{0-6}$ alkyl and 7-10-membered bridged ring-$C_{0-6}$alkyl, and the carbon atom in said cycloalkyl, said fused ring, said spiro ring and said bridged ring may be optionally replaced by 1-3 hetero atoms and/or groups that may be identical or different and are selected from the group consisting of O, S(O)$_m$, N(H)$_n$ and/or C(O);

Q$^1$ is selected from the group consisting of halogen, hydroxy, amino, carboxyl, cyano, C$_{1-6}$alkyl, C$_{1-6}$alkoxyl, C$_{1-6}$alkylamino, di(C$_{1-6}$alkyl)amino, C$_{1-6}$alkylcarbonyloxy, C$_{1-4}$alkoxylcarbonyl, C$_{1-6}$alkylacylamino, C$_{1-6}$alkylsulfonyl, C$_{1-6}$alkylsulfinyl, C$_{1-6}$alkylsulfonylamino and C$_{3-8}$cycloalkyl;

R$^2$ is selected from the group consisting of the following groups that are unsubstituted or substituted by 1-3 same or different Q$^2$: C$_{3-4}$cycloalkyl-C$_{0-6}$alkyl, 6-10-membered fused ring-C$_{0-6}$alkyl, 7-10-membered spiro ring-C$_{0-6}$ alkyl and 7-10-membered bridged ring-C$_{0-6}$alkyl, and the carbon atom in said cycloalkyl, said fused ring, said spiro ring and said bridged ring may be optionally replaced by 1-3 hetero atoms and/or groups that may be identical or different and are selected from the group consisting of O, S(O)$_m$, N(H)$_n$ and/or C(O), provided that an ester structure "—O—C(O)—" is not present in the replaced ring, and when R$^2$ is 7-10-membered bridged ring-C$_{0-6}$alkyl, R$^1$ is not C$_{3-4}$cycloalkyl-C$_{0-6}$alkyl or C$_{1-6}$alkyl;

Q$^2$ is selected from the group consisting of halogen, hydroxy, amino, carboxyl, cyano, nitro, trifluoromethyl, C$_{1-6}$alkyl, C$_{1-6}$alkoxyl, C$_{1-6}$alkylamino, di(C$_{1-6}$alkyl)amino, C$_{1-6}$alkylcarbonyloxy, C$_{1-6}$alkoxylcarbonyl, C$_{1-6}$alkylacylamino, C$_{1-6}$alkylsulfonyl, C$_{1-6}$alkylsulfinyl and C$_{1-6}$alkylsulfonylamino;

R$^3$ is selected from the group consisting of halogen, hydroxy, cyano, nitro, trifluoromethyl, carbamoyl, C$_{1-6}$alkyl, C$_{2-6}$alkenyl, C$_{2-6}$alkynyl, C$_{1-6}$alkoxyl, C$_{1-6}$alkyl substituted with halogen, C$_{1-6}$alkoxyl substituted with halogen, C$_{1-6}$alkylamino, di(C$_{1-6}$alkyl)amino, C$_{1-6}$alkylthio, C$_{1-6}$alkylcarbamoyl, C$_{1-6}$alkylcarbonyl, C$_{1-6}$alkoxylcarbonyl, C$_{1-6}$alkylcarbonyloxy, C$_{1-6}$alkylacylamino, C$_{1-6}$alkylsulfonyl, C$_{1-6}$alkylsulfinyl and C$_{1-6}$alkylsulfonylamino;

R$^{3'}$ is absent;

R$^4$, R$^5$ and R$^6$ are each independently selected from the group consisting of hydrogen, halogen, C$_{1-6}$alkyl, C$_{1-6}$alkoxyl, C$_{1-6}$alkyl substituted with halogen, C$_{1-6}$alkoxyl substituted with halogen, C$_{1-6}$alkylamino and di(C$_{1-6}$alkyl) amino;

X is selected from the group consisting of cyano-substituted methenyl or a nitrogen atom;

L is selected from the group consisting of O, S(O)$_m$, N(H), N(CH$_3$) or C(O);

T is selected from the group consisting of a covalent bond, C(O) or CH(R'), R' is selected from the group consisting of hydrogen or C$_{1-6}$alkyl;

Z is hydrogen;

q is 2, and R$^3$ may be identical or different;

m is selected from the group consisting of 0, 1 or 2; and n is selected from the group consisting of 0 or 1.

The present invention also provides a pharmaceutical composition containing a compound represented by the general formula (I), a pharmaceutically acceptable salt thereof or a stereoisomer thereof.

The present invention also provides a pharmaceutical formulation containing a compound represented by the general formula (I), a pharmaceutically acceptable salt thereof or a stereoisomer thereof and a pharmaceutically acceptable carrier.

The present invention also provides a compound represented by the general formula (I), a pharmaceutically acceptable salt thereof or a stereoisomer thereof, or a pharmaceutical composition containing a compound represented by the general formula (I), a pharmaceutically acceptable salt thereof or a stereoisomer thereof as a medicament for treating an excessive proliferative disease and a chronic obstructive pulmonary disease.

The present invention also provides use of a compound represented by the general formula (I), a pharmaceutically acceptable salt thereof or a stereoisomer thereof, or a pharmaceutical composition containing a compound represented by the general formula (I), a pharmaceutically acceptable salt thereof or a stereoisomer thereof in the manufacture of a medicament for treating an excessive proliferative disease and a chronic obstructive pulmonary disease.

The present invention also provides a method for treating an excessive proliferative disease and a chronic obstructive pulmonary disease, which comprises the step of administering to a subject in need thereof an effective amount of a compound represented by the general formula (I), a pharmaceutically acceptable salt thereof or a stereoisomer thereof, or a pharmaceutical composition containing a compound represented by the general formula (I), a pharmaceutically acceptable salt thereof or a stereoisomer thereof.

The present invention also provides a process for preparing a compound of the general formula (I), comprising the steps of:

Reaction Procedure:

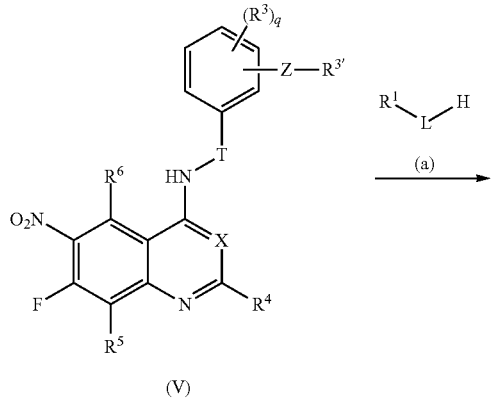

(V)

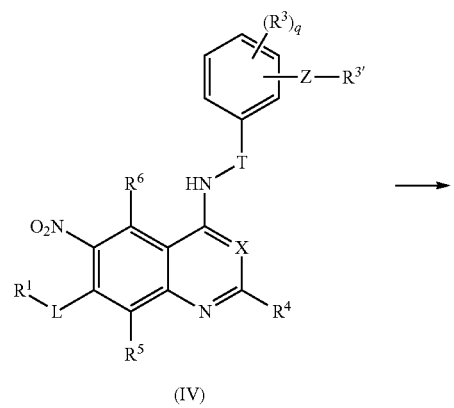

(IV)

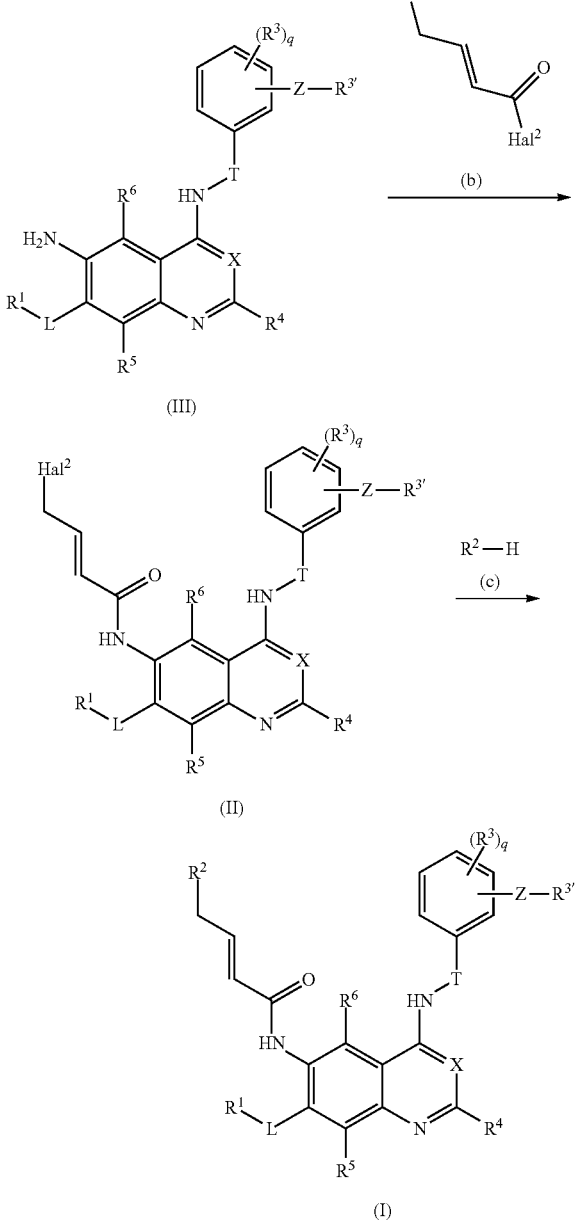

(DCM) or ethyl acetate (EA)), and reacting it with a compound of the formula (b) to produce a compound of the formula (II); and 4) Reacting the compound of the formula (II) and a compound of the formula (c) in the presence of a base (such as N,N-diisopropyl ethylamine (DIPEA), triethylamine (TEA), pyridine, $K_2CO_3$ or $Na_2CO_3$) to produce a compound of the formula (I);

where if necessary, a functional group that needs to be protected may be protected, and then deprotected according to the conventional method.

According to the present invention, the term "$C_{0-6}$alkyl" means a straight or branched alkyl group having a carbon atom number of 0-6 such as 0, 1, 2, 3, 4, 5 or 6. When the carbon atom number is zero, the alkyl is absent. The alkyl includes, for example, "$C_{0-4}$alkyl", "$C_{1-6}$alkyl", "$C_{2-5}$alkyl", and "$C_{1-4}$alkyl". Its example includes but is not limited to, e.g., methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methyl-2-methylpropyl and the like.

According to the present invention, the term "$C_{2-6}$alkenyl" means a straight or branched or cyclic hydrocarbyl group having a double bond and a carbon atom number of 2-6, and includes, for example, "$C_{3-6}$alkenyl", "$C_{3-5}$alkenyl", "$C_{2-4}$alkenyl" and the like. Its example includes but is not limited to, e.g., ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-2-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1,3-butadienyl, 1,3-pentadienyl, 1,4-pentadienyl, 1,4-hexadienyl, cyclopentenyl, 1,3-cyclopentadienyl, cyclohexenyl, 1,4-cyclohexadienyl and the like.

According to the present invention, the term "$C_{2-6}$alkynyl" means a straight or branched hydrocarbyl group containing a triple bond and having a carbon atom number of 2-6, including, for example, "$C_{3-6}$alkynyl", "$C_{3-5}$alkynyl", "$C_{2-4}$alkynyl" and the like. Its example includes but is not limited to, e.g., ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butywherein $R^1$, $R^2$, $R^3$, $R^{3'}$, $R^4$, $R^5$, $R^6$, X, L, T, Z and q are as defined hereinbefore, $Hal^1$ is selected from the group consisting of Cl, Br and I, $Hal^2$ is selected from the group consisting of Cl and Br, and $Hal^1$ and $Hal^2$ may be identical or different;

1) Dissolving a compound of the starting material (a) in an organic solvent (such as dimethyl formamide (DMF), acetonitrile, tetrahydrofuran (THF), methanol or ethanol), and reacting it with a compound of the formula (V) in the presence of an inorganic base (such as NaH, NaOH or KOH) to produce a compound of the formula (IV);

2) Reacting the compound of the formula (IV) and a reducing agent (such as Fe powder, Zn powder, Pd/C or Raney Ni) to produce a compound of the formula (III);

3) Dissolving the compound of the formula (III) in an organic solvent (such as tetrahydrofuran, dichlormethane nyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl, 1-ethyl-1-methyl-2-propynyl and the like.

According to the present invention, the term "$C_{1-6}$alkoxyl" means "$C_{1-6}$alkyl-O—", wherein $C_{1-6}$alkyl is defined as above; including, for example, "$C_{2-5}$alkoxyl", "$C_{1-4}$alkoxyl" and the like. Its example includes but is not limited to, e.g., methoxy, ethoxy, propoxy, iso-propoxy, butoxy, iso-butoxy, tert-butoxy, sec-butoxy, pentoxy, neopentoxy, hexyloxy and the like.

According to the present invention, the term "$C_{1-6}$alkylthio" means "$C_{1-6}$alkyl-S—", wherein $C_{1-6}$alkyl is defined as above, including, for example, "$C_{2-5}$alkylthio", "$C_{1-4}$ alkylthio" and the like. Its example includes but is not limited to, e.g., methylthio, ethylthio, propylthio, iso-propylthio, butylthio, iso-butylthio, tert-butylthio, sec-butylthio, pentylthio, neo-pentylthio, hexylthio and the like.

According to the present invention, the term "$C_{1-6}$alkylamino" means "$C_{1-6}$alkyl-NH—", wherein $C_{1-6}$alkyl is defined as above; including, for example, "$C_{2-5}$alkylamino", "$C_{1-4}$alkylamino" and the like. Its example includes but is not limited to, e.g., methylamino, ethylamino, propylamino, iso-propylamino, butylamino, iso-butylamino, tert-butylamino, sec-butylamino, pentylamino, neo-pentylamino, hexylamino and the like.

According to the present invention, the term "di($C_{1-6}$ alkyl)amino" means "($C_{1-6}$alkyl)$_2$-N—", wherein two $C_{1-6}$alkyls may be identical or different, and are respectively defined as above.

According to the present invention, the term "$C_{1-6}$alkylcarbonyloxy", "$C_{1-6}$alkoxylcarbonyl", "$C_{1-6}$alkylcarbonyl", "$C_{1-6}$alkylsulfonyl", "$C_{1-6}$alkylsulfinyl", "$C_{1-6}$alkylsulfonylamino", "$C_{1-6}$alkylacylamino" and "$C_{1-6}$alkylcarbamoyl" respectively mean "$C_{1-6}$alkyl-C(O)—O—", "$C_{1-6}$alkyl-O—C(O)—", "$C_{1-6}$alkyl-C(O)—", "$C_{1-6}$alkyl-SO$_2$—", "$C_{1-6}$ alkyl-SO—", "$C_{1-6}$alkyl-SO$_2$—NH—", "$C_{1-6}$alkyl-C(O)—NH—" and "$C_{1-6}$alkyl-NH—C(O)—", wherein "$C_{1-6}$ alkyl" is defined as above.

According to the present invention, the term "halogen" means fluoro, chloro, bromo, iodo and the like.

According to the present invention, the term "$C_{3-8}$cycloalkyl" means a cycloalkyl, which is derived from an alkane containing 3-8, such as 3, 4, 5, 6, 7 or 8 carbon atoms by removing one hydrogen atom, including, for example, "$C_{3-7}$cycloalkyl", "$C_{3-5}$cycloalkyl", "$C_{5-6}$cycloalkyl", "$C_{3-4}$ cycloalkyl" and the like, preferably "$C_{3-6}$cycloalkyl". Its example includes but is not limited to, e.g., cyclopropyl, cyclobutyl, cyclopentyl, cyclohexyl, cycloheptanyl, cyclooctanyl, methylcyclopropyl, dimethylcyclopropyl, methylcyclobutyl, dimethylcyclobutyl, methylcyclopentyl, dimethylcyclopentyl, methylcyclohexanyl, dimethylcyclohexanyl and the like.

According to the present invention, the term "6-10-membered fused ring" group means a saturated or unsaturated fused ring group containing 6-10 carbon atoms and formed by the linking of at least two cyclic structures sharing two adjacent atoms with each other, wherein the cyclocarbon atom(s) may be optionally replaced with 1-3 hetero atoms and/or groups that may be identical or different and are selected from the group consisting of O, S(O)$_m$, N(H)$_m$, NCH$_3$ and C(O). Its example includes but is not limited to 5,6-dihydroimidazo[1,2-a]pyrazin-7(8H)-yl, 5,6-dihydro-1,7-naphthyridin-7 (8H)-yl, 5H-pyrrolo[3,4-b]pyridin-6(7H)-yl, 7,8-dihydropyridino[4,3-d]pyrimidin-6(5H)-yl, 2,3,6,7-tetrahydro-1H-pyrazolo[4,3-c]pyridin-5(4H)-yl, 6,7-dihydrothiazolo[5,4-c]pyridin-5(4H)-yl, 3-methyl-6,7-dihydro-3H-pyrazolo[4,5-c]pyridin-5 (4H)-yl, 2-methylhexahydrocyclopenta[c]pyrrol-5-yl and the like.

According to the present invention, the term "7-10-membered spiro ring" group means a saturated or unsaturated fused ring group containing 7-10 carbon atoms and formed by at least two rings sharing the same atom, wherein the cyclocarbon atom(s) may be replaced with 1-3 hetero atoms and/or groups that may be identical or different and are selected from the group consisting of O, S(O)$_m$, N(H)$_m$, NCH$_3$ and C(O). Its example includes but is not limited to 6-azaspiro[2.5]octan-6-yl, 7-azaspiro[3.5]nonan-7-yl, 8-azaspiro[4.5]decan-8-yl, 1-methyl-1,7-diazaspiro[4.4]nonan-7-yl, 2-methyl-2,6-diazaspiro[3.4]octan-6-yl, 6-azaspiro[3.4]octan-6-yl, 2-oxa-7-azaspiro[4.5]decan-7-yl, 2-oxa-8-azaspiro[4.5]decan-8-yl, 2-methyl-2,7-diazaspiro[4.5]decane and the like.

According to the present invention, the term "7-10-membered bridged ring" group means a saturated or unsaturated fused ring group containing 7-10 carbon atoms and formed by any two rings sharing two atoms which are not directly linked, wherein the cyclocarbon atom(s) may be replaced with 1-3 hetero atoms and/or groups that may be identical or different and are selected from the group consisting of O, S(O)$_m$, N(H)$_m$, NCH$_3$ and C(O). Its example includes but is not limited to (1S,4S)-2-methyl-2-azabicyclo[2.2.1]hexanyl, 2-azabicyclo[2.2.1]heptanyl, 8-methylbicyclo[3.2.1]octanyl, 3-oxa-8-azabicyclo[3.2.1]octanyl, 2-azabicyclo[2.2.2]octanyl, 7-azabicyclo[2.2.1]heptanyl, 3-azabicyclo[3.2.1]octanyl, 3-azabicyclo[3.3.2]decanyl, 7-oxabicyclo[2.2.1]heptanyl, 8-oxabicyclo[3.2.1]octanyl and the like.

According to the present invention, the term "a covalent bond" means a single bond for attaching two atoms or groups.

In a preferable embodiment according to the compound of the general formula (I), R$^1$ is selected from the group consisting of the following groups that are unsubstituted or substituted by 1-2 same or different Q$^1$: $C_{1-4}$alkyl, $C_{3-8}$cycloalkyl-$C_{0-4}$alkyl, 6-10-membered fused ring-$C_{0-4}$alkyl, 7-10-membered spiro ring-$C_{0-4}$ alkyl and 7-10-membered bridged ring-$C_{0-4}$alkyl, and the carbon atom in said cycloalkyl, said fused ring, said spiro ring and said bridged ring may be optionally replaced by 1-2 hetero atoms and/or groups that may be identical or different and are selected from the group consisting of O, S(O)$_m$, N(H)$_n$ and/or C(O); wherein m is selected from the group consisting of 0, 1 or 2, n is selected from the group consisting of 0 or 1, and Q$^1$ is selected from the group consisting of halogen, hydroxy, amino, carboxyl, cyano, $C_{1-4}$alkyl, $C_{1-4}$alkoxyl, $C_{1-4}$alkylamino, di($C_{1-4}$alkyl)amino, $C_{1-4}$alkylcarbonyloxy, $C_{1-4}$alkoxylcarbonyl, $C_{1-4}$alkylacylamino, $C_{1-4}$alkylsulfonyl, $C_{1-4}$alkylsulfinyl, $C_{1-4}$alkylsulfonylamino and $C_{3-8}$cycloalkyl.

In a further preferable embodiment according to the compound of the general formula (I), R$^1$ is selected from the group consisting of the following groups that are unsubstituted or substituted by 1-2 same or different Q$^1$:
(1) $C_{1-4}$alkyl, cyclopropyl-$C_{0-4}$alkyl, cyclobutyl-$C_{0-4}$alkyl, cyclopentyl-$C_{0-4}$alkyl, cyclohexyl-$C_{0-4}$ alkyl and cycloheptyl-$C_{0-4}$alkyl, the carbon atom in said cyclopropyl, said cyclobutyl, said cyclopentyl, said cyclohexyl and said cycloheptyl may be optionally replaced by 1-2 hetero atoms and/or groups that may be identical or different and are selected from the group consisting of O, S(O)$_m$, N(H)$_n$ and/or C(O), wherein, m is selected from the group consisting of 0, 1 or 2, and n is selected from the group consisting of 0 or 1: and (2)

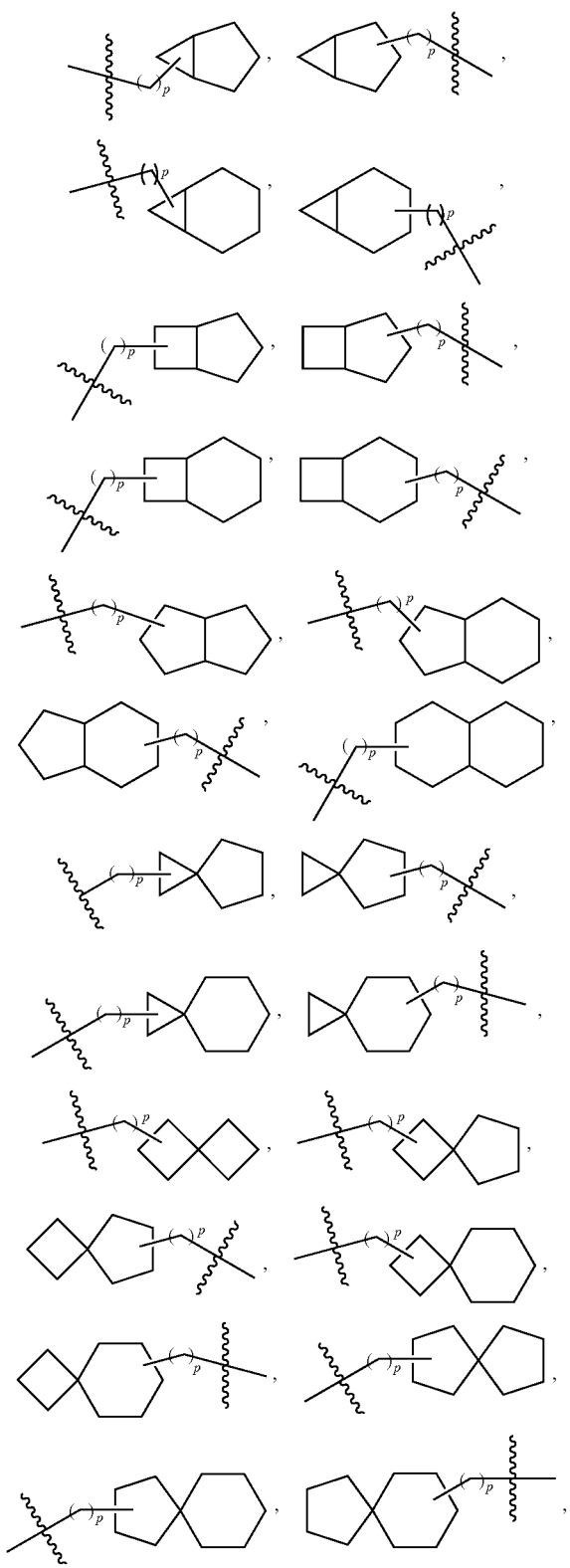
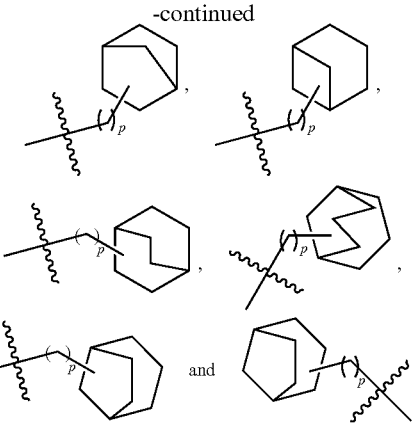
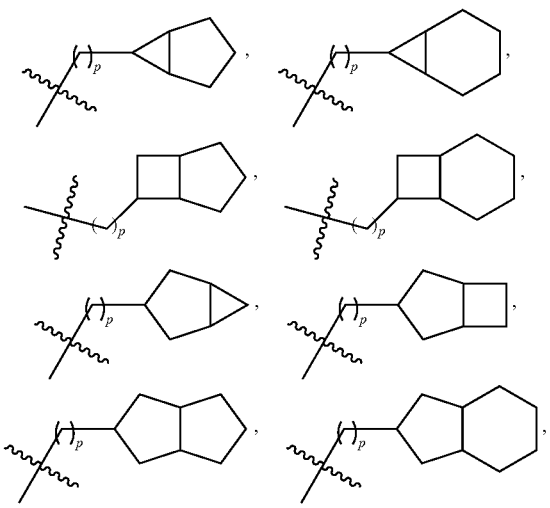

the carbon atom in said ring may be optionally replaced by 1-2 hetero atoms and/or groups that may be identical or different and are selected from the group consisting of O, $S(O)_m$, $N(H)_n$ and/or C(O), wherein p is selected from the group consisting of 0, 1 or 2, m is selected from the group consisting of 0, 1 or 2, and n is selected from the group consisting of 0 or 1;

and $Q^1$ is selected from the group consisting of halogen, hydroxy, amino, carboxyl, cyano, methyl, ethyl, methoxy, ethoxy, methylamino, ethylamino, dimethylamino, diethylamino, acetoxy, acetylamino, methylsulfonyl, ethylsulfonyl, methylsulfinyl, methylsulfonylamino, ethylsulfonylamino, cyclopropyl, cyclobutyl, cyclopentyl and cyclohexyl.

In a further preferable embodiment according to the compound of the general formula (I), $R^1$ is selected from the group consisting of the following groups that are unsubstituted or substituted by $Q^1$:

(1) methyl, ethyl, propyl, cyclopropyl-$C_{0-3}$alkyl, cyclobutyl-$C_{0-3}$alkyl, cyclopentyl-$C_{0-3}$alkyl, cyclohexyl-$C_{0-3}$alkyl, azetidinyl-$C_{0-3}$alkyl, tetrahydrofuryl-$C_{0-3}$alkyl, pyrrolidinyl-$C_{0-3}$alkyl, piperidinyl-$C_{0-3}$alkyl, morpholinyl-$C_{0-3}$alkyl and piperazinyl-$C_{0-3}$alkyl; and (2)

-continued

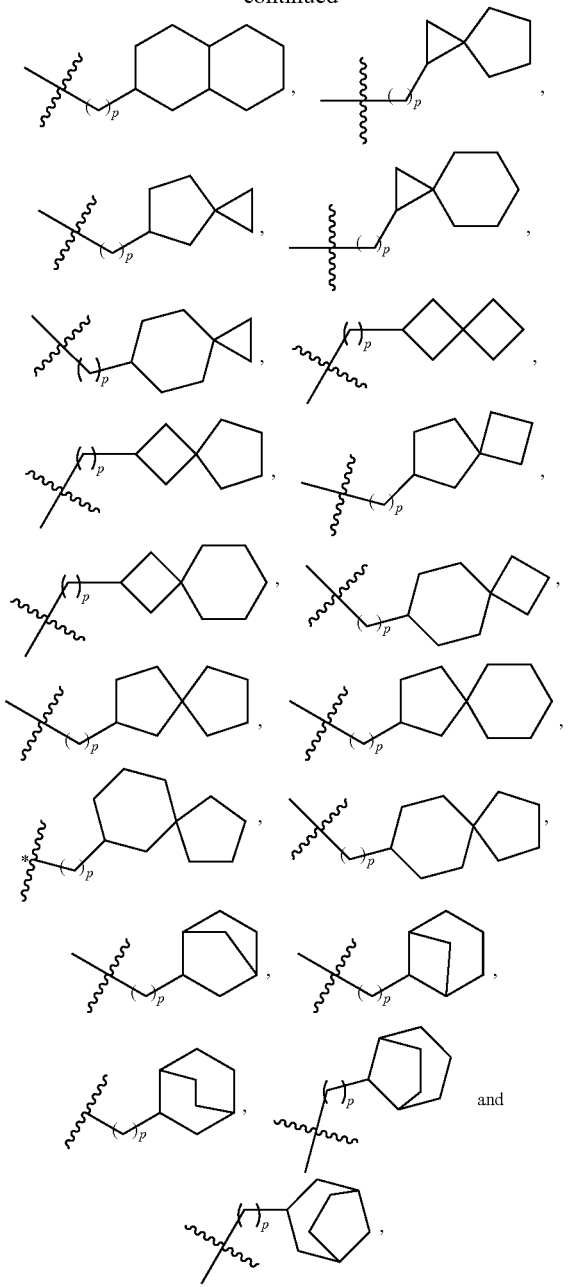

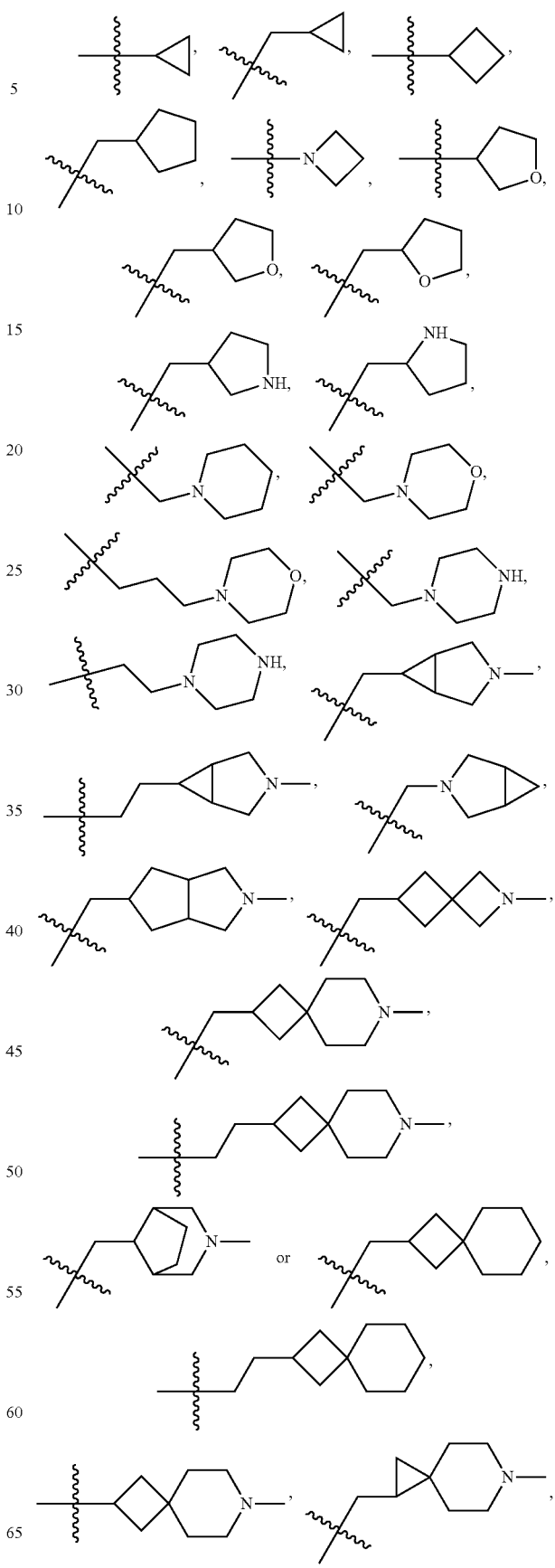

the carbon atom in said ring may be optionally replaced by 1-2 hetero atoms and/or groups that may be identical or different and are selected from the group consisting of O, $S(O)_m$, $N(H)_n$ and/or $C(O)$, wherein p is selected from the group consisting of 0, 1 or 2, m is selected from the group consisting of 0, 1 or 2, and n is selected from the group consisting of 0 or 1;
and
$Q^1$ is selected from the group consisting of halogen, hydroxy, amino, carboxyl, cyano, methyl, ethyl, methoxy, ethoxy, methylamino, ethylamino, dimethylamino and diethylamino.

In a further preferable embodiment according to the compound of the general formula (I), $R^1$ is selected from the group consisting of the following groups that are unsubstituted or substituted by 1-2 same or different $Q^1$: methyl, ethyl,

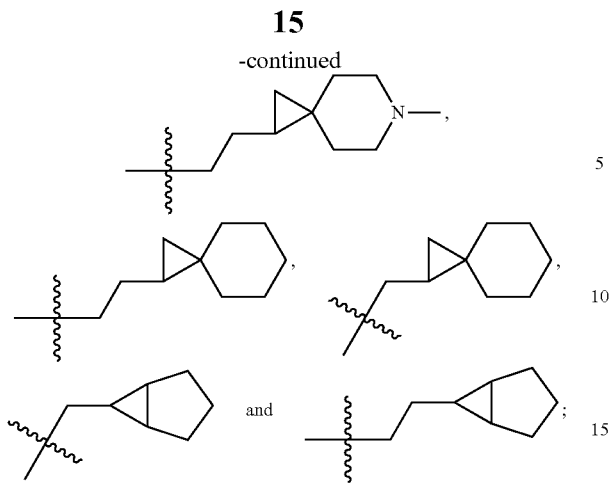

and $Q^1$ is selected from the group consisting of halogen, hydroxy, amino, carboxyl, methyl, ethyl, methoxy, ethoxy, methylamino, ethylamino, dimethylamino and diethylamino.

In a preferable embodiment according to the compound of the general formula (I), $R^2$ is selected from the group consisting of the following groups that are unsubstituted or substituted by 1-2 same or different $Q^2$: cyclopropyl-$C_{0-4}$alkyl, cyclobutyl-$C_{0-4}$alkyl, 6-10-membered fused ring-$C_{0-4}$alkyl, 7-10-membered spiro ring-$C_{0-4}$alkyl or 7-10-membered bridged ring-$C_{0-4}$alkyl, and the carbon atom in said cyclopropyl, said cyclobutyl, said fused ring, said spiro ring and said bridged ring may be replaced by 1-2 hetero atoms and/or groups that may be identical or different and are selected from the group consisting of O, $S(O)_m$, $N(H)_n$ and/or $C(O)$, provided that an ester structure "—O—C(O)—" is not present in the replaced ring, wherein m is selected from the group consisting of 0, 1 or 2, and n is selected from the group consisting of 0 or 1; $Q^2$ is selected from the group consisting of halogen, hydroxy, amino, cyano, $C_{1-4}$alkyl, $C_{1-4}$alkoxyl, $C_{1-4}$alkylamino, di($C_{1-4}$alkyl)amino, $C_{1-4}$alkylcarbonyloxy, $C_{1-4}$alkoxylcarbonyl, $C_{1-4}$alkylacylamino, $C_{1-4}$alkylsulfonyl, $C_{1-4}$alkylsulfinyl and $C_{1-4}$alkylsulfonylamino.

In a further preferable embodiment according to the compound of the general formula (I), $R^2$ is selected from the group consisting of (1) the following groups that are unsubstituted or substituted by 1-2 same or different $Q^2$:

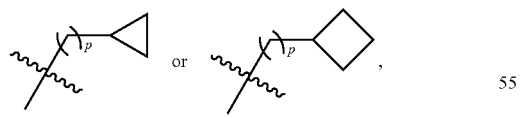

the carbon atom in said ring may be replaced by 1-2 hetero atoms and/or groups that may be identical or different and are selected from the group consisting of O, $S(O)_m$, $N(H)_n$ and/or $C(O)$, provided that an ester structure "—O—C(O)—" is not present in the replaced ring; wherein p is selected from the group consisting of 0, 1 or 2, m is selected from the group consisting of 0, 1 or 2, and n is selected from the group consisting of 0 or 1; and (2)

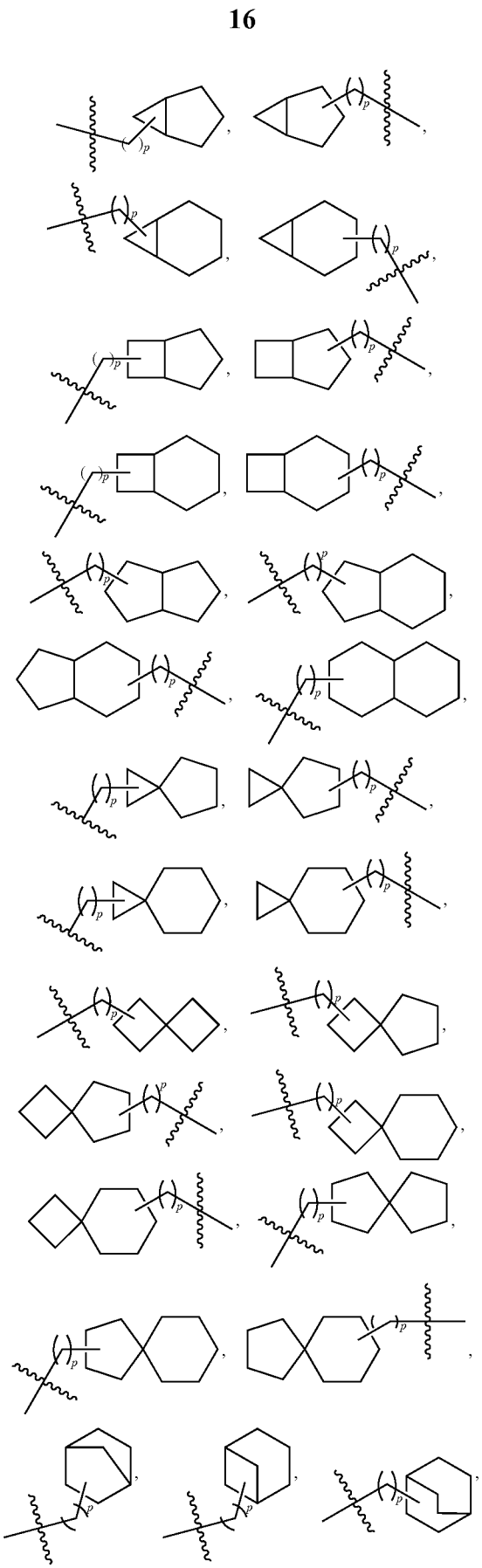

-continued

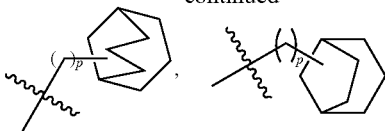

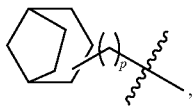

the carbon atom in said ring may be optionally replaced by 1-2 hetero atoms and/or groups that may be identical or different and are selected from the group consisting of O, $S(O)_m$, $N(H)_n$ and/or C(O), provided that an ester structure "—O—C(O)—" is not present in the replaced ring, wherein p is selected from the group consisting of 0, 1 or 2, m is selected from the group consisting of 0, 1 or 2, and n is selected from the group consisting of 0 or 1; and $Q^2$ is selected from the group consisting of halogen, hydroxy, amino, methyl, ethyl, methoxy, ethoxy, methylamino, ethylamino, dimethylamino, diethylamino, acetoxy, acetylamino, methylsulfonyl and methylsulfonylamino.

In a further preferable embodiment according to the compound of the general formula (I), $R^2$ is selected from the group consisting of (1)

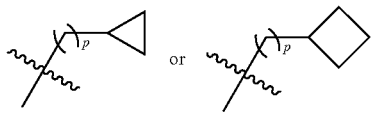

that is unsubstituted or substituted by $Q^2$, the carbon atom in said ring may be replaced by 1-2 hetero atoms and/or groups that may be identical or different and are selected from the group consisting of O, $S(O)_m$, $N(H)_n$ and/or C(O), provided that an ester structure "—O—C(O)—" is not present in the replaced ring; wherein p is selected from the group consisting of 0, 1 or 2, m is selected from the group consisting of 0, 1 or 2, and n is selected from the group consisting of 0 or 1; and (2)

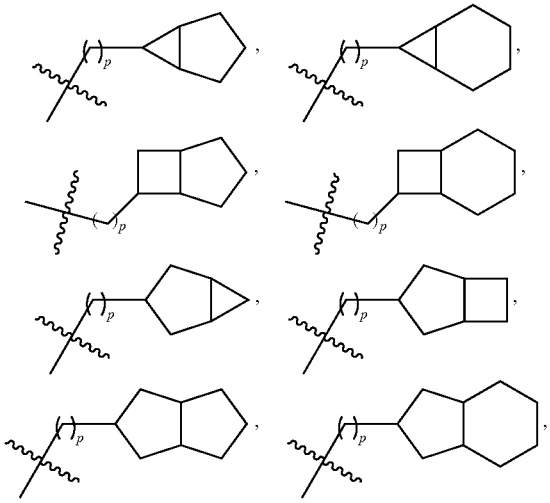

-continued

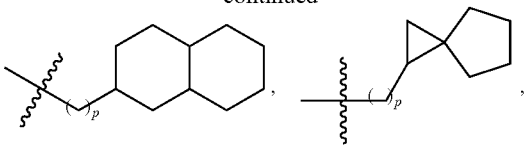

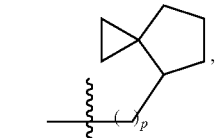

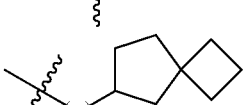

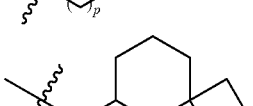

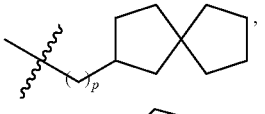

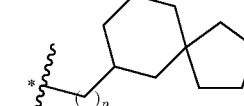

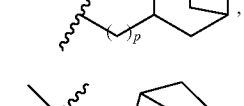

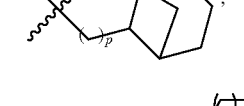

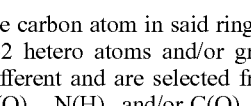

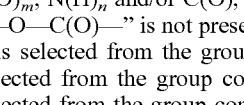

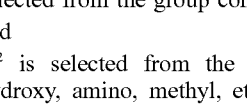

the carbon atom in said ring may be optionally replaced by 1-2 hetero atoms and/or groups that may be identical or different and are selected from the group consisting of O, $S(O)_m$, $N(H)_n$ and/or C(O), provided that an ester structure "—O—C(O)—" is not present in the replaced ring, wherein p is selected from the group consisting of 0, 1 or 2, m is selected from the group consisting of 0, 1 or 2, and n is selected from the group consisting of 0 or 1; and $Q^2$ is selected from the group consisting of halogen, hydroxy, amino, methyl, ethyl, methoxy, ethoxy, methylamino, ethylamino, dimethylamino, diethylamino, acetoxy, acetylamino, methylsulfonyl and methylsulfonylamino.

In a further preferable embodiment according to the compound of the general formula (I), $R^2$ is selected from the group consisting of the following groups that are unsubstituted or substituted by 1-2 same or different $Q^2$:

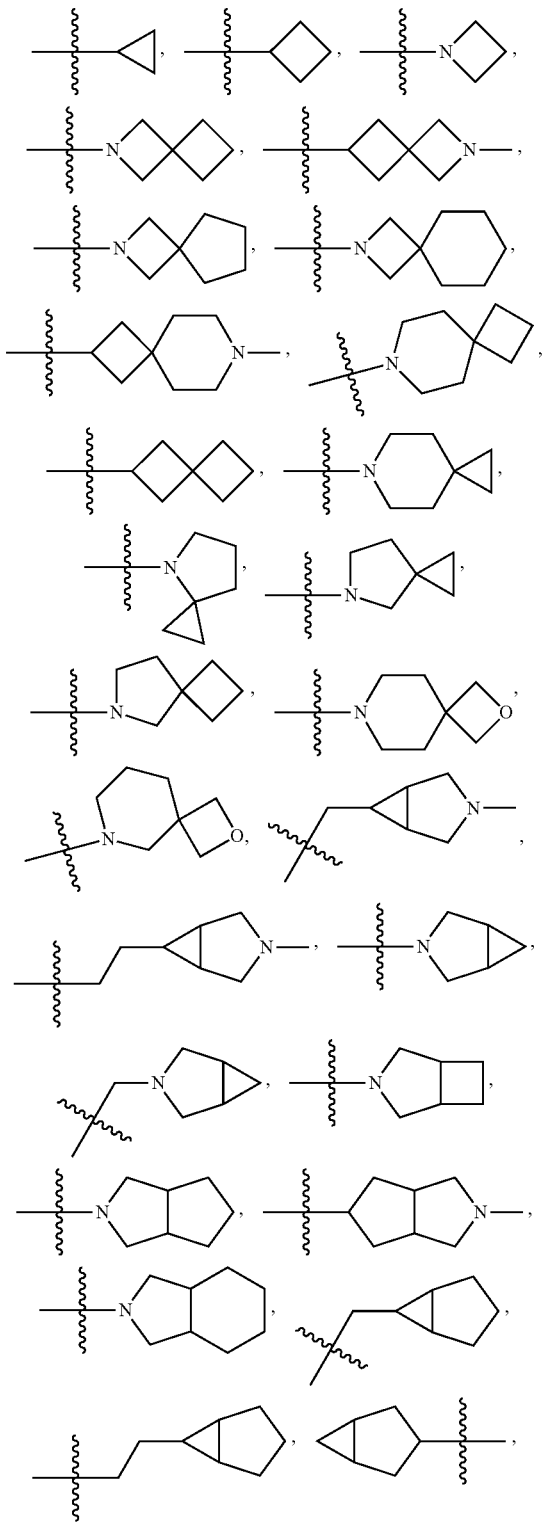

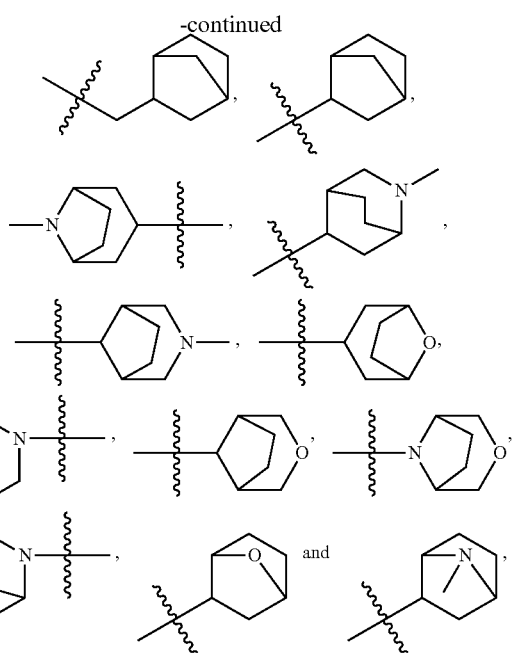

and $Q^2$ is selected from the group consisting of halogen, hydroxy, amino, methyl, ethyl, methoxy, ethoxy, methylamino, ethylamino, dimethylamino, diethylamino, acetoxy, acetylamino, methylsulfonyl and methylsulfonylamino.

In a preferable embodiment according to the compound of the general formula (I), $R^3$ is selected from the group consisting of halogen, hydroxy, cyano, nitro, trifluoromethyl, carbamoyl, $C_{1-4}$alkyl, $C_{2-4}$alkenyl, $C_{2-4}$alkynyl, $C_{1-4}$alkoxyl, $C_{1-4}$alkyl substituted with halogen, $C_{1-4}$alkoxyl substituted with halogen, $C_{1-4}$alkylamino, di($C_{1-4}$alkyl)amino, $C_{1-4}$alkylthio, $C_{1-4}$alkylcarbamoyl, $C_{1-4}$alkylcarbonyl, $C_{1-4}$alkoxylcarbonyl, $C_{1-4}$alkylcarbonyloxy, $C_{1-4}$alkylacylamino, $C_{1-4}$alkylsulfonyl, $C_{1-4}$alkylsulfinyl and $C_{1-4}$alkylsulfonylamino.

In a further preferable embodiment according to the compound of the general formula (I), $R^3$ is selected from the group consisting of halogen, hydroxy, cyano, nitro, trifluoromethyl, carbamoyl, methyl, ethyl, ethenyl, ethynyl, methoxy, methyl substituted with halogen, methoxy substituted with halogen, methylamino, ethylamino, dimethylamino, methylthio, methylcarbamoyl, acetyl, methoxycarbonyl, acetoxy, acetylamino and methylsulfonylamino.

In a further preferable embodiment according to the compound of the general formula (I), $R^3$ is halogen, which is selected from the group consisting of fluoro, chloro, bromo, or iodo.

In a preferable embodiment according to the compound of the general formula (I), $R^4$, $R^5$ and $R^6$ are each independently selected from the group consisting of hydrogen, halogen, $C_{1-4}$alkyl, $C_{1-4}$alkoxyl, $C_{1-4}$alkyl substituted with halogen, $C_{1-4}$alkoxyl substituted with halogen, $C_{1-4}$alkylamino and di($C_{1-4}$alkyl)amino.

In a further preferable embodiment according to the compound of the general formula (I), $R^4$, $R^5$ and $R^6$ are each independently selected from the group consisting of hydrogen, halogen, methyl, methoxy, methyl substituted with halogen, methoxy substituted with halogen, methylamino and dimethylamino.

In a preferable embodiment according to the compound of the general formula (I), X is a nitrogen atom.

In a preferable embodiment according to the compound of the general formula (I), L is selected from the group consisting of O, S(O)$_m$ or N(H)$_n$; particularly preferably O.

In a preferable embodiment according to the compound of the general formula (I), T is selected from the group consisting of a covalent bond or CH(R'), R' is selected from the group consisting of hydrogen or C$_{1-4}$alkyl, such as methyl.

In a further preferable embodiment according to the compound of the general formula (I), T is a covalent bond, accordingly said compound has a structure of the following formula (I-1):

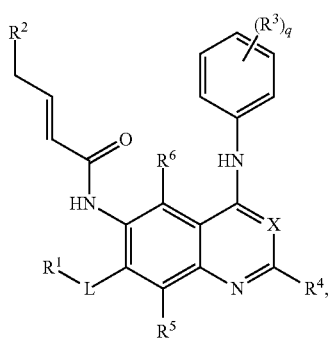

(I-1)

wherein R$^1$, R$^2$, R$^3$, R$^4$, R$^5$, R$^6$, X, L and q are defined as above.

In a preferable embodiment according to the compound of the general formula (I-1), R$^3$ is halogen, which is selected from the group consisting of chloro or fluoro, X is a nitrogen atom, and said compound has a structure of the following formula (I-2):

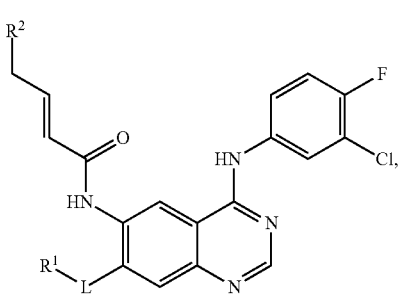

(I-2)

wherein R$^1$, R$^2$ and L are defined as above.

In another preferable embodiment according to the compound of the general formula (I), R$^1$ is selected from the group consisting of the following groups that are unsubstituted or substituted by 1-3 same or different Q$^1$: C$_{1-4}$alkyl, C$_{3-8}$cycloalkyl-C$_{0-4}$alkyl, 6-10-membered fused ring-C$_{0-4}$ alkyl, 7-10-membered spiro ring-C$_{0-4}$ alkyl and 7-10-membered bridged ring-C$_{0-4}$alkyl, the carbon atom in said cycloalkyl, said fused ring, said spiro ring or said bridged ring may be optionally replaced by 1-3 hetero atoms and/or groups that may be identical or different and are selected from the group consisting of O, S(O)$_m$, N(H)$_n$ and/or C(O), Q$^1$ is selected from the group consisting of halogen, hydroxy, amino, carboxyl, cyano, C$_{1-4}$alkyl, C$_{1-4}$alkoxyl, C$_{1-4}$alkylamino, di(C$_{1-4}$alkyl)amino, C$_{1-4}$alkylcarbonyloxy, C$_{1-4}$alkoxylcarbonyl, C$_{1-4}$alkylacylamino, C$_{1-4}$alkylsulfonyl, C$_{1-4}$alkylsulfinyl, C$_{1-4}$alkylsulfonylamino and C$_{3-8}$cycloalkyl;

R$^2$ is selected from the group consisting of the following groups that are unsubstituted or substituted by 1-2 same or different Q$^2$: cyclopropyl-C$_{0-4}$alkyl, cyclobutyl-C$_{0-4}$alkyl, 6-10-membered fused ring-C$_{0-4}$alkyl, 7-10-membered spiro ring-C$_{0-4}$alkyl or 7-10-membered bridged ring-C$_{0-4}$alkyl, the carbon atom in said cyclopropyl, said cyclobutyl, said fused ring, said spiro ring or said bridged ring may be optionally replaced by 1-2 hetero atoms and/or groups that may be identical or different and are selected from the group consisting of O, S(O)$_m$, N(H)$_n$ and/or C(O), provided that an ester structure "—O—C(O)—" is not present in the replaced ring, and when R$^2$ is 7-10-membered bridged ring-C$_{0-4}$alkyl, R$^1$ is not C$_{3-4}$cycloalkyl-C$_{0-4}$alkyl or C$_{1-4}$alkyl; Q$^2$ is selected from the group consisting of halogen, hydroxy, amino, cyano, C$_{1-4}$alkyl, C$_{1-4}$alkoxyl, C$_{1-4}$alkylamino, di(C$_{1-4}$alkyl)amino, C$_{1-4}$alkylcarbonyloxy, C$_{1-4}$alkoxylcarbonyl, C$_{1-4}$alkylacylamino, C$_{1-4}$alkylsulfonyl, C$_{1-4}$alkylsulfinyl and C$_{1-4}$alkylsulfonylamino;

R$^3$ is selected from the group consisting of hydrogen, halogen, hydroxy, cyano, nitro, carbamoyl, C$_{1-4}$alkyl, C$_{2-4}$alkenyl, C$_{2-4}$alkynyl, C$_{1-4}$alkoxyl, C$_{1-4}$alkyl substituted with halogen, C$_{1-4}$alkoxyl substituted with halogen, C$_{1-4}$alkylamino, di(C$_{1-4}$alkyl)amino, C$_{1-4}$alkylthio, C$_{1-4}$alkylcarbamoyl, C$_{1-4}$alkylcarbonyl, C$_{1-4}$alkoxylcarbonyl, C$_{1-4}$alkylcarbonyloxy, C$_{1-4}$alkylacylamino, C$_{1-4}$alkylsulfonyl, C$_{1-4}$alkylsulfinyl and C$_{1-4}$alkylsulfonylamino;

R$^{3'}$ is absent;

R$^4$, R$^5$ and R$^6$ are each independently selected from the group consisting of hydrogen, halogen, C$_{1-4}$alkyl, C$_{1-4}$alkoxyl, C$_{1-4}$alkyl substituted with halogen, C$_{1-4}$alkoxyl substituted with halogen, C$_{1-4}$alkylamino and di(C$_{1-4}$alkyl)amino;

X is selected from the group consisting of cyano-substituted methenyl or a nitrogen atom;

L is selected from the group consisting of O, S(O)$_m$ or N(H);

T is selected from the group consisting of a covalent bond or CH(R'), R' is selected from the group consisting of hydrogen or methyl;

Z is hydrogen;

q is 2, and R$^3$ may be identical or different;

m is selected from the group consisting of 0, 1 or 2; and n is selected from the group consisting of 0 or 1.

In another preferable embodiment according to the compound of the general formula (I), R$^1$ is selected from the group consisting of the following groups that are unsubstituted or substituted by 1-2 same or different Q$^1$:

(1) C$_{1-4}$alkyl, cyclopropyl-C$_{0-4}$alkyl, cyclobutyl-C$_{0-4}$alkyl, cyclopentyl-C$_{0-4}$alkyl, cyclohexyl-C$_{0-4}$ alkyl and cycloheptyl-C$_{0-4}$alkyl, the carbon atom in said cyclopropyl, said cyclobutyl, said cyclopentyl, said cyclohexyl and said cycloheptyl may be optionally replaced by 1-2 hetero atoms and/or groups that may be identical or different and are selected from the group consisting of O, S(O)$_m$, N(H)$_n$ and/or C(O); and (2)

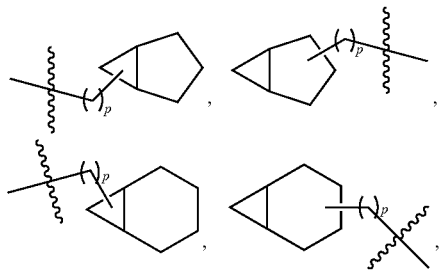

-continued

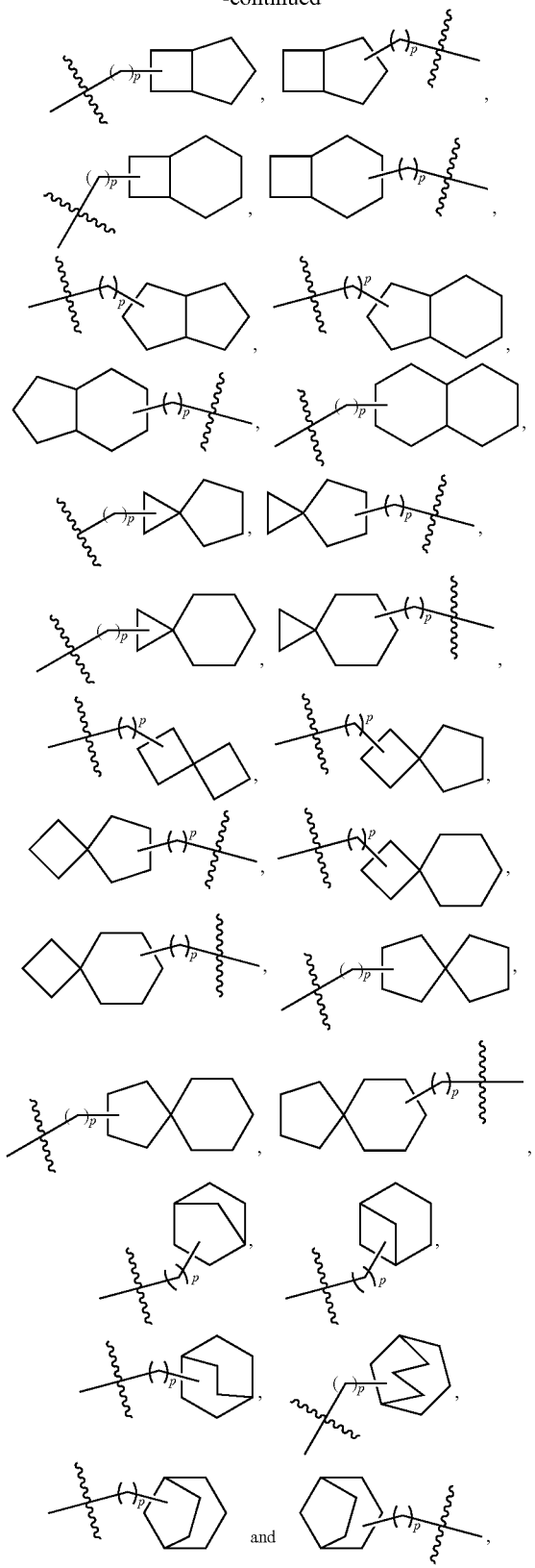

the carbon atom in said ring may be optionally replaced by 1-2 hetero atoms and/or groups that may be identical or different and are selected from the group consisting of O, S(O)$_m$, N(H)$_n$ and/or C(O), wherein p is selected from the group consisting of 0, 1 or 2;
and
Q$^1$ is selected from the group consisting of halogen, hydroxy, amino, carboxyl, cyano, methyl, ethyl, methoxy, ethoxy, methylamino, ethylamino, dimethylamino, diethylamino, acetoxy, acetylamino, methylsulfonyl, ethylsulfonyl, methylsulfinyl, methylsulfonylamino, ethylsulfonylamino, cyclopropyl, cyclobutyl, cyclopentyl and cyclohexyl;
R$^2$ is selected from the group consisting of
(1) the following groups that are unsubstituted or substituted by 1-2 same or different Q$^2$:

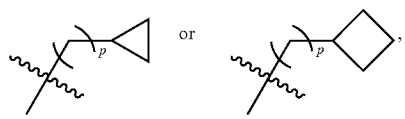

the carbon atom in said ring may be replaced by 1-2 hetero atoms and/or groups that may be identical or different and are selected from the group consisting of O, S(O)$_m$, N(H)$_n$ and/or C(O), provided that an ester structure "—O—C(O)—" is not present in the replaced ring; p is selected from the group consisting of 0, 1 or 2; and
(2)

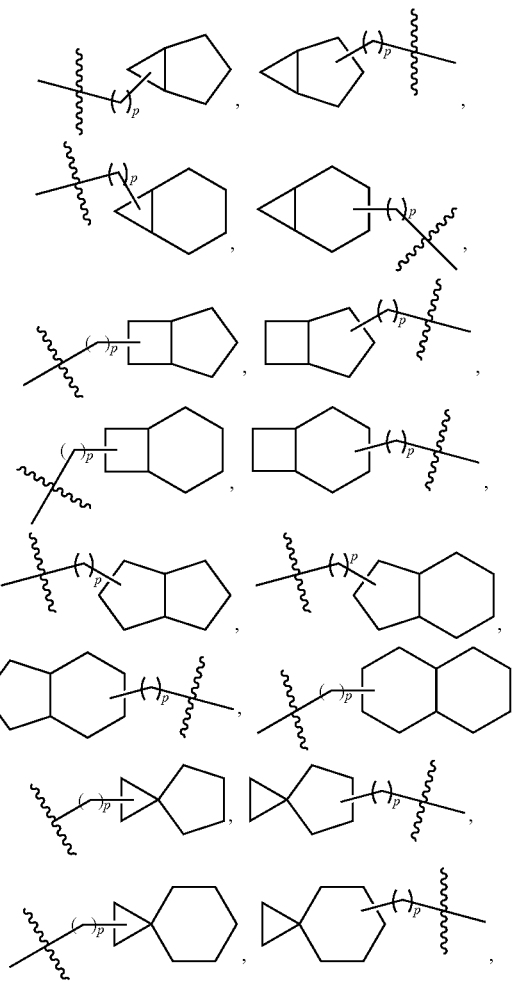

-continued

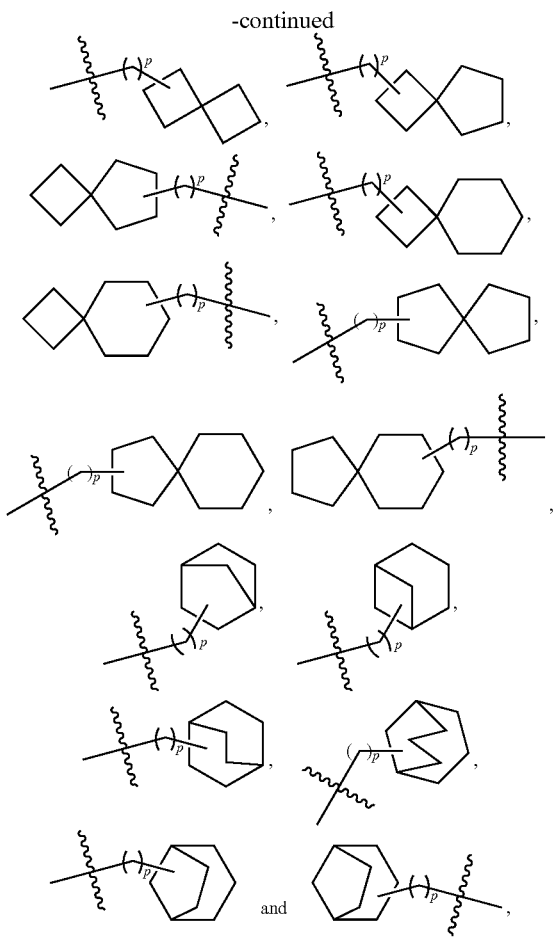

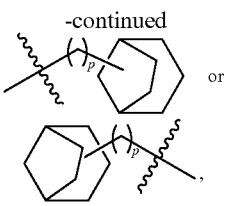

the carbon atom in said ring may be optionally replaced by 1-2 hetero atoms and/or groups that may be identical or different and are selected from the group consisting of O, S(O)$_m$, N(H)$_n$ and/or C(O), provided that an ester structure "—O—C(O)—" is not present in the replaced ring, wherein p is selected from the group consisting of 0, 1 or 2, and when R$^2$ is

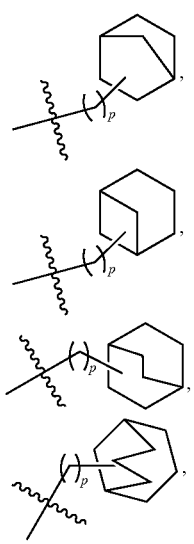

$R^1$ is not $C_{1-4}$alkyl, cyclopropyl-$C_{0-4}$alkyl or cyclobutyl-$C_{0-4}$ alkyl; and
$Q^2$ is selected from the group consisting of halogen, hydroxy, amino, methyl, ethyl, methoxy, ethoxy, methylamino, ethylamino, dimethylamino, diethylamino, acetoxy, acetylamino, methylsulfonyl and methylsulfonylamino;
$R^3$ is selected from the group consisting of halogen, hydroxy, cyano, nitro, trifluoromethyl, carbamoyl, methyl, ethyl, ethenyl, ethynyl, methoxy, methyl substituted with halogen, methoxy substituted with halogen, methylamino, ethylamino, dimethylamino, methylthio, methylcarbamoyl, acetyl, methoxycarbonyl, acetoxy, acetylamino and methylsulfonylamino;
$R^{3'}$ is absent;
$R^4$, $R^5$ and $R^6$ are each independently selected from the group consisting of hydrogen, halogen, methyl, methoxy, methyl substituted with halogen, methoxy substituted with halogen, methylamino and dimethylamino;
X is selected from the group consisting of cyano-substituted methenyl or a nitrogen atom;
L is O;
T is selected from the group consisting of a covalent bond or CH(R'), R' is selected from the group consisting of hydrogen or methyl;
Z is hydrogen;
q is 2, $R^3$ may be identical or different;
m is selected from the group consisting of 0, 1 or 2; and
n is selected from the group consisting of 0 or 1.

In a further preferable embodiment according to the compound of the general formula (I), $R^1$ is selected from the group consisting of the following groups that are unsubstituted or substituted by $Q^1$:
(1) methyl, ethyl, propyl, cyclopropyl-$C_{0-3}$alkyl, cyclobutyl-$C_{0-3}$alkyl, cyclopentyl-$C_{0-3}$alkyl, cyclohexyl-$C_{0-3}$ alkyl, azetidinyl-$C_{0-3}$alkyl, tetrahydrofuryl-$C_{0-3}$alkyl, pyrrolidinyl-$C_{0-3}$alkyl, piperidinyl-$C_{0-3}$alkyl, morpholinyl-$C_{0-3}$ alkyl and piperazinyl-$C_{0-3}$alkyl; and
(2)

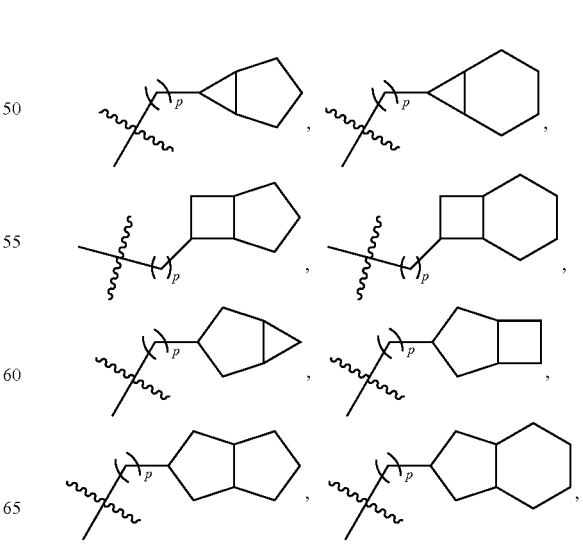

-continued

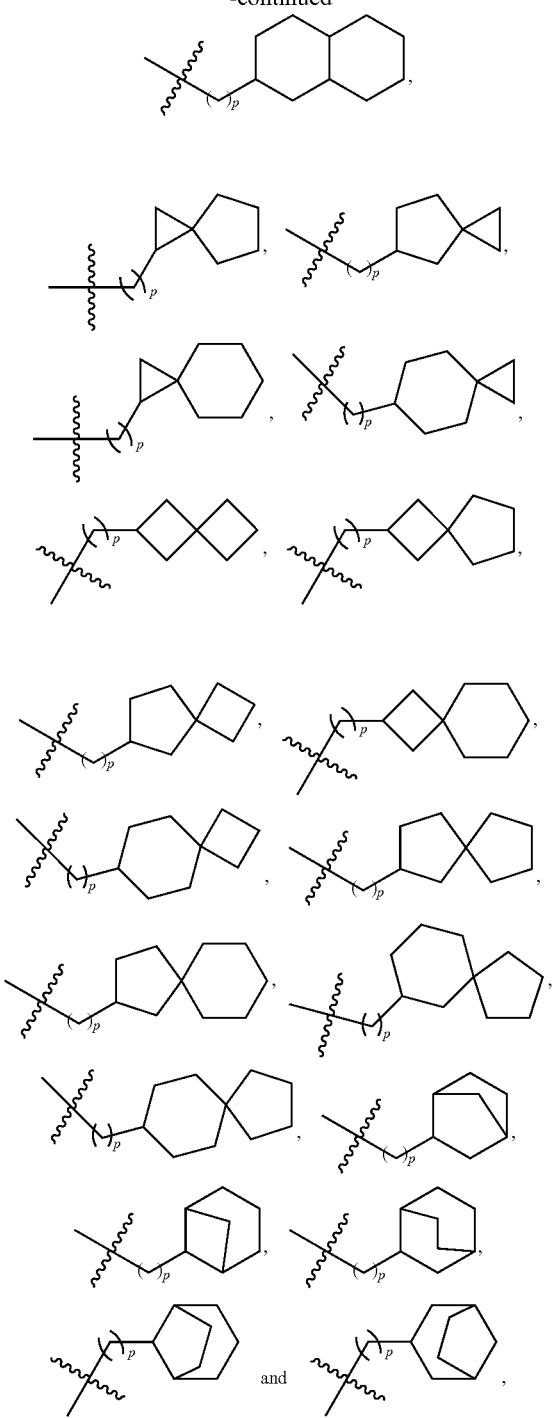

the carbon atom in said ring may be optionally replaced by 1-2 hetero atoms and/or groups that may be identical or different and are selected from the group consisting of O, $S(O)_m$, $N(H)_n$ and/or C(O), wherein p is selected from the group consisting of 0, 1 or 2;

and $Q^1$ is selected from the group consisting of halogen, hydroxy, amino, carboxyl, cyano, methyl, ethyl, methoxy, ethoxy, methylamino, ethylamino, dimethylamino and diethylamino;

$R^2$ is selected from the group consisting of (1)

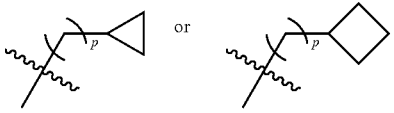

that is unsubstituted or substituted by $Q^2$, the carbon atom in said ring may be replaced by 1-2 hetero atoms and/or groups that may be identical or different and are selected from the group consisting of O, $S(O)_m$, $N(H)_n$ and/or C(O), provided that an ester structure "—O—C(O)—" is not present in the replaced ring; wherein p is selected from the group consisting of 0, 1 or 2; and (2)

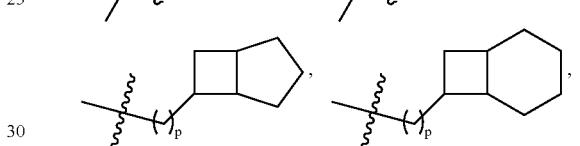
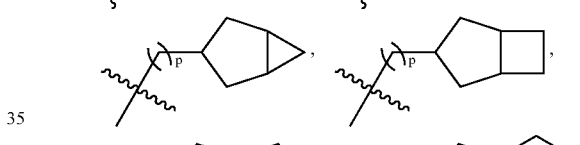
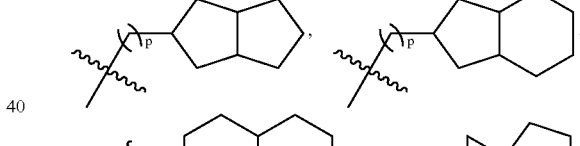
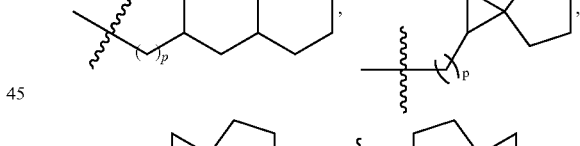
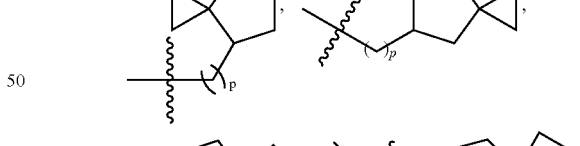
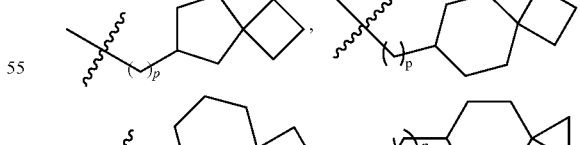
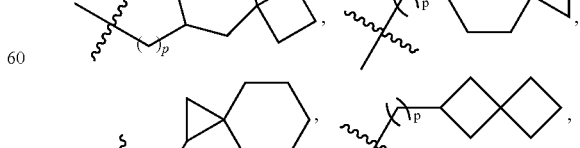
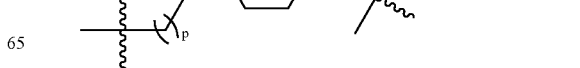

-continued

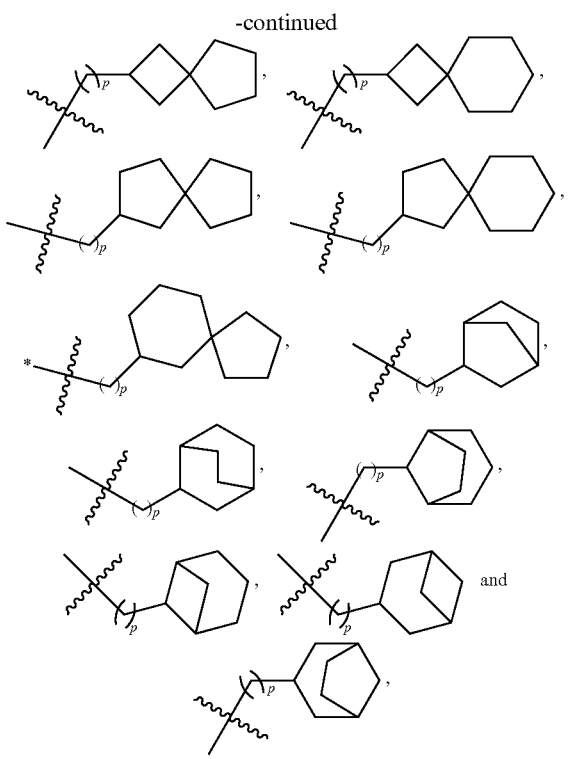

the carbon atom in said ring may be optionally replaced by 1-2 hetero atoms and/or groups that may be identical or different and are selected from the group consisting of O, S(O)$_m$, N(H)$_n$ and/or C(O), provided that an ester structure "—O—C(O)—" is not present in the replaced ring, wherein p is selected from the group consisting of 0, 1 or 2; and when R$^2$ is

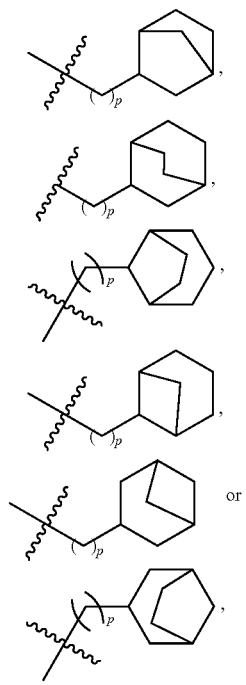

R$^1$ is not methyl, ethyl, propyl, cyclopropyl-C$_{0-3}$alkyl or cyclobutyl-C$_{0-3}$alkyl; and Q$^2$ is selected from the group consisting of halogen, hydroxy, amino, methyl, ethyl, methoxy, ethoxy, methylamino, ethylamino, dimethylamino, diethylamino, acetoxy, acetylamino, methylsulfonyl and methylsulfonylamino;

R$^3$ is selected from the group consisting of halogen, hydroxy, cyano, nitro, trifluoromethyl, carbamoyl, methyl, ethyl, ethenyl, ethynyl, methoxy, methyl substituted with halogen, methoxy substituted with halogen, methylamino, ethylamino, dimethylamino, methylthio, methylcarbamoyl, acetyl, methoxycarbonyl, acetoxy, acetylamino and methylsulfonylamino;

R$^4$, R$^5$ and R$^6$ are each independently selected from the group consisting of hydrogen, halogen, methyl, methoxy, methyl substituted with halogen, methoxy substituted with halogen, methylamino and dimethylamino;

X is a nitrogen atom;

L is O;

T is selected from the group consisting of a covalent bond or CH(R'), R' is hydrogen;

Z is hydrogen;

q is 2, R$^3$ may be identical or different;

m is selected from the group consisting of 0, 1 or 2; and n is selected from the group consisting of 0 or 1.

In a further preferable embodiment, the compound of the general formula (I) according to the present invention has a structure of the following formula (I-1):

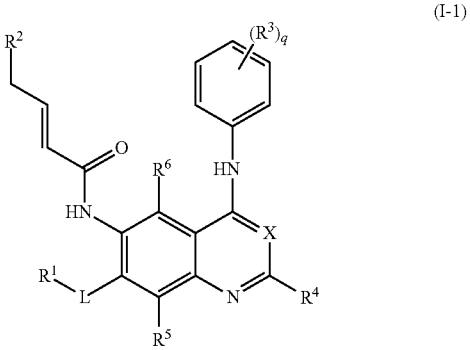

(I-1)

wherein:

R$^1$ is selected from the group consisting of the following groups that are unsubstituted or substituted by halogen, hydroxy, amino, carboxyl, cyano, methyl, ethyl, methoxy, ethoxy, methylamino, ethylamino, dimethylamino, or diethylamino: methyl, ethyl,

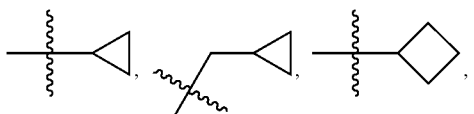

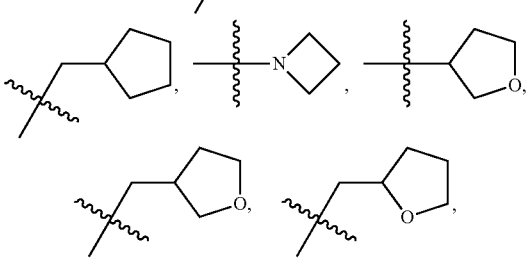

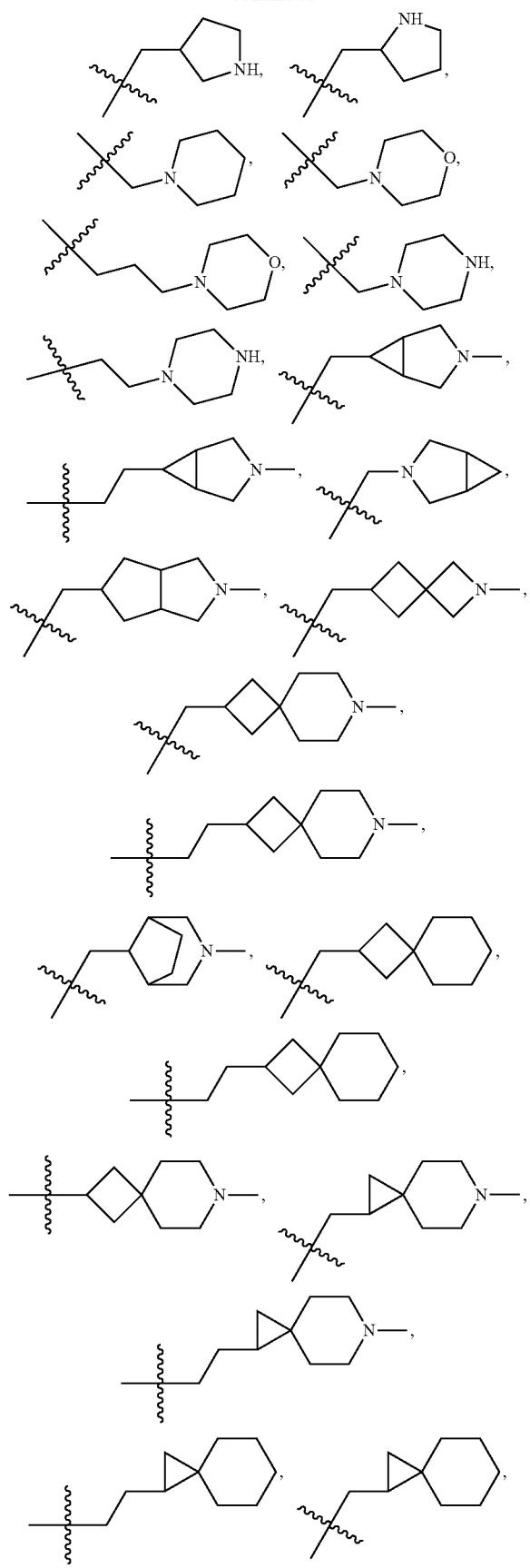
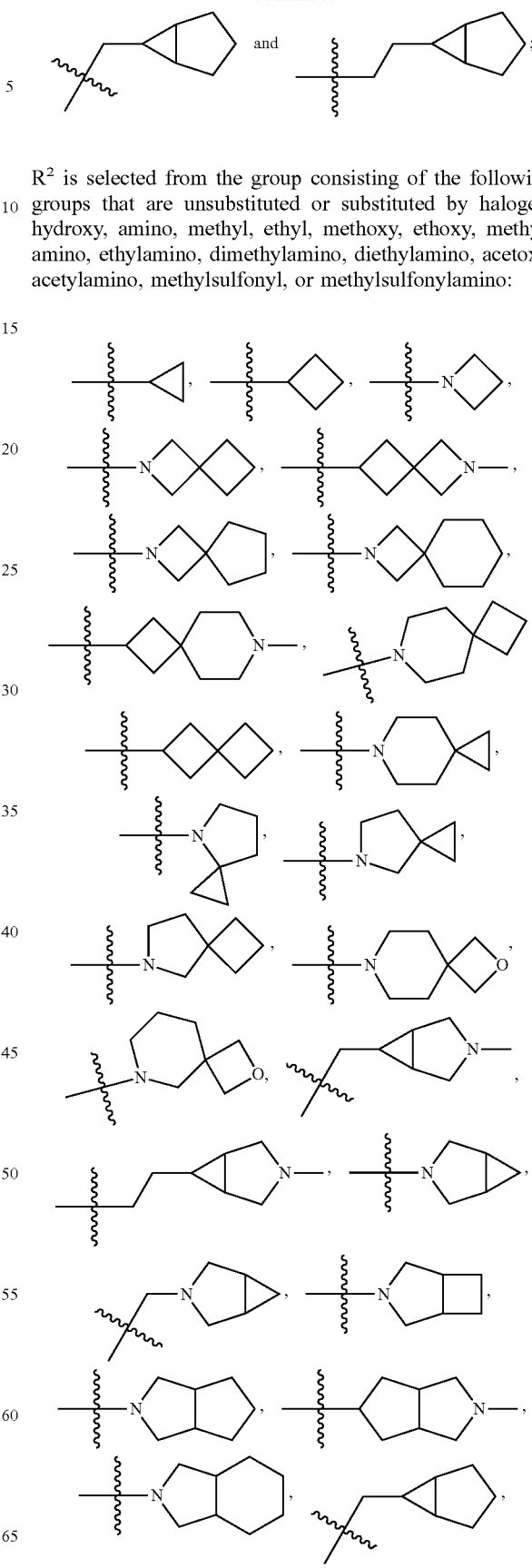
R² is selected from the group consisting of the following groups that are unsubstituted or substituted by halogen, hydroxy, amino, methyl, ethyl, methoxy, ethoxy, methylamino, ethylamino, dimethylamino, diethylamino, acetoxy, acetylamino, methylsulfonyl, or methylsulfonylamino:

-continued

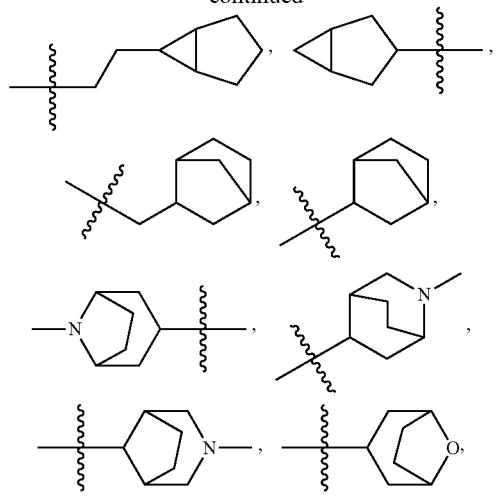

and when R² is

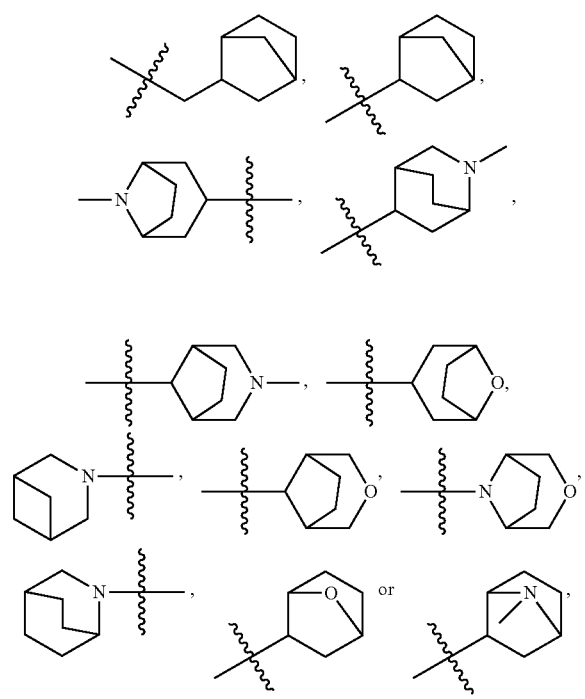

R¹ is not methyl, ethyl,

R³ is halogen, which is selected from the group consisting of fluoro, chloro, bromo, or iodo,
R⁴, R⁵ and R⁶ are each independently hydrogen;
X is a nitrogen atom;
L is O; and
q is 2.

In a further preferable embodiment, the compound of the general formula (I-1) according to the present invention has a structure of the following formula (I-2):

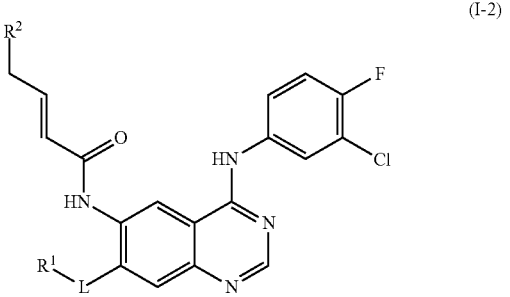

(I-2)

wherein
R¹ is selected from the group consisting of the following groups that are unsubstituted or substituted by halogen, hydroxy, amino, carboxyl, cyano, methyl, ethyl, methoxy, ethoxy, methylamino, ethylamino, dimethylamino, or diethylamino: methyl, ethyl,

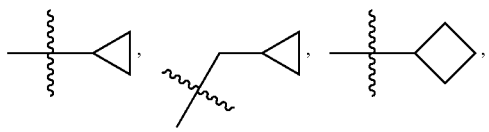
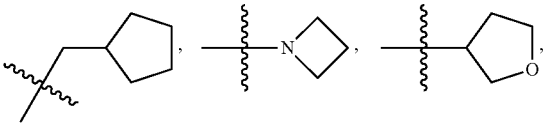
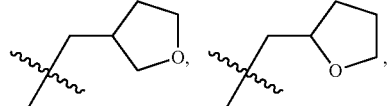
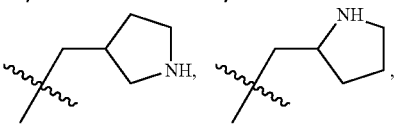
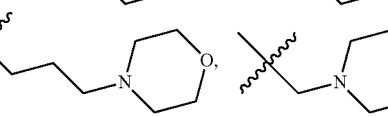

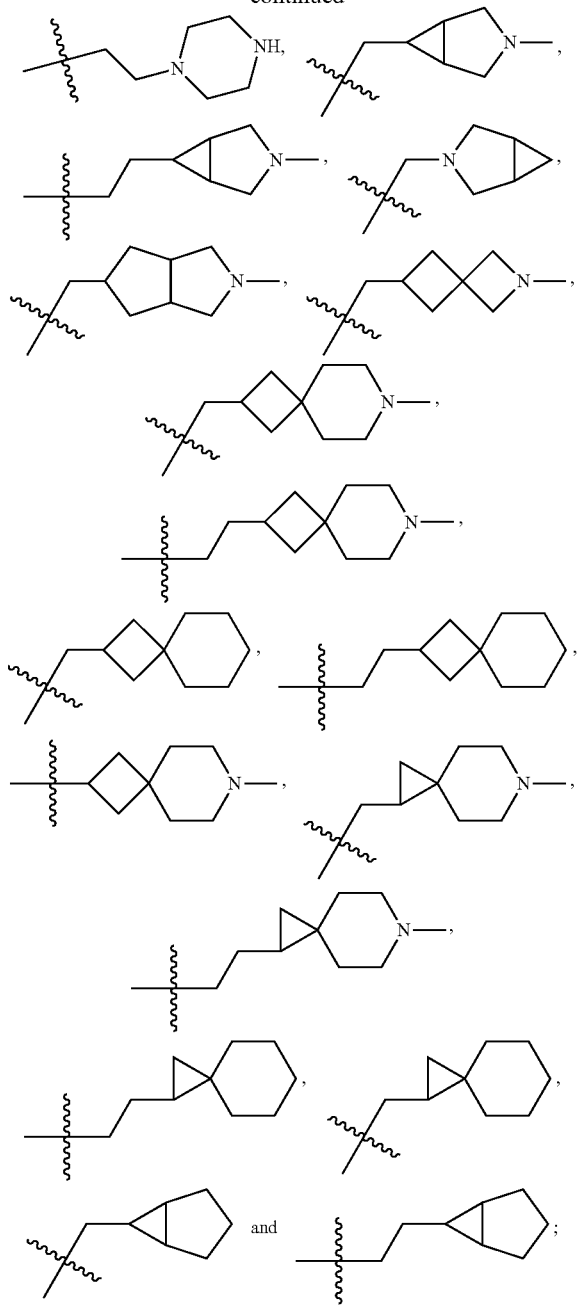
R² is selected from the group consisting of the following groups that are unsubstituted or substituted by halogen, hydroxy, amino, methyl, ethyl, methoxy, ethoxy, methylamino, ethylamino, dimethylamino, diethylamino, acetoxy, acetylamino, methylsulfonyl, or methylsulfonylamino:
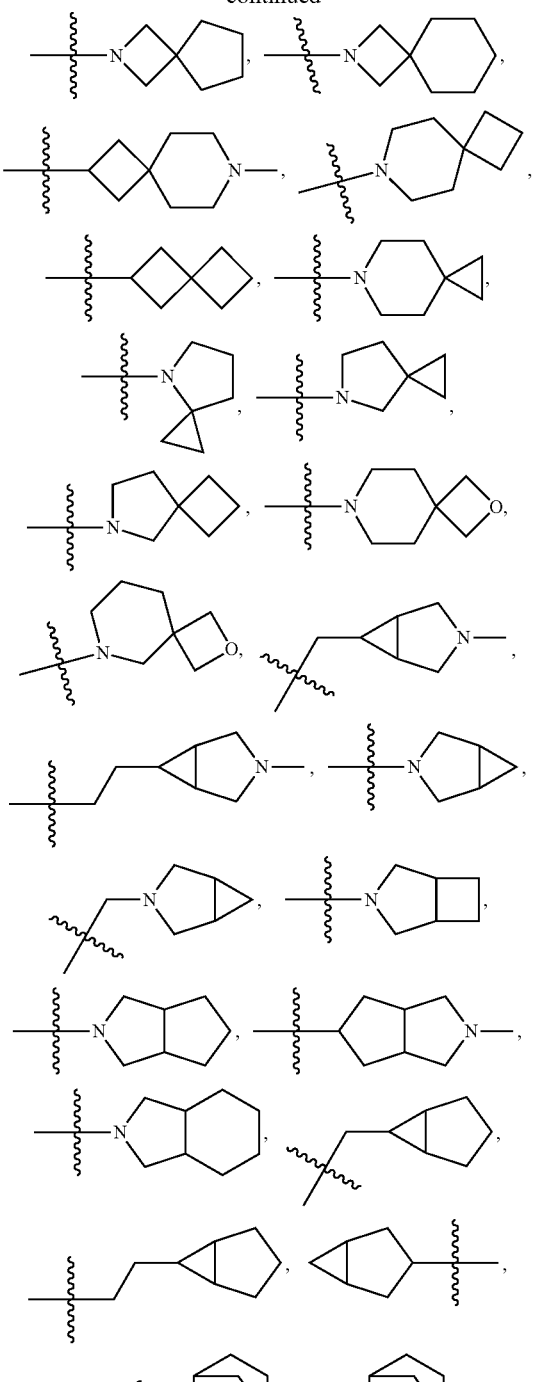
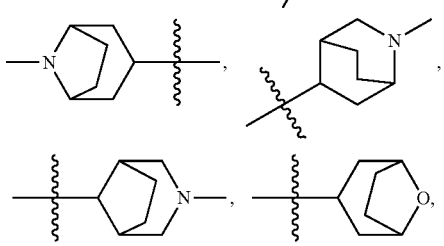

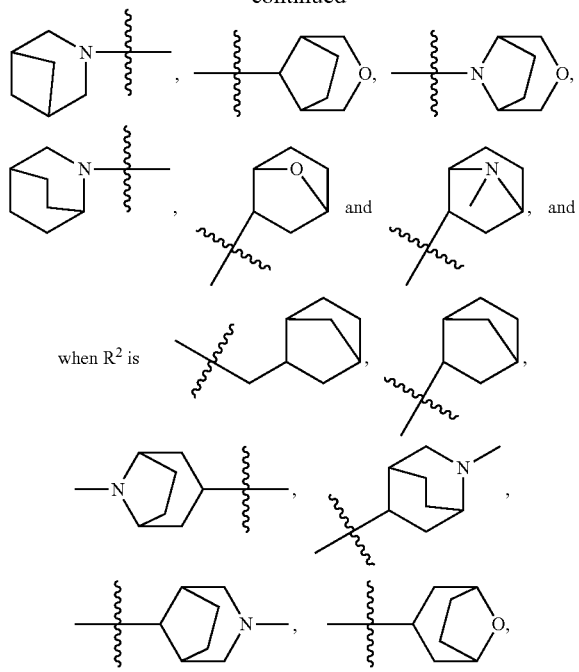
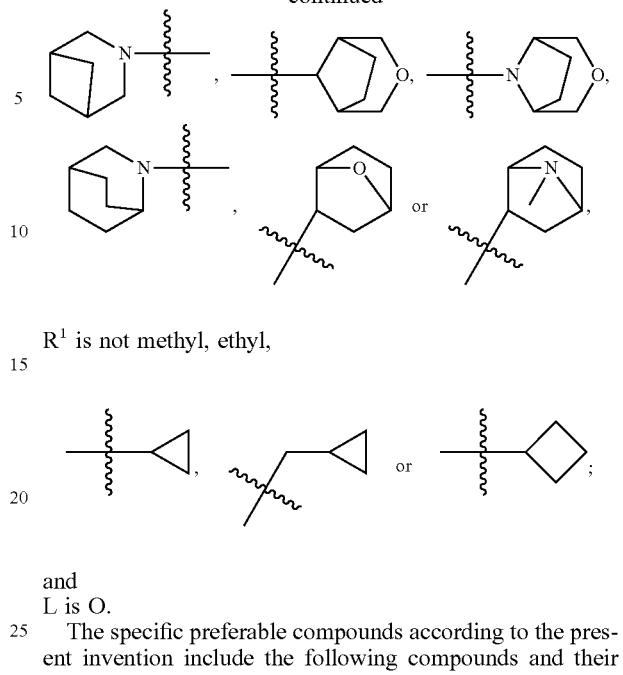

$R^1$ is not methyl, ethyl, and
L is O.

The specific preferable compounds according to the present invention include the following compounds and their pharmaceutically acceptable salts and stereoisomers:

| No. | Structure | Name |
|---|---|---|
| 1 | 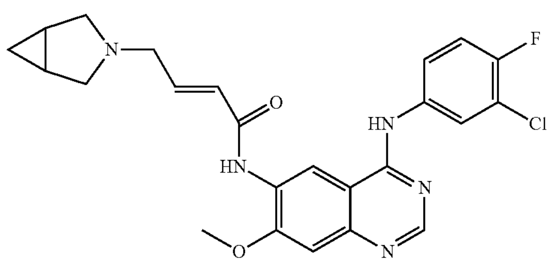 [SMILES: COc1cc2ncnc(Nc3ccc(F)c(Cl)c3)c2cc1NC(=O)/C=C/CN1CC2CC2C1] | (E)-4-[3-azabicyclo[3.1.0]hexan-3-yl]-N-[4-(3-chloro-4-fluorophenylamino)-7-methoxyquinazolin-6-yl]-2-butenamide |
| 2 | 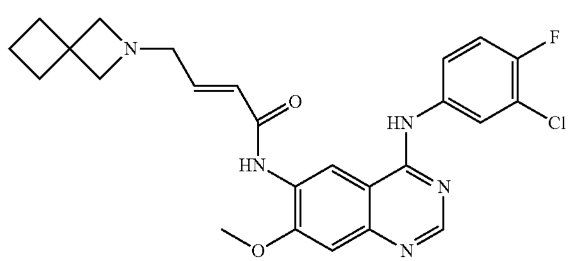 [SMILES: COc1cc2ncnc(Nc3ccc(F)c(Cl)c3)c2cc1NC(=O)/C=C/CN1CC2(CCC2)C1] | (E)-N-[4-(3-chloro-4-fluorophenylamino)-7-methoxyquinazolin-6-yl]-4-[azaspiro[3.3]heptan-2-yl]-2-butenamide |
| 3 | 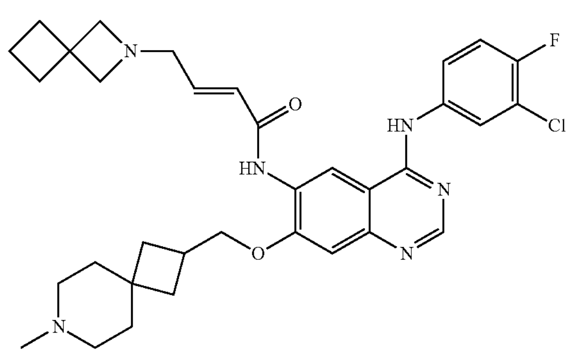 [SMILES: CN1CCC2(CC1)CC(COc1cc3ncnc(Nc4ccc(F)c(Cl)c4)c3cc1NC(=O)/C=C/CN1CC3(CCC3)C1)C2] | (E)-N-[4-(3-chloro-4-fluorophenylamino)-7-[[7-methyl-7-azaspiro[3.5]nonan-2-yl]methoxy]quinazolin-6-yl]-4-[2-azaspiro[3.3]heptan-2-yl]-2-butenamide |

| No. | Structure | Name |
|---|---|---|
| 4 | 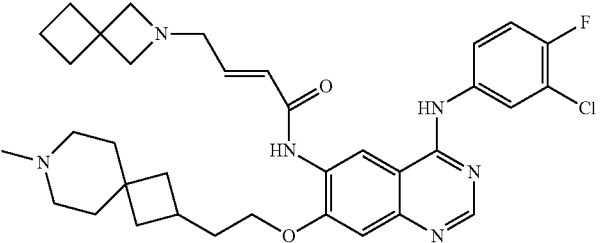 [SMILES: CN1CCC2(CC1)CC(CCOc1cc3ncnc(Nc4ccc(F)c(Cl)c4)c3cc1NC(=O)/C=C/CN1CC3(CCC3)C1)C2] | (E)-N-[4-(3-chloro-4-fluorophenylamino)-7-[2-[7-methyl-7-azaspiro[3.5]nonan-2-yl]ethoxy]quinazolin-6-yl]-4-[2-azaspiro[3.3]heptan-2-yl]-2-butenamide |
| 5 | 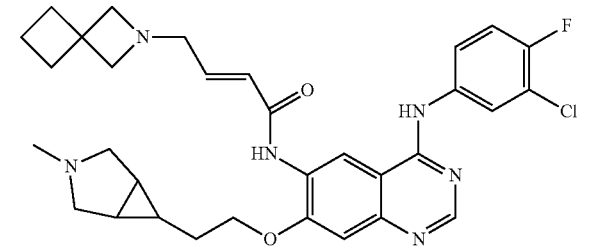 [SMILES: CN1CC2C(CCOc3cc4ncnc(Nc5ccc(F)c(Cl)c5)c4cc3NC(=O)/C=C/CN3CC4(CCC4)C3)C2C1] | (E)-N-[4-(3-chloro-4-fluorophenylamino)-7-[2-[3-methyl-3-azabicyclo[3.1.0]hexan-6-yl]ethoxy]quinazolin-6-yl]-4-[2-azaspiro[3.3]heptan-2-yl]-2-butenamide |
| 6 | 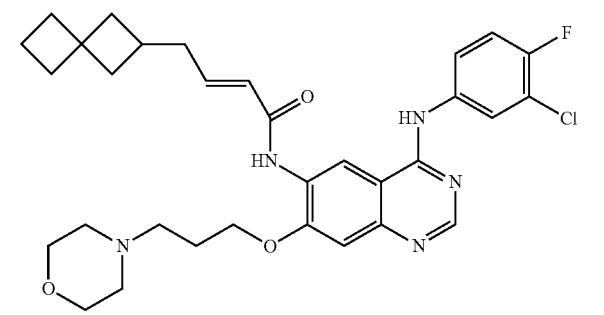 [SMILES: O=C(/C=C/CC1CC2(CCC2)C1)Nc1cc2c(Nc3ccc(F)c(Cl)c3)ncnc2cc1OCCCN1CCOCC1] | (E)-N-[4-(3-chloro-4-fluorophenylamino)-7-(3-morpholinopropoxy)quinazolin-6-yl]-4-[spiro[3.3]heptan-2-yl]-2-butenamide |
| 7 | 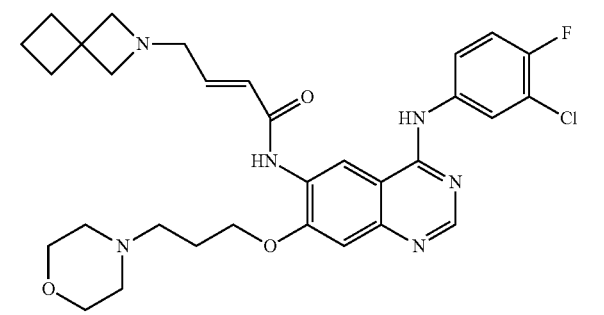 [SMILES: O=C(/C=C/CN1CC2(CCC2)C1)Nc1cc2c(Nc3ccc(F)c(Cl)c3)ncnc2cc1OCCCN1CCOCC1] | (E)-N-[4-(3-chloro-4-fluorophenylamino)-7-[3-morpholinopropoxy]quinazolin-6-yl]-4-[2-azaspiro[3.3]heptan-2-yl]-2-butenamide |
| 8 | 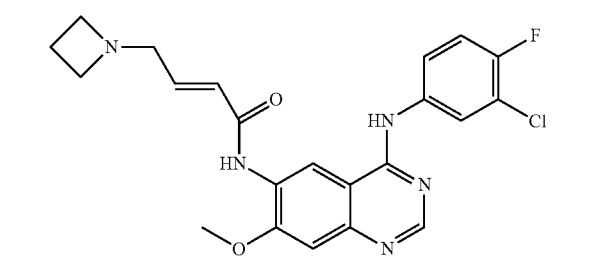 [SMILES: COc1cc2ncnc(Nc3ccc(F)c(Cl)c3)c2cc1NC(=O)/C=C/CN1CCC1] | (E)-4-(azetidin-1-yl)-N-[4-(3-chloro-4-fluorophenylamino)-7-methoxyquinazolin-6-yl]-2-butenamide |

-continued

| No. | Structure | Name |
|---|---|---|
| 9 | 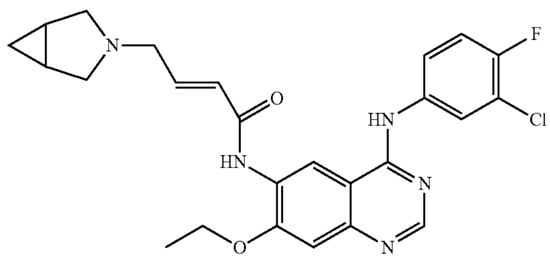 [SMILES: CCOc1cc2ncnc(Nc3ccc(F)c(Cl)c3)c2cc1NC(=O)/C=C/CN1CC2CC2C1] | (E)-4-[3-azabicyclo[3.1.0]hexan-3-yl]-N-[4-(3-chloro-4-fluorophenylamino)-7-ethoxyquinazolin-6-yl]-2-butenamide |
| 10 | 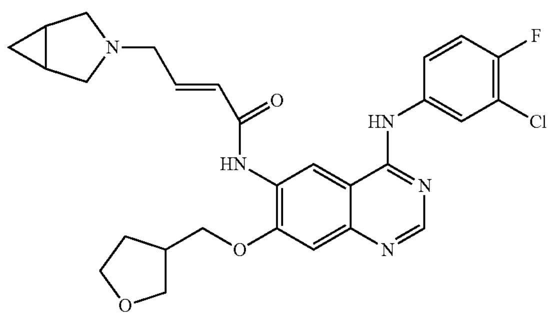 [SMILES: O=C(/C=C/CN1CC2CC2C1)Nc1cc2c(Nc3ccc(F)c(Cl)c3)ncnc2cc1OCC1CCOC1] | (E)-4-[3-azabicyclo[3.1.0]hexan-3-yl]-N-[4-(3-chloro-4-fluorophenylamino)-7-[(tetrahydrofuran-3-yl)methoxy]quinazolin-6-yl]-2-butenamide |
| 11 | 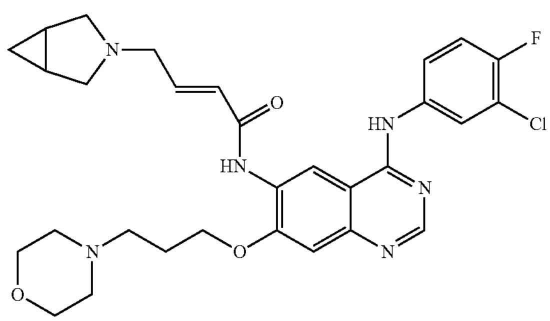 [SMILES: O=C(/C=C/CN1CC2CC2C1)Nc1cc2c(Nc3ccc(F)c(Cl)c3)ncnc2cc1OCCCN1CCOCC1] | (E)-4-[3-azabicyclo[3.1.0]hexan-3-yl]-N-[4-(3-chloro-4-fluorophenylamino)-7-(3-morpholinopropoxy)quinazolin-6-yl]-2-butenamide |
| 12 | 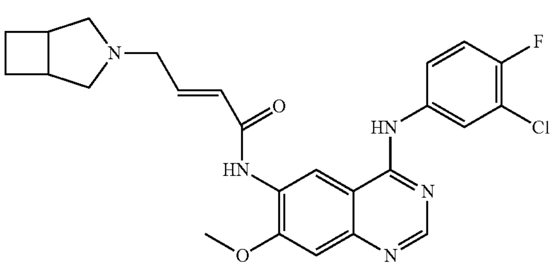 [SMILES: COc1cc2ncnc(Nc3ccc(F)c(Cl)c3)c2cc1NC(=O)/C=C/CN1CC2CCC2C1] | (E)-4-(3-azabicyclo[3.2.0]heptan-3-yl)-N-[4-(3-chloro-4-fluorophenylamino)-7-methoxyquinazolin-6-yl]-2-butenamide |
| 13 | 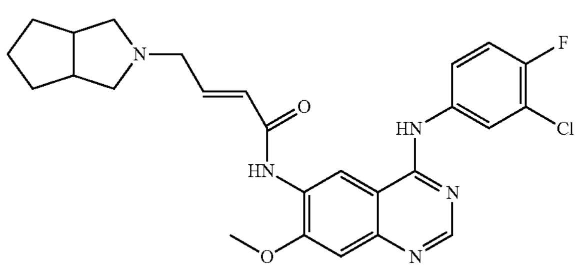 [SMILES: COc1cc2ncnc(Nc3ccc(F)c(Cl)c3)c2cc1NC(=O)/C=C/CN1CC2CCCC2C1] | (E)-N-[4-(3-chloro-4-fluorophenylamino)-7-methoxyquinazolin-6-yl]-4-[hexahydro-cyclopenta[c]pyrrol-2(1H)-yl]-2-butenamide |

| No. | Structure | Name |
|---|---|---|
| 14 | 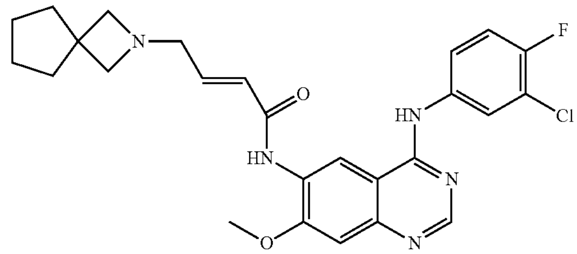 [SMILES: COc1cc2ncnc(Nc3ccc(F)c(Cl)c3)c2cc1NC(=O)/C=C/CN1CC2(CCCC2)C1] | (E)-N-[4-(3-chloro-4-fluorophenylamino)-7-methoxyquinazolin-6-yl]-4-[2-azaspiro[3.4]octan-2-yl]-2-butenamide |
| 15 | 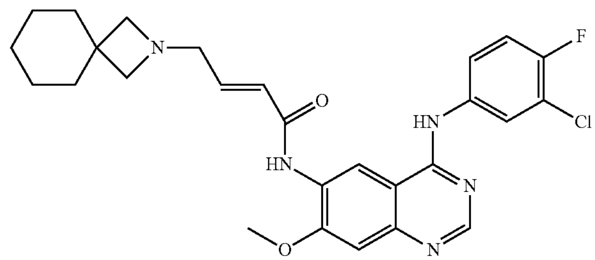 [SMILES: COc1cc2ncnc(Nc3ccc(F)c(Cl)c3)c2cc1NC(=O)/C=C/CN1CC2(CCCCC2)C1] | (E)-N-[4-(3-chloro-4-fluorophenylamino)-7-methoxyquinazolin-6-yl]-4-[2-azaspiro[3.5]nonan-2-yl]-2-butenamide |
| 16 | 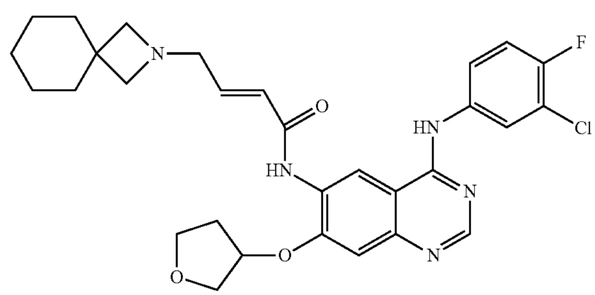 [SMILES: O=C(/C=C/CN1CC2(CCCCC2)C1)Nc1cc2c(Nc3ccc(F)c(Cl)c3)ncnc2cc1OC1CCOC1] | (E)-N-[4-(3-chloro-4-fluorophenylamino)-7-(tetrahydrofuran-3-yloxy)quinazolin-6-yl]-4-[2-azaspiro[3.5]nonan-2-yl]-2-butenamide |
| 17 | 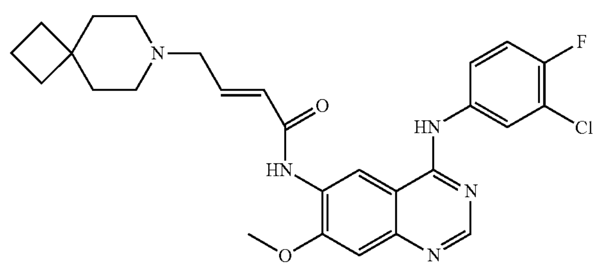 [SMILES: COc1cc2ncnc(Nc3ccc(F)c(Cl)c3)c2cc1NC(=O)/C=C/CN1CCC2(CCC2)CC1] | (E)-N-[4-(3-chloro-4-fluorophenylamino)-7-methoxyquinazolin-6-yl]-4-[7-azaspiro[3.5]nonan-7-yl]-2-butenamide |
| 18 | 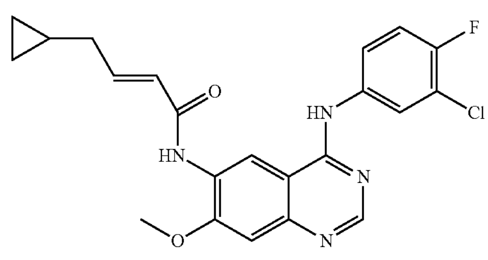 [SMILES: COc1cc2ncnc(Nc3ccc(F)c(Cl)c3)c2cc1NC(=O)/C=C/CC1CC1] | (E)-N-[4-(3-chloro-4-fluorophenylamino)-7-methoxyquinazolin-6-yl]-4-cyclopropyl-2-butenamide |
| 19 | 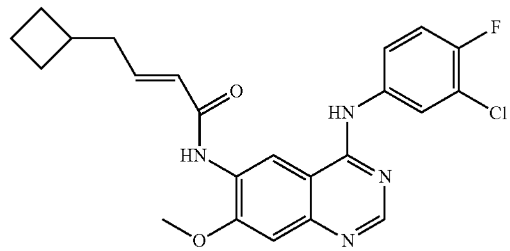 [SMILES: COc1cc2ncnc(Nc3ccc(F)c(Cl)c3)c2cc1NC(=O)/C=C/CC1CCC1] | (E)-N-[4-(3-chloro-4-fluorophenylamino)-7-methoxyquinazolin-6-yl]-4-cyclobutyl-2-butenamide |

| No. | Structure | Name |
|---|---|---|
| 20 | 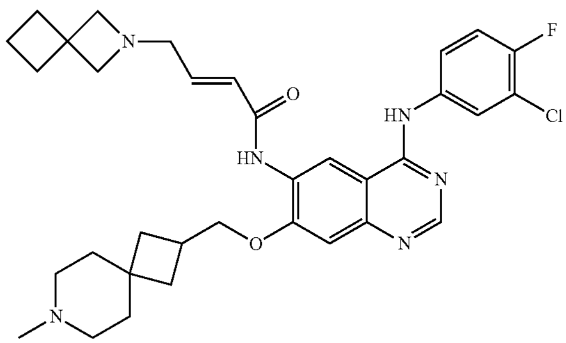 [SMILES: CN1CCC2(CC1)CC(COc1cc3ncnc(Nc4ccc(F)c(Cl)c4)c3cc1NC(=O)/C=C/CN1CC3(CCC3)C1)C2] | (E)-N-[4-(3-chloro-4-fluorophenylamino)-7-[[7-methyl-7-azaspiro[3.5]nonan-2-yl]methoxy]quinazolin-6-yl]-4-[2-azaspiro[3.3]heptan-2-yl]-2-butenamide |
| 21 | 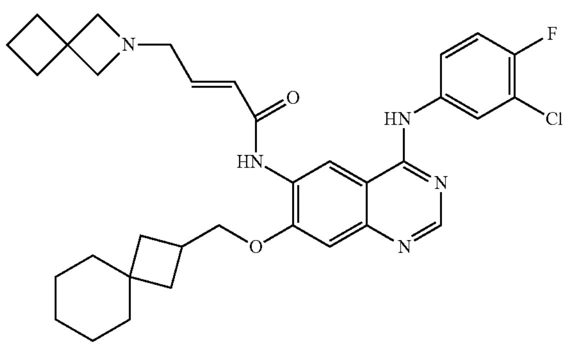 [SMILES: O=C(/C=C/CN1CC2(CCC2)C1)Nc1cc2c(Nc3ccc(F)c(Cl)c3)ncnc2cc1OCC1CC2(CCCCC2)C1] | (E)-N-[4-(3-chloro-4-fluorophenylamino)-7-[spiro[3.5]nonan-2-ylmethoxy]quinazolin-6-yl]-4-[2-azaspiro[3.3]heptan-2-yl]-2-butenamide |
| 22 | 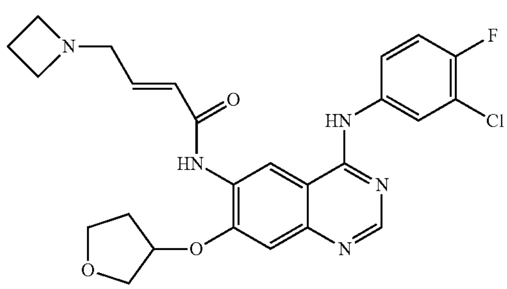 [SMILES: O=C(/C=C/CN1CCC1)Nc1cc2c(Nc3ccc(F)c(Cl)c3)ncnc2cc1OC1CCOC1] | (E)-4-(azetidin-1-yl)-N-[4-(3-chloro-4-fluorophenylamino)-7-(tetrahydrofuran-3-yloxy)quinazolin-6-yl]-2-butenamide |
| 23 | 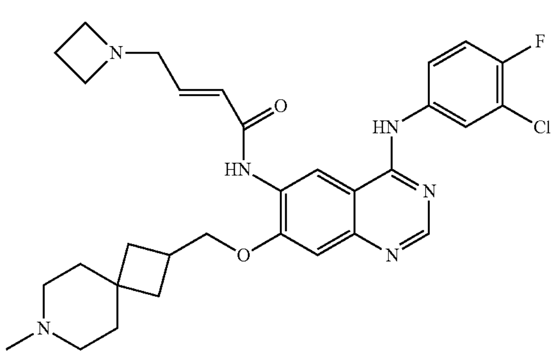 [SMILES: CN1CCC2(CC1)CC(COc1cc3ncnc(Nc4ccc(F)c(Cl)c4)c3cc1NC(=O)/C=C/CN1CCC1)C2] | (E)-4-(azetidin-1-yl)-N-[4-(3-chloro-4-fluorophenylamino)-7-[[7-methyl-7-azaspiro[3.5]nonan-2-yl]methoxy)quinazolin-6-yl]-2-butenamide |

-continued

| No. | Structure | Name |
|---|---|---|
| 24 | 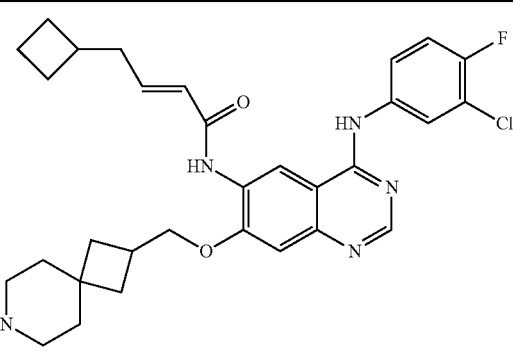 | (E)-N-[4-(3-chloro-4-fluorophenylamino)-7-[[7-methyl-7-azaspiro[3.5]nonan-2-yl]methoxy]quinazolin-6-yl]-4-cyclobutyl-2-butenamide |
| 25 | 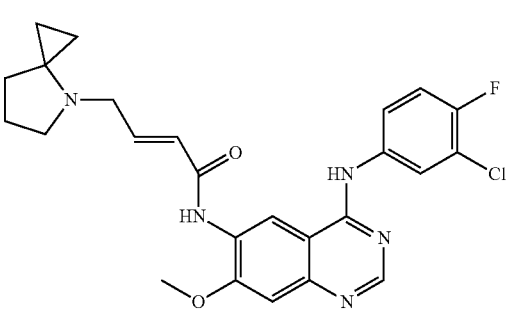 [SMILES: COc1cc2ncnc(Nc3ccc(F)c(Cl)c3)c2cc1NC(=O)/C=C/CN1CCCC12CC2] | (E)-N-[4-(3-chloro-4-fluorophenylamino)-7-methoxyquinazolin-6-yl]-4-[4-azaspiro[2.4]heptan-4-yl]-2-butenamide |
| 26 | 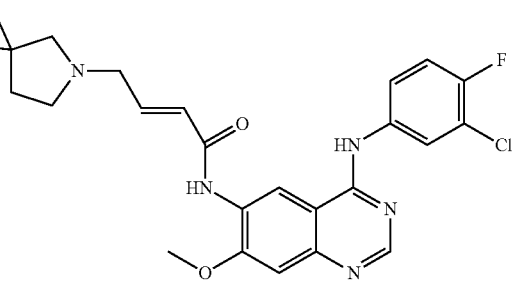 | (E)-N-[4-(3-chloro-4-fluorophenylamino)-7-methoxyquinazolin-6-yl]-4-[5-azaspiro[2.4]heptan-5-yl]-2-butenamide |
| 27 | 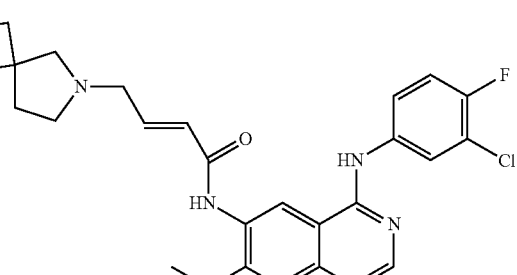 | (E)-N-[4-(3-chloro-4-fluorophenylamino)-7-methoxyquinazolin-6-yl]-4-[6-azaspiro[3.4]octan-6-yl]-2-butenamide |
| 28 | 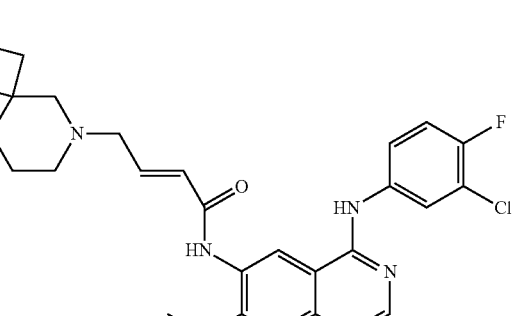 | (E)-N-[4-(3-chloro-4-fluorophenylamino)-7-methoxyquinazolin-6-yl]-4-[2-oxa-6-azaspiro[3.5]nonan-6-yl]-2-butenamide |

| No. | Structure | Name |
|---|---|---|
| 29 | 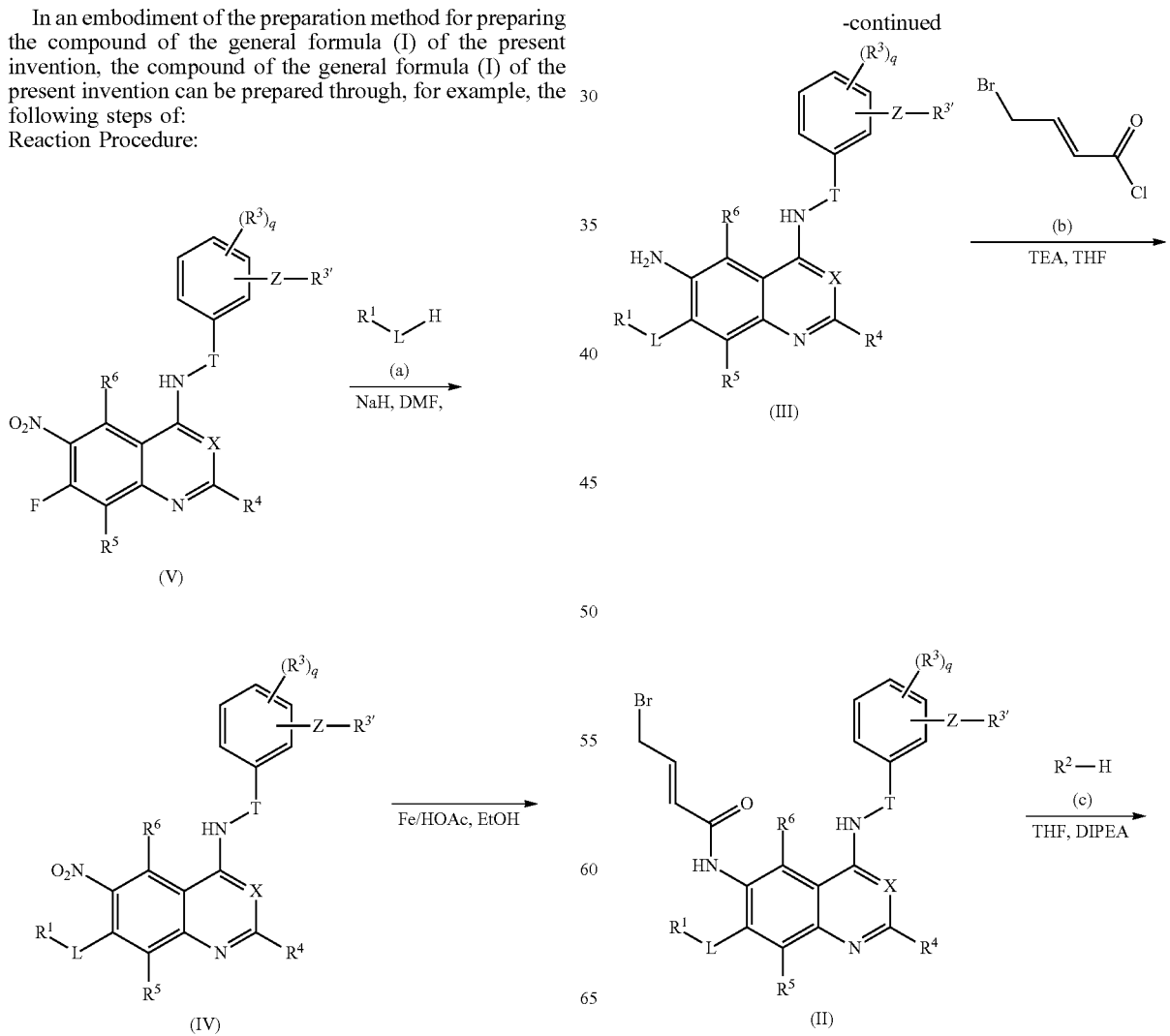 | (E)-N-[4-(3-chloro-4-fluorophenylamino)-7-methoxyquinazolin-6-yl]-4-[2-oxa-7-azaspiro[3.5]nonan-7-yl]-2-butenamide |
| 30 | 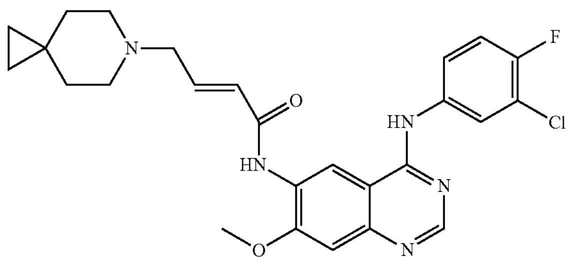 [SMILES: COc1cc2ncnc(Nc3ccc(F)c(Cl)c3)c2cc1NC(=O)/C=C/CN1CCC2(CC1)CC2] | (E)-N-[4-(3-chloro-4-fluorophenylamino)-7-methoxyquinazolin-6-yl]-4-[6-azaspiro[2.5]octan-6-yl]-2-butenamide |

In an embodiment of the preparation method for preparing the compound of the general formula (I) of the present invention, the compound of the general formula (I) of the present invention can be prepared through, for example, the following steps of:

Reaction Procedure:

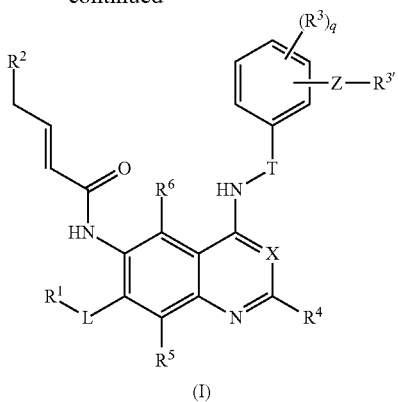

(I)

wherein $R^1$, $R^2$, $R^3$, $R^{3'}$, $R^4$, $R^5$, $R^6$, X, L, T, Z and q are defined as above, and Br in formula (b) may be replaced with Cl or I, and Cl can also be replaced with Br;

Step 1: The Preparation of a Compound of the Formula (IV)

A compound of the formula (V) is dissolved an organic solvent (such as DMF, THF, acetonitrile, methanol or ethanol). To the mixture is added an inorganic base (such as NaH, NaOH or KOH) in batch. The resulting mixture is reacted under stirring at room temperature. Then a compound of formula (a) is added to the reaction mixture. The resulting mixture is reacted under heating to reflux for hours to produce a compound of the formula (IV).

Step 2: The Preparation of a Compound of the Formula (III)

A compound of the formula (IV) is added in batch to a mixed solution of a polar organic solvent (such as ethanol, methanol or THF) and an acid (such as acetic acid, formic acid, hydrochloric acid or dilute sulfuric acid). To the resulting mixture is then added a reducing agent (such as Fe powder, Zn powder, Pd/C or Raney Ni). The mixture is reacted under heating to produce a compound of the formula (III).

Step 3: The Preparation of a Compound of the Formula (II)

A compound of the formula (III) is dissolved in an organic solvent (such as THF, DCM or EA). To the resulting mixture is added a compound of the formula (b) under cooling in an ice-water bath, and then is added dropwise an organic base (such as triethylamine or DIPEA). The mixture is reacted under stirring to produce a compound of the formula (II).

Step 4: The Preparation of a Compound of the Formula (I)

A compound of the formula (II) is dissolved in an organic solvent (such as THF, DCM, DMF or acetonitrile). To the resulting mixture is successively added a base (such as DIPEA, TEA, pyridine, $K_2CO_3$ or $Na_2CO_3$) and a compound of the formula (c). The mixture is reacted under stirring at room temperature to produce a compound of the formula (I).

Where if necessary, a functional group that needs to be protected, e.g. hydroxy, amino and the like, may be protected, and then deprotected according to the conventional method.

The present invention also comprises "a pharmaceutically acceptable salt" of the compound of the formula (I). The pharmaceutically acceptable salt of the compound of the formula (I) of the present invention comprises alkali metal salts, such as Na salt, K salt, Li salt and the like; alkaline-earth metal salts, such as Ca salt, Mg salt and the like; other metal salts, such as Al salt, Fe salt, Zn salt, Cu salt, Ni salt, Co salt and the like; inorganic base salts, such as ammonium salt; organic base salts, such as tert-octylamine salt, dibenzylamine salt, morpholine salt, glucosamine salt, alkyl phenylglycinate salt, ethylene diamine salt, N-methylglucosamine salt, guanidine salt, diethylamine salt, triethylamine salt, dicyclohexyl amine salt, N,N'-dibenzylethylene diamine salt, chloroprocaine salt, procaine salt, diethanol amine salt, N-benzyl-phenylethyl amine salt, piperazine salt, tetramethyl amine salt, tris(hydroxymethyl) aminomethane salt and the like; inorganic acid salts, such as halogen acid salt, such as hydrofluoric acid salt, hydrochloride, hydrobromide, hydriodate and the like, nitrate, perchlorate, sulfate, phosphate and the like; organic acid salts, such as lower alkanesulfonate, e.g. mesylate, trifluoromesylate, ethanesulfonate and the like, arylsulfonate, such as benzenesulfonate, para-benzenesulfonate and the like, carboxylate, such as acetate, malate, fumarate, succinate, citrate, tartrate, oxalate, maleate and the like, amino acid salts, such as glycine salt, trimethylglycinate salt, arginine salt, ornithine salt, glutamate salt, aspartate salt and the like.

The present invention also comprises all of possible isomers of the compound of the formula (I). The enantiomorph can be present in case that one or more asymmetric carbon atoms are present in the compound structure; the cis/trans-isomer can be present in case that the compound contains an alkenyl group or a cyclic structure; and the tautomer can be present in case that the compound contains a keto group or a nitrosyl group. All of these isomers and the mixtures thereof are in the scope of the present invention.

The compound of the general formula (I) of the present invention and a pharmaceutically acceptable salt and a stereoisomer thereof can be administered to a mammal, e.g. human orally, parenterally (intravenously, intramuscularly, subcutaneously or rectally and the like), pulmonarily, and locally. The daily dosage of the present compound can be about 1 to about 1000 mg.

The compound of the general formula (I) of the present invention or a pharmaceutically acceptable salt or a stereoisomer thereof can be administered alone or in combination with other therapeutical agents, in particular a second therapeutical agent selected from the group consisting of an antineoplastic agent and an immunosuppressive agent. Said second therapeutical agent is selected from the group consisting of antimetabolite, including but not limited to e.g. capecitabine, gemcitabine and the like; a growth factor inhibitor, including but not limited to e.g. pazopanib, imatinib and the like; an antibody, including but not limited to e.g. herceptin, bevacizumab and the like; a mitotic inhibitor, including but not limited to e.g. paclitaxel, vinorelbine, docetaxel, doxorubicin and the like; antineoplastic hormone, including but not limited to e.g. letrozole, tamoxifen, fulvestrant and the like; alkylating agent, including but not limited to e.g. cyclophosphamide, carmustine and the like; a metal platinum, including but not limited to e.g. carboplatin, cisplatin, oxaliplatin and the like; a topoisomerase inhibitor, including but not limited to e.g. topotecan and the like; an immunosuppressant, including but not limited to e.g. everolimus and the like. All of components to be administered can be administered at the same time or successively and separately in a form of the single formulation or in a combination of the divided formulations.

The present compound of formula (I), a pharmaceutically acceptable salt thereof or a stereoisomer thereof can be used to treat an excessive proliferative disease and a chronic obstructive pulmonary disease. The excessive proliferative disease includes cancerous disease and non-cancerous disease. The cancerous disease is selected from the group consisting of cerebroma, lung cancer, non-small cell lung cancer, squamous cell, bladder carcinoma, gastric cancer, ovarian cancer, peritoneal cancer, pancreatic cancer, mammary cancer, head and neck cancer, cervical cancer, endometrial cancer, colorectal cancer, liver cancer, renal carcinoma, adenocarcinoma of esophagus, esophageal squamous cell cancer, solid tumor, non-Hodgkin lymphoma, central nervous system tumor (glioma, gliobastona multiforme, glioma sarcomatosis), prostate carcinoma or thyroid carcinoma; the non-cancerous disease includes for example benign proliferative diseases of skin or prostate.

The present invention also provides a pharmaceutical composition, containing the compound of the general formula (I) of the present invention, a pharmaceutically acceptable salt, or a stereoisomer thereof as described above and one or more pharmaceutically acceptable carriers. Said composition can be prepared by mixing the compound of the general formula (I) of the present invention or a pharmaceutically acceptable salt, or a stereoisomer thereof and one or more conventional pharmaceutically acceptable carrier. Said composition can be prepared into a conventional clinically or pharmaceutically acceptable dosage form to administer orally, parenterally, pulmonarily or locally to the patient in need thereof.

For the oral administration, The compound of the general formula (I) of the present invention or a pharmaceutically acceptable salt, or a stereoisomer thereof can be formulated into a conventional solid preparation, such as tablet, granule, capsule, powder and the like; or the oral liquid preparation, such as an oral solution, an oral suspension, a syrup and the like. For preparing the oral preparation, suitable filler, binder, disintegrant, lubricant, diluent and the like can be added. Conventional filler includes starch, sugar powder, calcium phosphate, calcium sulfate dihydrate, dextrin, microcrystalline cellulose, lactose, pregelatinized starch, mannitol and the like. Conventional binder includes sodium carboxymethylcellulose, PVP-K30, hydroxypropyl cellulose, starch paste, methyl cellulose, ethyl cellulose, hypromellose, gelatinized starch and the like. Conventional disintegrant includes dry starch, polyvinylpolypyrrolidone (cPVP), croscarmellose sodium, sodium carboxymethyl starch, low-substituted hydroxypropyl cellulose and the like. Conventional lubricant includes magnesium stearate, talc powder, sodium dodecylsulfate, Silica powder and the like. Conventional diluent includes water, ethanol, glycerin and the like.

For the parenteral administration, according to the conventional method, The compound of the general formula (I) of the present invention or a pharmaceutically acceptable salt, or a stereoisomer thereof can be formulated into an injectable preparation, including an injection solution, a sterile injection powder and a concentrated injection solution. For preparing the injectable preparation, a conventional method in the pharmaceutical production can be used, and an aqueous solvent or a nonaqueous solvent can be used. The most commonly used aqueous solvent is water for injection. 0.9% aqueous NaCl solution or other suitable aqueous solution can also be used. The most commonly used non-aqueous solvent is vegetable oil, such as soy oil for injection. The aqueous solution of ethanol, propylene glycol, polyethylene glycol or the like can also be used. For preparing the injectable preparation, an additive can be optionally added, depending on the nature of drug. The additive includes an osmotic regulator, a pH-value regulator, a solubilizer, a filler, an antioxidant, a bacteriostatic agent, an emulsifier, a suspending agent or the like. For the rectal, pulmonary or local administration, The compound of the general formula (I) of the present invention or a pharmaceutically acceptable salt, or a stereoisomer thereof can be formulated into an inhalant, a sublingual formulation, a gel, an ointment, a suppository, a lotion, a nasal drop, a spraying agent, a transdermal patch and the like according to the conventional method.

It is demonstrated that the compound of the present invention is a tyrosine kinase inhibitor and has an excellent antineoplastic effect. The compound of the present invention therefore has a good therapeutic effect on an excessive proliferative disease and a chronic obstructive pulmonary disease and reduces the formation of drug resistance. In addition, it is easy to prepare the compound of the present invention; the compound of the present invention has a stable quality, and therefore the compound of the present invention is apt to be produced on the industrial scale.

BEST MODE OF CARRYING OUT THE INVENTION

The following examples are intended to illustrate the invention and are not to be construed as being limitations thereon. All of the technical solutions that can be accomplished based on the above disclosure fall in the scope of the present invention.

I. The Preparation Example for the Compound of the Present Invention

Example 1

The preparation of (E)-4-[3-azabicyclo[3.1.0]hexan-3-yl]-N-[4-(3-chloro-4-fluorophenylamino)-7-methoxyquinazolin-6-yl]-2-butenamide (Compound 1) hydrochloride (1) The preparation of 4-(3-chloro-4-fluorophenylamino)-6-nitro-7-methoxyquinazoline

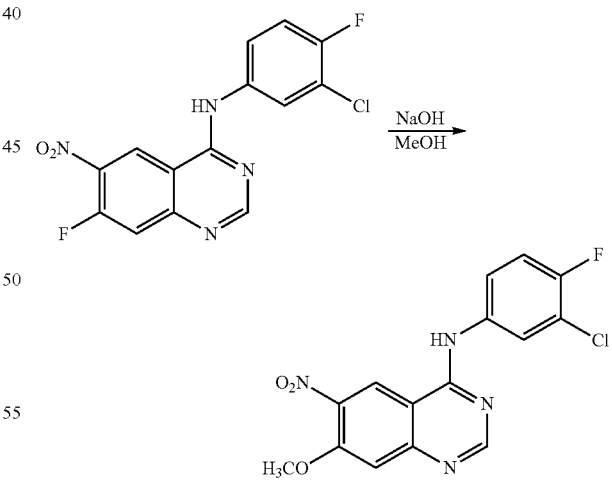

4-(3-chloro-4-fluorophenyl)amino-6-nitro-7-fluoroquinazoline (25.4 g, 75.4 mmol) and a 50% NaOH solution (7.85 mL, 98.125 mmol) were added to 500 mL methanol. The resulting mixture was reacted at 70° C. under reflux for 2 h. The reaction liquor was poured into ice-water. A large amount of solid separated. After filtering, the filter cake was dried to produce 25.3 g of the target product as yellow solid in a yield of 96.4%.

(2) The preparation of 4-(3-chloro-4-fluorophenyl)amino-6-amino-7-methoxyquinazoline

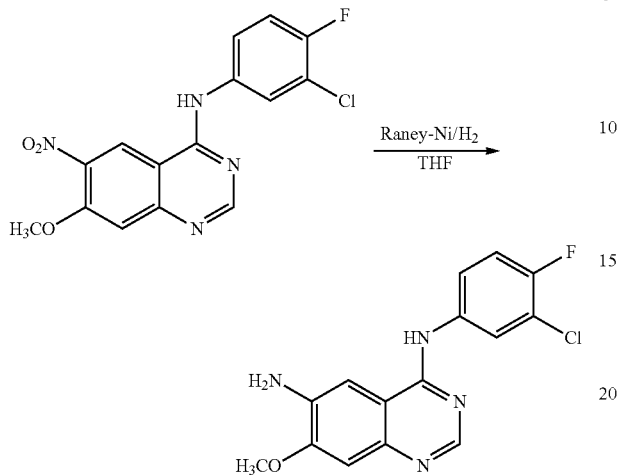

4-(3-chloro-4-fluorophenylamino)-6-nitro-7-methoxyquinazoline (25.3 g, 72.7 mmol) was dissolved in 500 mL tetrahydrofuran. To the solution was added 7.6 g Raney-Ni. To the resulting mixture was added hydrogen gas. The mixture was stirred at room temperature for 24 h, filtered and rotary-evaporated to remove the solvent. The resulting residue was washed with ethyl acetate to produce 13.345 g 4-(3-chloro-4-fluorophenyl)amino-6-amino-7-methoxyquinazoline as yellow solid in a yield of 57.7%.

$^1$H-NMR (DMSO-$d_6$, 400 MHz): δ10.17 (s, 1H), 9.22 (s, 1H), 8.68 (s, 1H), 8.15 (d, J=4.8 Hz, 1H), 7.78 (br. s., 1H), 7.35-7.55 (m, 2H), 4.05 (s, 3H).

(3) The preparation of (E)-4-bromo-N-[4-(3-chloro-4-fluorophenylamino)-7-methoxyquinazolin-6-yl]-2-butenamide

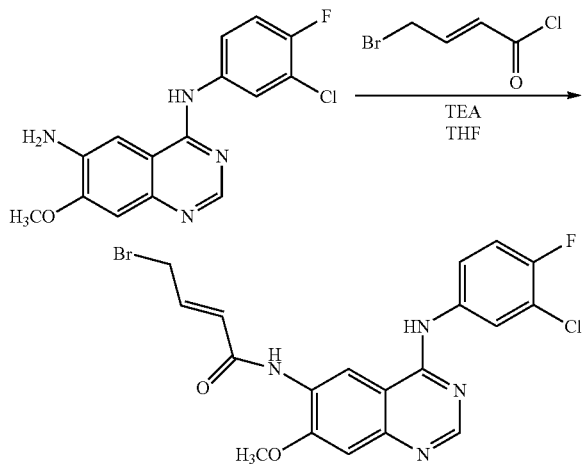

In a dried reaction bottle, 4-(3-chloro-4-fluorophenyl)amino-6-amino-7-methoxyquinazoline (0.567 g, 1.778 mmol) and triethylamine (0.61 mL, 4.387 mmol) were dissolved in dissolved in 20 mL tetrahydrofuran. To the reaction bottom was added dropwise at 0° C. (E)-4-bromo-2-crotonyl chloride (0.555 g, 3.023 mmol). The resulting mixture was stirred for 1 h with maintaining the temperature. To the reaction liquor was added an appropriate amount of water. The mixture was extracted with dichlormethane. The organic phases were combined, washed with brine, dried over anhydrous sodium sulfate, filtered, and concentrated to produce (E)-4-bromo-N-[4-(3-chloro-4-fluorophenylamino)-7-methoxyquinazolin-6-yl]-2-butenamide (0.742 g in a yield of 89.6%) as yellow solid.

(4) The preparation of (E)-4-[3-azabicyclo[3.1.0]hexan-3-yl]-N-[4-(3-chloro-4-fluorophenylamino)-7-methoxyquinazolin-6-yl]-2-butenamide (Compound 1) hydrochloride

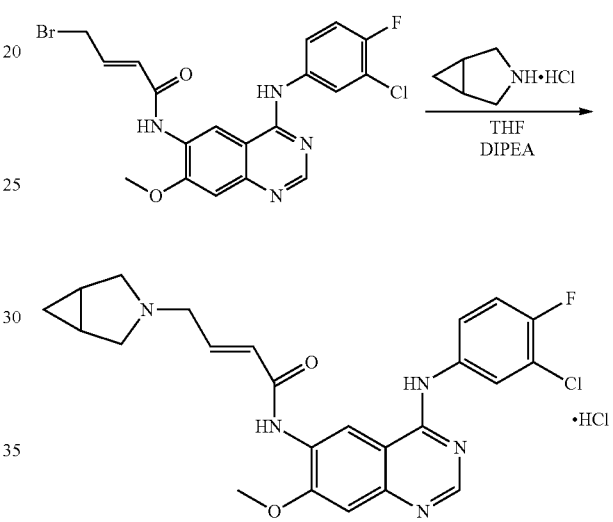

(E)-4-bromo-N-[4-(3-chloro-4-fluorophenylamino)-7-methoxyquinazolin-6-yl]-2-butenamide (600 mg, 1.29 mmol) was dissolved in 20 mL THF. To the resulting mixture was added 3-azabicyclo[3.1.0]hexane hydrochloride (200 mg, 1.69 mmol), and then added dropwise 1 mL DIPEA slowly. The mixture was reacted under heating to reflux for 12 h. The reaction mixture was concentrated. To the resulting condensate was added an appropriate amount of water. The resulting mixture was extracted with dichlormethane. The organic phase was dried over anhydrous sodium sulfate, and then separated with a silica-gel column (dichlormethane:methanol=5:1) to produce a white solid. The white solid was dissolved in 20 mL absolute alcohol. The resulting mixture was reacted with the introduction of hydrogen chloride gas under cooling in an ice-water bath for 0.5 h, and then rotary-evaporated to dryness in vacuum to produce 42 mg target product of (E)-4-[3-azabicyclo[3.1.0]hexan-3-yl]-N-[4-(3-chloro-4-fluorophenylamino)-7-methoxyquinazolin-6-yl]-2-butenamide hydrochloride in a yield of 6%.

Formula: $C_{24}H_{24}Cl_2FN_5O_2$ molecular weight: 504.4 mass spectrum (m/e): 468.5 (M+1)

$^1$H-NMR (DMSO-$d_6$, 400 MHz): δ11.58 (br, 1H), 11.43 (s, 1H), 10.21 (s, 1H), 9.18 (s, 1H), 8.89 (s, 1H), 7.98 (d, 1H), 7.69 (br, 1H), 7.58 (s, 1H), 7.54 (t, 1H), 6.97 (m, 1H), 6.77 (d, 1H), 4.07 (s, 3H), 3.98 (s, 2H), 3.16 (t, 2H), 1.75 (br, 2H), 1.20 (m, 2H), 1.16 (m, 1H), 0.61 (m, 1H).

Example 2

The preparation of (E)-N-[4-(3-chloro-4-fluorophenylamino)-7-methoxyquinazolin-6-yl]-4-[azaspiro[3.3]heptan-2-yl]-2-butenamide (Compound 2) hydrochloride

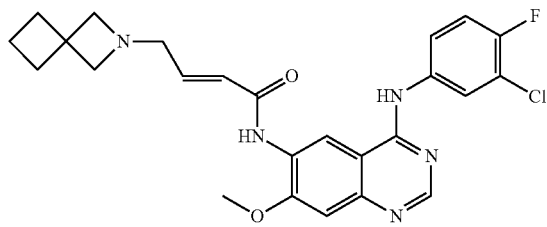 [SMILES: COc1cc2ncnc(Nc3ccc(F)c(Cl)c3)c2cc1NC(=O)/C=C/CN1CC2(CCC2)C1]

(1) The preparation of cyclobutane-1,1-diyldimethanol

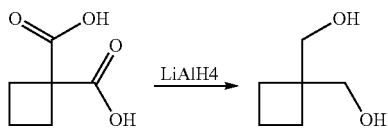

Cyclobutane-1,1-dicarboxylic acid (28.8 g, 0.2 mol) was dissolved in 100 mL THF. To the resulting mixture was added in batch lithium aluminum hydride (22 g, 0.58 mol) under cooling in an ice-water bath. The mixture was reacted at room temperature for 10 h. The reaction was quenched with ethyl acetate and water. The resulting reaction mixture was dried over anhydrous sodium sulfate, filtered, and rotary-evaporated to remove the solvent to produce 21.3 g target product as yellow oil in a yield of 92%. The crude product was directly used in the next step without purification.

(2) The preparation of cyclobutane-1,1-diylbis(methylene)dimethanesulfonate

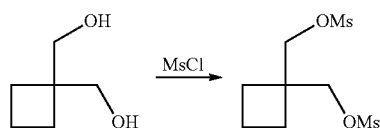 [SMILES: "MsCl" ; OCC1(CO)CCC1 ; CS(=O)(=O)OCC1(COS(C)(=O)=O)CCC1]

The crude product obtained in the previous step was dissolved in 1000 mL dichlormethane and 15 mL triethylamine. To the resulting mixture was added dropwise MsCl (61.56 g, 0.55 mol) under cooling in an ice-water bath. The reaction was continued for 3 h. After filtering, the filtrate was concentrated to dryness to produce 52.6 g target product as yellow solid. The crude product was directly used in the next step without purification.

(3) The preparation of 2-tosyl-2-azaspiro[3.3]heptane

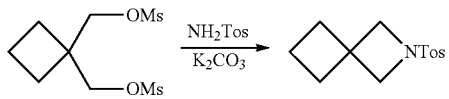

The crude cyclobutane-1,1-diylbis(methylene)dimethanesulfonate (25.3 g, 0.09 mmol) and potassium carbonate (27.6 g, 0.2 mol) were dissolved in 200 mL DMSO. To the resulting mixture was added p-toluenesulfonamide (34.2 g, 0.2 mol) at room temperature. The mixture was reacted for 12 h under heating to 110° C. The reaction system was cooled. To the mixture was added 1000 mL ethyl acetate. The mixture was washed with water. The organic layer was dried over anhydrous sodium sulfate, and rotary-evaporated to dryness. The resulting residue was separated with a silica-gel column (petroleum ether:ethyl acetate=7:1) to produce 14.74 g target product as colorless oil in a yield of 65%.

(4) The preparation of 2-azaspiro[3.3]heptane

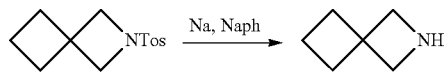

2-tosyl-2-azaspiro[3.3]heptanes (7.3 g, 0.03 mol) was dissolved in 30 mL 1,2-dimethoxyethane. To the resulting mixture was added dropwise 50 mL of a fresh-made sodium naphthalene solution under cooling in ice-water. The resulting mixture was reacted at room temperature for 1 h. The reaction was quenched with water.

The reaction liquor was concentrated and then purified with a silica-gel column (dichlormethane:methanol=20:0-1:0) to produce 2.41 g 2-azaspiro[3.3]heptane in a yield of 83%.

(5) The preparation of (E)-N-[4-(3-chloro-4-fluorophenylamino)-7-methoxyquinazolin-6-yl]-4-[2-azaspiro[3.3]heptan-2-yl]-2-butenamide hydrochloride

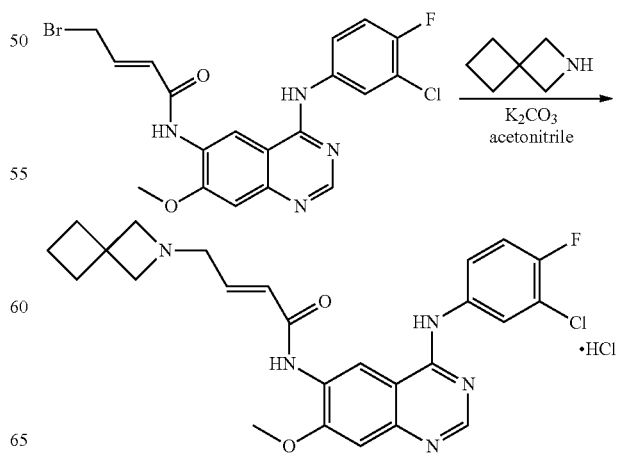

(E)-4-bromo-N-[4-(3-chloro-4-fluorophenylamino)-7-methoxyquinazolin-6-yl]-2-butenamide (595 mg, 1.28 mmol), 2-azaspiro[3.3]heptane (415 mg, 4.25 mmol) and potassium carbonate (781 mg, 5.66 mmol) were dissolved in 50 mL acetonitrile. The resulting mixture was reacted at 60° C. for 10 h. The mixture was cooled to room temperature. To the mixture was added 100 mL water. The mixture was extracted with dichlormethane. The organic layer was dried over anhydrous sodium sulfate, filtered, and concentrated. The resulting residue was separated with a silica-gel column (dichlormethane:methanol=20:1) to produce 72.5 mg yellow solid in a yield of 12%. The yellow solid (150 mg, 0.31 mmol) was dissolved in 10 mL hydrogen chloride/ethanol. The resulting mixture was reacted at room temperature for 2 h. The reaction liquor was rotary-evaporated to dryness to produce the target product (E)-N-[4-(3-chloro-4-fluorophenylamino)-7-methoxyquinazolin-6-yl]-4-[azaspiro[3.3]heptan-2-yl]-2-butenamide hydrochloride.

Formula: $C_{25}H_{26}Cl_2FN_5O_2$ molecular weight: 518.4 mass spectrum (m/e): 482.2 (M+1)

$^1$H-NMR (CDCl$_3$, 400 MHz): δ9.09 (s, 1H), 8.63 (s, 1H), 8.10 (s, 1H), 7.88 (d, 1H), 7.71 (br, 1H), 7.50 (br, 1H), 7.23 (s, 1H), 7.10 (br, 1H), 6.90 (m, 1H), 6.13 (d, 1H), 4.04 (s, 3H), 3.24 (br, 6H), 2.13 (t, 4H), 1.82 (t, 2H).

Example 3

The preparation of (E)-N-[4-(3-chloro-4-fluorophenylamino)-7-methoxyquinazolin-6-yl]-4-(2-azaspiro[3.4]octan-2-yl)-2-butenamide (Compound 14)

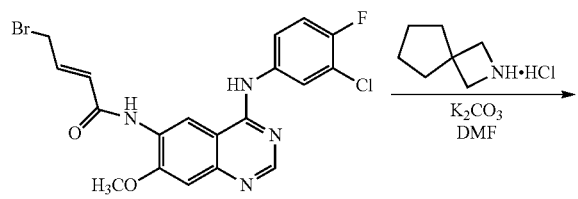

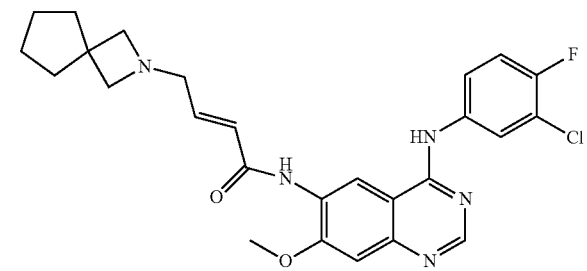

In a dried reaction vessel, (E)-4-bromo-N-[4-(3-chloro-4-fluorophenylamino)-7-methoxyquinazolin-6-yl]-2-butenamide (0.742 g, 1.59 mmol), 2-azaspiro[3,4]octane hydrochloride (0.307 g, 2.082 mmol) and anhydrous potassium carbonate (0.663 g, 4.797 mmol) were dissolved in 25 mL DMF. The resulting mixture was stirred at room temperature for 24 h. To the resulting reaction liquor was added an appropriate amount of water. The resulting mixture was extracted ethyl acetate. The organic phases were combined. The combined mixture was successively washed with water and brine, dried over anhydrous sodium sulfate, filtered, and concentrated. The resulting residue was purified with a silica-gel column chromatography (dichlormethane:methanol=20:1), and then treated with acetonitrile, to produce 110 mg of N-[4-(3-chloro-4-fluorophenylamino)-7-methoxyquinazolin-6-yl]-4-(2-azaspiro[3.4]octan-2-yl)-2-butenamide as pale yellow solid in a yield of 13.9%.

Formula: $C_{26}H_{22}ClFN_5O_2$ molecular weight: 496.0 mass spectrum (m/e): 496.2 (M+1)

$^1$H-NMR (DMSO-d$_6$, 400 MHz): δ9.79 (s, 1H), 9.69 (s, 1H), 8.90 (s, 1H), 8.51 (s, 1H), 8.06-8.18 (m, 1H), 7.71-7.84 (m, 1H), 7.41 (t, J=9.0 Hz, 1H), 7.27 (s, 1H), 6.71 (dt, J=15.3, 4.8 Hz, 1H), 6.51 (d, J=15.3 Hz, 1H), 4.00 (s, 3H), 3.19 (d, J=3.3 Hz, 2H), 3.06 (s, 4H), 1.69 (br. s., 4H), 1.49 (br. s., 4H).

Example 4

The preparation of (E)-N-[4-(3-chloro-4-fluorophenylamino)-7-methoxyquinazolin-6-yl]-4-(2-azaspiro[3.5]nonan-2-yl)-2-butenamide (Compound 15)

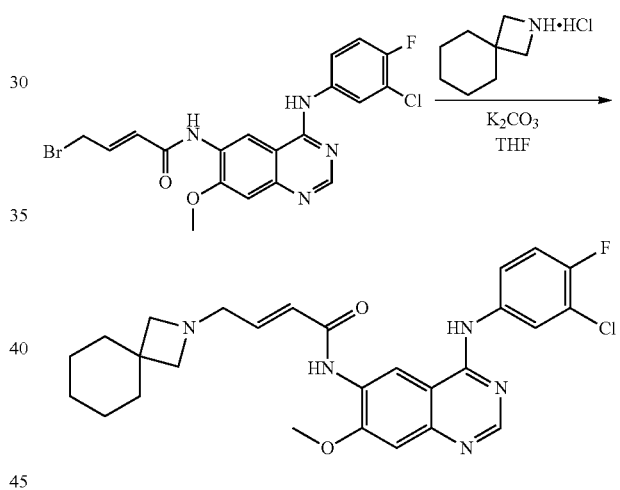

(E)-4-bromo-N-[4-(3-chloro-4-fluorophenylamino)-7-methoxyquinazolin-6-yl]-2-butenamide (3.06 g, 6.6 mmol) and 2-azaspiro[3.5]nonane hydrochloride (2.13 g, 13.2 mmol) were dissolved in 10 mL DMF. To the resulting mixture was added K$_2$CO$_3$ (2.73 g, 19.8 mmol). The mixture was stirred at room temperature for 30 min. After the completion of reaction, 50 mL water was added. The resulting mixture was extracted with ethyl acetate. The organic phase was rotary-evaporated to dryness. The resulting solid was purified with a silica-gel column (dichlormethane:methanol=15:1) to produce 1.21 g (E)-N-[4-(3-chloro-4-fluorophenylamino)-7-methoxyquinazolin-6-yl]-4-(2-azaspiro[3.5]nonan-2-yl)-2-butenamide in a yield of 36%.

Formula: $C_{27}H_{29}ClFN_5O_2$ molecular weight: 510.0 mass spectrum (m/e): 510.2 (M+1)

$^1$H-NMR (MeOD-d$_6$, 400 MHz): δ9.26 (s, 1H), 8.76 (s, 1H), 7.93 (d, 1H), 7.67-7.63 (m, 1H), 7.40 (t, 1H), 7.38 (s, 1H), 7.00-6.89 (m, 1H), 6.81 (d, 1H), 4.19 (s, 3H), 4.02 (d, 2H), 3.49-3.45 (d, 2H), 3.04-3.00 (t, 2H), 2.08-1.60 (m, 10H).

Example 5

The preparation of (E)-N-[4-(3-chloro-4-fluorophenylamino)-7-methoxyquinazolin-6-yl]-4-(7-azaspiro[3.5]nonan-7-yl)-2-butenamide (Compound 17)

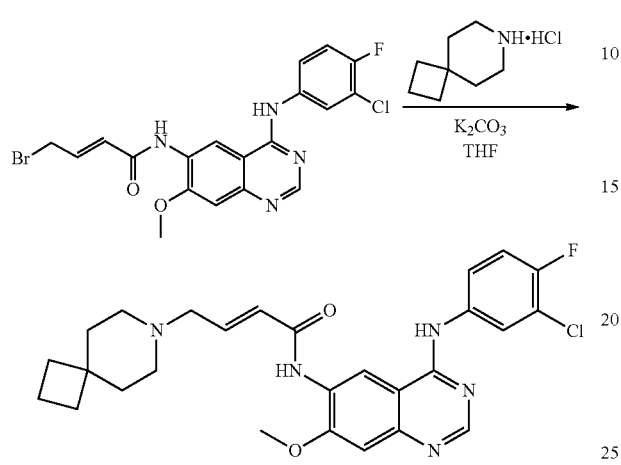

According to the method of Example 3,2-azaspiro[3,4]octane hydrochloride was replaced with 7-azaspiro[3.5]nonane hydrochloride to produce 1.21 g (E)-N-[4-(3-chloro-4-fluorophenylamino)-7-methoxyquinazolin-6-yl]-4-(7-azaspiro[3.5]nonan-7-yl)-2-butenamide in a yield of 36%.

Formula: $C_{27}H_{29}ClFN_5O_2$ molecular weight: 510.0 mass spectrum (m/e): 510.2 (M+1)

$^1$H-NMR (MeOD-d$_6$, 400 MHz): δ9.26 (s, 1H), 8.76 (s, 1H), 7.93 (d, 1H), 7.67-7.63 (m, 1H), 7.38 (t, 1H), 7.32 (s, 1H), 6.93-6.89 (m, 1H), 6.77 (d, 1.0H), 4.37 (d, 2H), 4.19-4.05 (m, 5H), 3.49-3.48 (d, 2H), 2.04-1.78 (m, 5H), 1.56-1.29 (m, 5H).

Example 6

The preparation of (E)-N-[4-(3-chloro-4-fluorophenylamino)-7-methoxyquinazolin-6-yl]-4-(4-azaspiro[2.4]heptan-4-yl)-2-butenamide (Compound 25)

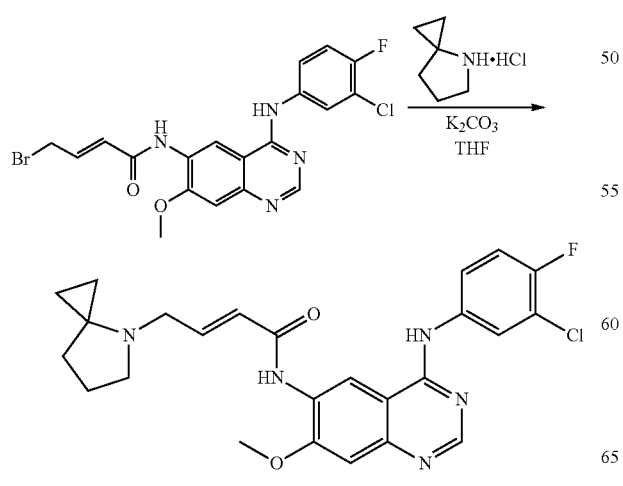

According to the method of Example 3,2-azaspiro[3,4]octane hydrochloride was replaced with 4-azaspiro[2.4]heptane hydrochloride to produce 0.825 g (E)-N-[4-(3-chloro-4-fluorophenylamino)-7-methoxyquinazolin-6-yl]-4-(4-azaspiro[2.4]heptan-4-yl)-2-butenamide in a yield of 26%.

Formula: $C_{25}H_{25}ClFN_5O_2$ molecular weight: 482.0 mass spectrum (m/e): 482.2 (M+1)

$^1$H-NMR (MeOD-d$_6$, 400 MHz): δ9.26 (s, 1H), 8.76 (s, 1H), 7.93 (d, 1H), 7.67-7.63 (m, 1H), 7.40 (t, 1H), 7.34 (s, 1H), 6.89-6.88 (m, 1H), 6.77 (d, 1.0H), 4.19 (s, 3H), 4.05-3.92 (m, 2H), 3.49-3.46 (d, 2H), 2.42-1.99 (m, 4H), 1.56-1.29 (m, 4H).

Example 7

The preparation of (E)-N-[4-(3-chloro-4-fluorophenylamino)-7-methoxyquinazolin-6-yl]-4-(5-azaspiro[2.4]heptan-5-yl)-2-butenamide (Compound 26)

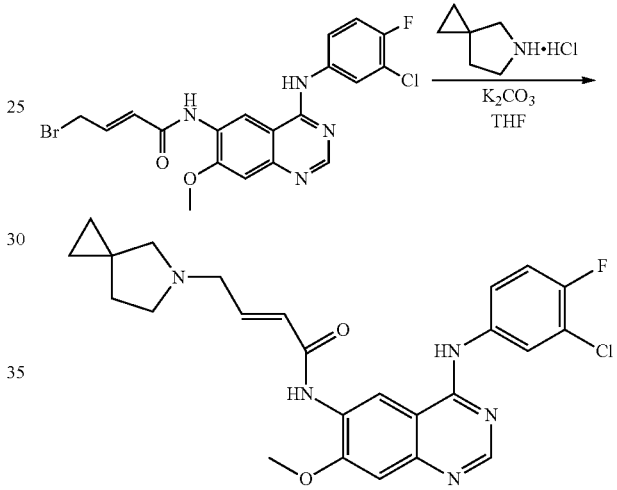

According to the method of Example 3,2-azaspiro[3.4]octane hydrochloride was replaced with 5-azaspiro[2.4]heptane hydrochloride to produce the target compound.

Formula: $C_{25}H_{25}ClFN_5O_2$ molecular weight: 482.0 mass spectrum (m/e): 482.2 (M+1)

$^1$H-NMR (DMSO-d$_6$, 400 MHz) δ: 9.80 (s, 1H), 9.69 (s, 1H), 8.86-8.99 (m, 1H), 8.52 (s, 1H), 8.06-8.18 (m, 1H), 7.75-7.87 (m, 1H), 7.41 (t, J=9.0 Hz, 1H), 7.27 (s, 1H), 6.76-6.91 (m, 1H), 6.59 (d, J=15.6 Hz, 1H), 4.00 (s, 3H), 3.24 (m, 2H), 2.60-2.77 (m, 2H), 1.74 (m, 2H), 0.51 (m, 4H).

Example 8

The preparation of (E)-N-[4-(3-chloro-4-fluorophenylamino)-7-methoxyquinazolin-6-yl]-4-(6-azaspiro[3.4]nonan-6-yl)-2-butenamide (Compound 27)

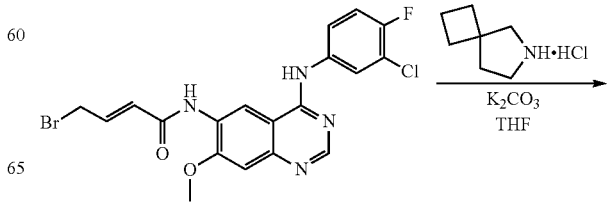

-continued

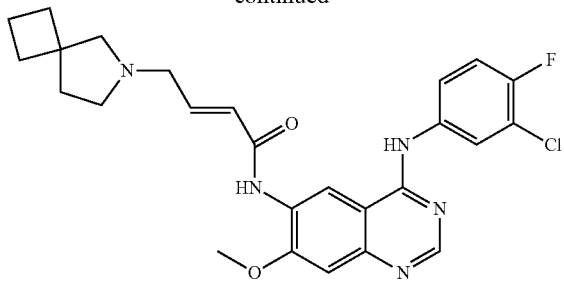

According to the method of Example 3, 2-azaspiro[3,4]octane hydrochloride was replaced with 6-azaspiro[3.4]octane hydrochloride to produce the target compound.

Formula: $C_{26}H_{27}ClFN_5O_2$ molecular weight: 496.0 mass spectrum (m/e): 496.2 (M+1)

$^1$H-NMR (DMSO-d$_6$, 400 MHz) δ: 9.80 (s, 1H), 9.71 (br. s., 1H), 8.91 (s, 1H), 8.52 (s, 1H), 8.09-8.15 (m, 1H), 7.75-7.82 (m, 1H), 7.41 (t, J=9.0 Hz, 1H), 7.27 (s, 1H), 6.80 (dt, J=15.2, 5.8 Hz, 1H), 6.58 (d, J=15.3 Hz, 1H), 4.00 (s, 3H), 3.27 (br. s., 2H), 2.59 (s, 4H), 1.71-2.02 (m, 8H).

Example 9

The preparation of (E)-N-[4-(3-chloro-4-fluorophenylamino)-7-methoxyquinazolin-6-yl]-4-(2-oxa-6-azaspiro[3.5]nonane)-6-yl)-2-butenamide (Compound 28)

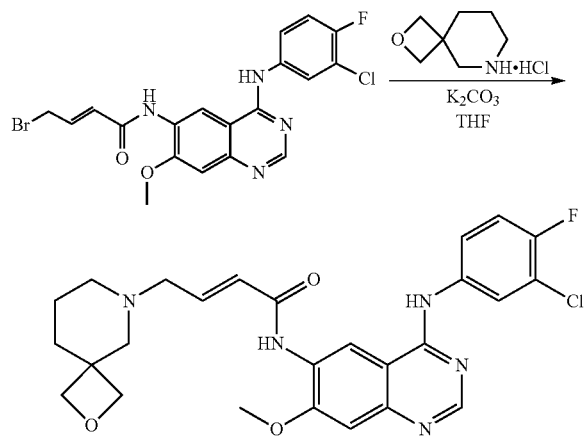

According to the method of Example 3,2-azaspiro[3.4]octane hydrochloride was replaced with 2-oxa-6-azaspiro[3.5]nonane hydrochloride to produce 0.71 g of the target compound (E)-N-[4-(3-chloro-4-fluorophenylamino)-7-methoxyquinazolin-6-yl]-4-(2-oxa-6-azaspiro[3.5]nonane)-6-yl)-2-butenamide in a yield of 21%.

Formula: $C_{26}H_{27}ClFN_5O_3$ molecular weight: 512.0 mass spectrum (m/e): 512.2 (M+1)

$^1$H-NMR (CDCl$_3$-d$_6$, 400 MHz): δ9.11 (s, 1H), 8.63 (s, 1H), 7.96 (d, 1H), 7.68-7.60 (m, 2H), 7.34 (s, 1H), 7.04 (t, 1H), 6.22 (d, 1H), 4.42 (d, 4H), 4.08 (d, 3H), 3.25 (d, 2H), 2.40 (s, 2H), 2.22-2.20 (m, 2H), 2.02 (m, 2H), 1.59-1.56 (m, 2H).

Example 10

The preparation of (E)-N-[4-(3-chloro-4-fluorophenylamino)-7-methoxyquinazolin-6-yl]-4-(2-oxa-7-azaspiro[3.5]nonan-7-yl)-2-butenamide (Compound 29)

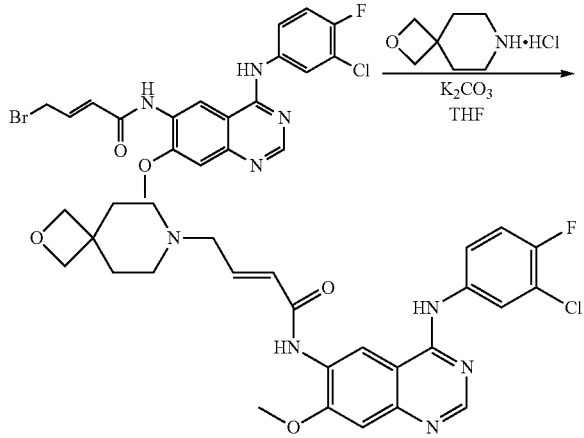

According to the method of Example 4,2-azaspiro[3.4]octane hydrochloride was replaced with 2-oxa-7-azaspiro[3.5]nonane hydrochloride to produce the target compound.

Formula: $C_{26}H_{27}ClFN_5O_3$ molecular weight: 512.0 mass spectrum (m/e): 512.2 (M+1)

$^1$H-NMR (DMSO-d$_6$, 400 MHz) δ: 9.79 (s, 1H), 9.69 (s, 1H), 8.91 (s, 1H), 8.52 (s, 1H), 8.12 (dd, J=6.8, 2.3 Hz, 1H), 7.79 (dt, J=8.5, 3.5 Hz, 1H), 7.41 (t, J=9.2 Hz, 1H), 7.27 (s, 1H), 6.77 (dt, J=15.3, 6.0 Hz, 1H), 6.55 (d, J=15.3 Hz, 1H), 4.26 (s, 4H), 4.00 (s, 3H), 3.07 (d, J=5.8 Hz, 2H), 2.27 (br. s., 4H), 1.78 (br. s., 4H).

Example 11

The preparation of (E)-N-[4-(3-chloro-4-fluorophenylamino)-7-methoxyquinazolin-6-yl]-4-(6-azaspiro[2.5]octan-6-yl)-2-butenamide (Compound 30)

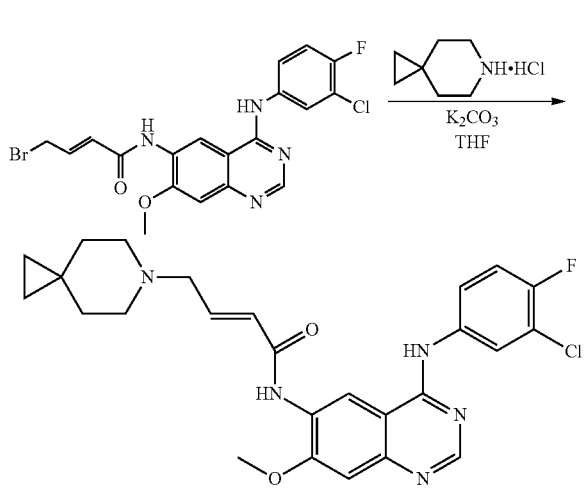

According to the method of Example 4,2-azaspiro[3.4]octane hydrochloride was replaced with 6-azaspiro[2.5]octane hydrochloride to produce the target compound.

Formula: $C_{26}H_{27}ClFN_5O_2$ molecular weight: 496.0 mass spectrum (m/e): 496.2 (M+1)

$^1$H-NMR (DMSO-d$_6$, 400 MHz) δ: 9.79 (s, 1H), 9.69 (s, 1H), 8.91 (s, 1H), 8.52 (s, 1H), 8.12 (dd, J=6.8, 2.3 Hz, 1H), 7.79 (dt, J=8.3, 3.5 Hz, 1H), 7.41 (t, J=9.2, 1H), 7.27 (s, 1H), 6.82 (dt, J=15.2, 6.1 Hz, 1H), 6.57 (d, J=15.6 Hz, 1H), 4.00 (s, 3H), 3.16 (d, J=4.8 Hz, 2H), 2.42 (br. s., 4H), 1.35 (br. s., 4H), 0.24 (s, 4H).

The following compounds could also be prepared according to the above-mentioned methods:

| No. | Compound | | No. | Compound |
|---|---|---|---|---|
| 41 | 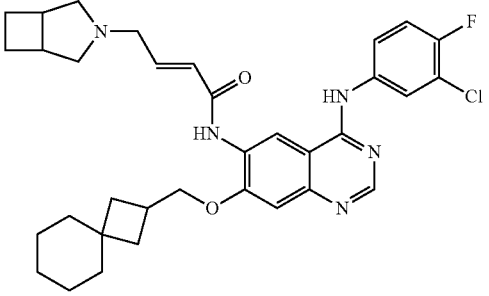 [SMILES: O=C(/C=C/CN1CC2CCC2C1)Nc1cc2c(Nc3ccc(F)c(Cl)c3)ncnc2cc1OCC1CC2(CCCCC2)C1] | | 46 | 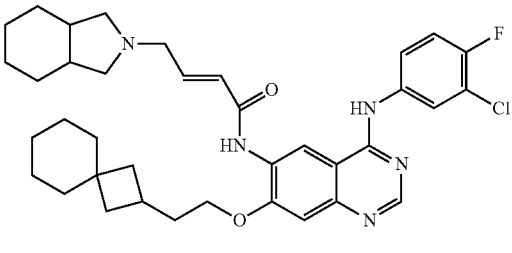 |
| 42 | 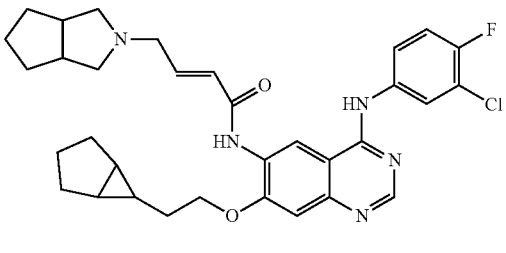 [SMILES: O=C(/C=C/CN1CC2CCCC2C1)Nc1cc2c(Nc3ccc(F)c(Cl)c3)ncnc2cc1OCCC1C2CCCC21] | | 47 | 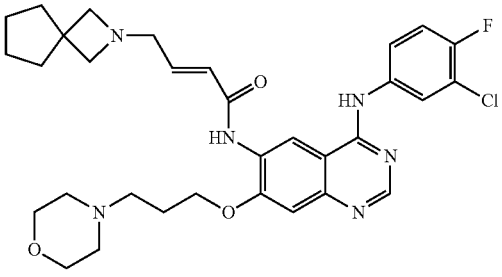 |
| 43 | 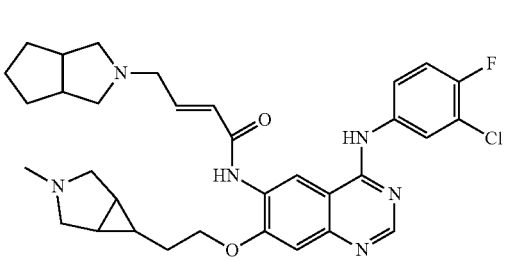 [SMILES: CN1CC2C(CCOc3cc4ncnc(Nc5ccc(F)c(Cl)c5)c4cc3NC(=O)/C=C/CN3CC4CCCC4C3)C2C1] | | 48 | 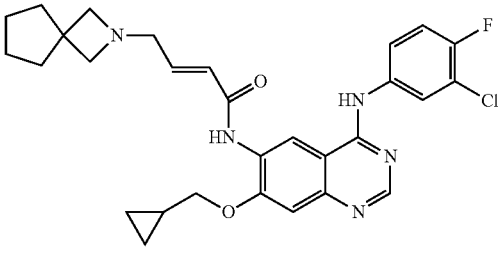 |
| 44 | 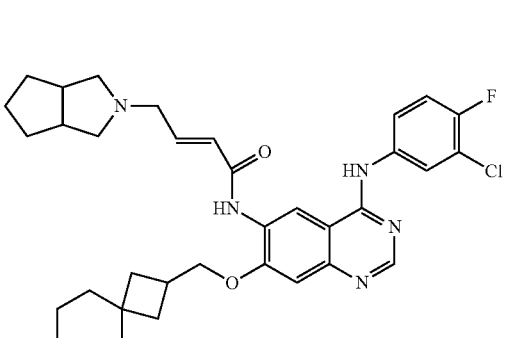 | | 49 | 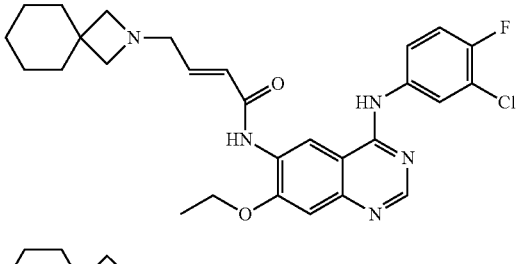 |
| 45 | 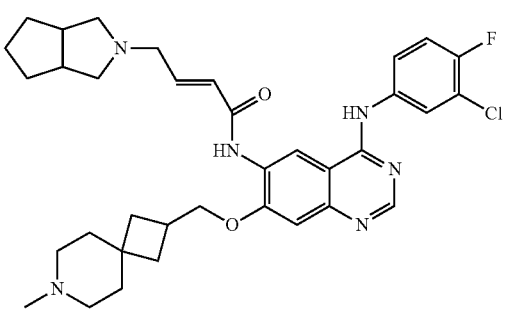 [SMILES: CN1CCC2(CC1)CC(COc1cc3ncnc(Nc4ccc(F)c(Cl)c4)c3cc1NC(=O)/C=C/CN1CC3CCCC3C1)C2] | | 50 | 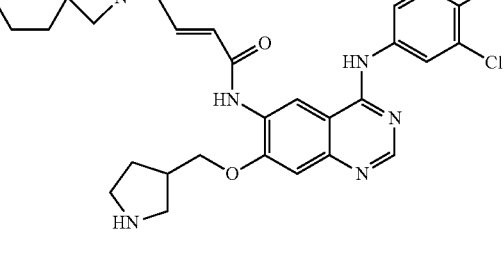 |
| | | | 51 |  |

| No. | Compound |
|---|---|
| 52 | (structure) |
| 53 | (structure) |
| 54 | (structure) |
| 55 | (structure) |
| 56 | (structure) |
| 57 | (structure) |
| 58 | (structure) |
| 59 | (structure) |
| 60 | (structure) |
| 61 | (structure) |
| 62 | (structure) |
| 63 | (structure) |

| No. | Compound |
|---|---|
| 64 | 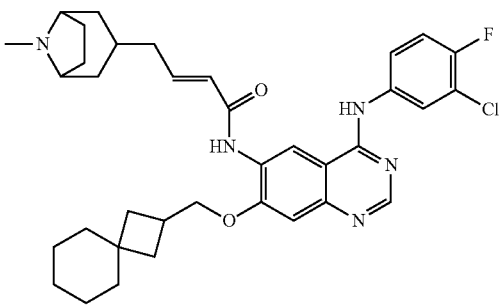 [SMILES: CN1C2CCC1CC(C/C=C/C(=O)Nc1cc3c(Nc4ccc(F)c(Cl)c4)ncnc3cc1OCC1CC3(CCCCC3)C1)C2] |
| 65 | 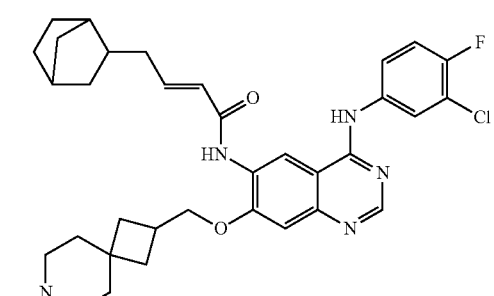 |
| 66 | 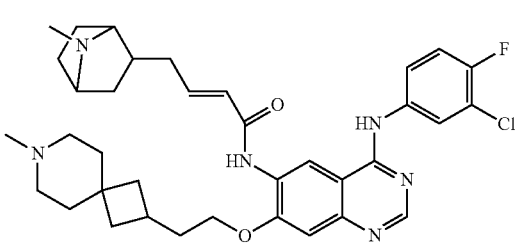 [SMILES: CN1CCC2(CC1)CC(CCOc1cc3ncnc(Nc4ccc(F)c(Cl)c4)c3cc1NC(=O)/C=C/CC1CC3CCC1N3C)C2] |
| 67 | 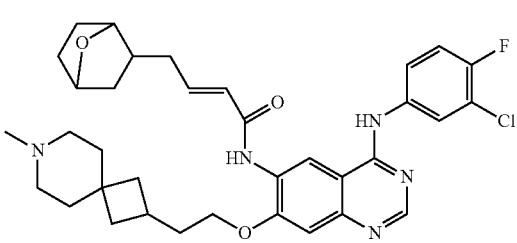 [SMILES: CN1CCC2(CC1)CC(CCOc1cc3ncnc(Nc4ccc(F)c(Cl)c4)c3cc1NC(=O)/C=C/CC1CC3CCC1O3)C2] |
| 68 | 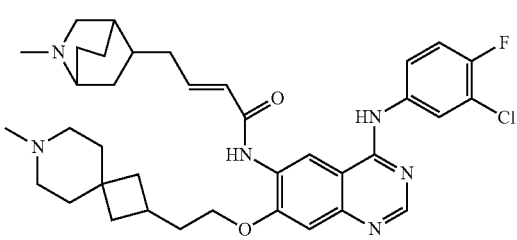 [SMILES: CN1CCC2(CC1)CC(CCOc1cc3ncnc(Nc4ccc(F)c(Cl)c4)c3cc1NC(=O)/C=C/CC1CC3CCC1CN3C)C2] |

| No. | Compound |
|---|---|
| 69 | 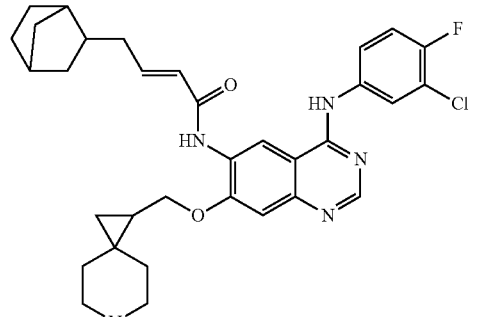 |
| 70 | 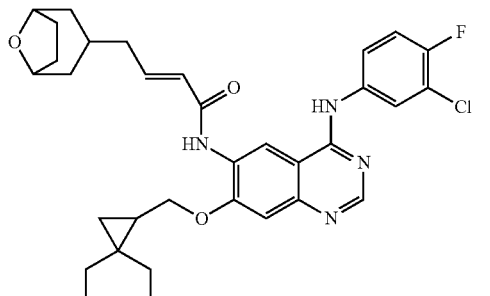 |

II. In Vitro Assays for the Antineoplastic Activities of the Present Compounds

Hereinafter, the beneficial effects of the present compounds will be illustrated by in vitro enzyme inhibitory activity and in vitro cellular inhibitory activity. However, it should be noted that the beneficial effects of the present compounds are not limited to the effects as illustrated below.

Assay 1

In Vitro Enzyme Inhibitory Activity of the Present Compounds

Samples:

Controls: PF-00299804, lab-made; Gefitinib, purchased from Anqing worldchem Co., LTD.; Erlotinib hydrochloride, purchased from Anqing worldchem Co., LTD.; Lapatinib ditosylate, purchased from Taizhou Xingcheng Chempharm Co., Ltd.; referring to the section "Background Art" hereinabove for the structures of the above-mentioned four compounds; and The present compounds: lab-made, their chemical names and structural formulae are shown in the preparation examples.

Assay Procedures:

The abbreviations used in the following assay have the following meanings:

HEPES: hydroxyethyl piperazine ethanesulfonic acid;
Brij-35: polyethylene glycol lauryl ether;
DTT: dithiothreitol;
Coating Reagent #3: #3 coating agent;
EDTA: ethylene diamine tetraacetic acid, purchased from Sigma Co. Ltd.;
FAM labeled peptide: fluorescein labeled peptide 22 (GL Biochem);

ATP: adenosine triphosphate (Sigma);
DMSO: dimethyl sulfoxide;
EGFR: human epidermal growth factor receptor (Carna);
HER2: human epidermal growth factor receptor 2 (Carna);
HER4: human epidermal growth factor receptor 4 (Carna).

1. Formulating the agents to be used in the assay
(1) 1.25-fold $MnCl_2$-free kinase buffer (62.5 mM HEPES, PH 7.5, 0.001875% Brij-35, 12.5 mM $MgCl_2$, 2.5 mM DTT);
(2) 1.25-fold $MnCl_2$-containing kinase buffer (62.5 mM HEPES, pH 7.5, 0.001875% Brij-35, 12.5 mM $MgCl_2$, 12.5 mM $MnCl_2$, 2.5 mM DTT);
(3) Stop buffer (100 mM HEPES, pH 7.5, 0.015% Brij-35, 0.2% Coating Reagent #3, 50 mM EDTA);
(4) 2.5-fold kinase solutions (to the 1.25-fold kinase buffers were added the corresponding kinases to formulate 2.5-fold EGFR, HER2, HER4 kinase solutions);
(5) 2.5-fold peptide solutions (to the 1.25-fold kinase buffers were added FAM labeled peptide and ATP to formulate the peptide solutions);
(6) 5-fold compound solutions (using 100% DMSO to formulate 50-fold compound solutions having different concentration gradients, and diluting with water by 10 times to obtain 5-fold compound solutions having different concentration gradients);
2. Adding 5 μL of a 5-fold compound solution to a 384-well plate;
3. Adding 10 μL of a 2.5-fold kinase solution to incubate for 10 min;
4. Then adding 10 μL of a 2.5-fold peptide solution, and reacting at 28° C. for 1 h;
5. Finally, adding 25 μL of stop buffer to terminate the reaction, and reading the data with Caliper.
6. Curve fitting to obtain an $IC_{50}$ value.

The calculated inhibition ratio (%)=(the maximum conversion rate–the conversion rate)/(the maximum conversion rate–the minimum conversion rate)×100

The curve fitting was conducted with the X1fit software to obtain $IC_{50}$ values.
The results:
See Table 1 below.

TABLE 1

In vitro enzyme inhibitory activity

| Compound | Enzyme inhibitory activity $IC_{50}$(nM) | | |
|---|---|---|---|
| | EGFR | HER2 | HER4 |
| PF-00299804 | 0.89 | 11 | 1.7 |
| Gefitinib | 1.6 | 318 | 7.6 |
| Erlotinib hydrochloride | 1.3 | 454 | 49 |
| Lapatinib ditosylate | 16 | 4.0 | 250 |
| Compound 1 | 0.55 | 14 | 3.1 |
| Compound 2(hydrochloride) | 0.65 | 19 | 8.9 |

Conclusion:
It can be seen from Table 1 that the present compounds have stronger inhibitory activities on EGFR, HER2 and HER4 kinases. The present compounds have a remarkably better inhibitory activity on the EGFR kinase than Lapatinib ditosylate; the present compounds have a remarkably better inhibitory activity on the HER2 kinase than Gefitinib and Erlotinib hydrochloride; the present compounds have a remarkably better inhibitory activity on the HER4 kinase than Erlotinib hydrochloride and Lapatinib ditosylate; and the present compounds are comparable with PF-00299804 in the inhibitory activities on EGFR, HER2 and HER4 kinases.

Assay 2
In Vitro Cellular Inhibitory Activity of the Present Compounds
Samples:
Controls: PF-00299804, lab-made; Gefitinib, purchased from Anqing worldchem Co., LTD.; Erlotinib hydrochloride, purchased from Anqing worldchem Co., LTD.; Lapatinib ditosylate, purchased from Taizhou Xingcheng Chempharm Co., Ltd.; and
The present compounds: lab-made, their chemical names and structural formulae are shown in the preparation examples.
Materials and Apparatuses in Assay:

| Materials and Apparatuses | batch number/ model number | Source |
|---|---|---|
| 3,3′-Sodium [1-(phenylcarbamoyl)-3,4-tetrazolium]-di(4-methoxy-6-nitro)benzene-sulfonate/ 2,3-Bis-(2-methoxy-4-nitro-5-sulfophenyl]-2H-tetrazolium-5-carboxamide salt (XTT) | X4251 | Sigma |
| RPMI1640 (a medium designed by Roswell Park Memorial Institute) | NWB0377 | Hyclone |
| DMEM | NVH0300 | Hyclone |
| MEM | NVK0322 | Hyclone |
| F12K | 30612100 | M&G |
| McCoy's 5A | 1814342 | GIBCO |
| Fetal calf serum | GUH0069 | Hyclone |
| Phosphate buffer (PBS) | Formulated on 2011 Feb. 19 | Homemade |
| 96-well plate | 3599 | Corning |
| Microplate oscillator | QB-9002 | QILINBEIER |
| Centrifuger | 5810R | Eppendorf |
| $CO_2$ incubator | 371 | Thermo Scientific |
| Microplate reader | Infinite M200 | TECAN |

| Cells | No. | Source |
|---|---|---|
| H1975 | CRL-5908 | Chinese Vendor |
| SKOV3 | HTB-77 | Chinese Vendor |
| A431 | CRL-1555 | Chinese Vendor |

Assay Procedures:
1. Formulating the Agents and the Compounds
1) Formulating PBS:
NaCl (8 g), KCl (0.2 g), $Na_2HPO_4$ (1.44 g), and $KH_2PO_4$ (0.24 g) were added to ultrapure water (800 mL). After adjusting the pH to 7.4, ultrapure water was further added until the volume reached 1 L. The mixture was autoclaved for 20 min.
2) Formulating the XTT Working Liquor:
XTT powder (100 mg) was taken and, while being kept in darkness, dissolved into 300 ml of the serum-free RPMI1640 culture medium that was warmed to 50° C. and did not contain phenol red. The mixture was filtered, packaged separately, and used immediately or within one week. It is necessary for all of the processes to be kept in darkness.
3) Formulating Test Compounds
Formulating a stock solution of test compound:
The compound powder was dissolved into DMSO until a concentration of 10 mM reached.
Formulating gradient dilute solutions of test compound:
First, the 10 mM stock solution of test compound was diluted with DMSO in a 4-fold successive gradient for 10 concentrations. 2 µL DMSO-diluted compound was added to 998 µL of the culture medium containing 10% FBS. Therefore, the maximum concentration of the compound is 20 µM, the concentration of DMSO is 0.2%, and there are 10 concentration gradients in total.

2. Culturing Cells
1) Thawing Cells:
   A cell-freezing tube was removed from liquid nitrogen, and placed in a water bath of 37° C.-39° C. to thaw the cells quickly.
   A freezing-preserving solution was transferred to 15 ml sterile centrifuge tube, to which was added a culture medium in a volume 10 times larger than that of the freezing-preserving solution. The mixture was centrifuged at 1000 rpm at 4° C. for 5 min. The culture medium in the centrifuge tube was discarded, and then a culture medium containing 10% FBS was added. The cells were resuspended and transferred to the culture bottle. On the next day, the solution was changed.
2) Passing Cells
   For the logarithmic growth phase cells, the culture medium was discarded and an appropriate volume of PBS was added to wash the cells once. Then an appropriate volume of a digestive juice containing 0.25% pancreatic enzyme and 0.02% EDTA was added. The solution was placed on stand at 37° C. for 2-5 min, and then washed once with PBS after the digestive juice was discarded. An appropriate volume of a culture medium containing 10% FBS was added to terminate the digestion. The pipette was blown and hit slightly, and the cells were digested down to produce a cell suspension for cell passage and further experiment.
3) Freezing and Preserving Cells
   For the logarithmic growth phase cells, a digestive juice containing 0.25% pancreatic enzyme and 0.02% EDTA was used to digest cells to produce a cell suspension. The suspension was centrifuged at 1000 rpm at 4° C. for 5 min. The culture medium was discarded and a freezing-preserving solution containing 10% DMSO and 90% FBS was added to resuspend the cells. The cells were packaged separately in the cell-freezing tubes in $2\times10^6$ cells/tube. The cell-freezing tubes were placed in a programmed cooling cassette, kept at −80° C. for 24 hours, and then transferred to liquid nitrogen for freezing and preserving.

3. Plating Cells
1) Preparing the cell suspension
   The culture medium was removed from the culture bottle. The cells were rinsed twice with PBS. The pancreatic enzyme was added to digest cells. The digested cells were collected by centrifuge. The cells were resuspended with a culture medium containing 10% fetal calf serum, counted and adjusted to an appropriate concentration (the cell viability should be over 90%). The cell concentration was $5\times10^4$/ml.
2) The cell suspension was added to the 96-well plate, 100 µL per well.
3) The plate was placed in the incubator and incubated at 37° C. under 5% $CO_2$ overnight.

4. Treating with Drugs
   Drugs were added to the cell culture plate. The plate was placed in the incubator and incubated at 37° C. under 5% $CO_2$ for 72 hours.

5. Testing the Cell Viability with the XTT Method
   The XTT working solution was added to the plate. The plate was placed in the incubator at 37° C. under 5% $CO_2$ for 2 hr. Then the plate was placed in a microplate reader to read the absorbance at 450 nm.

6. Data Processing
1) The percent inhibition was calculated by the following calculation.

% inhibition=(Absorbance(medium)−Absorbance(Compound))/(Absorbance(medium)−Absorbance(positive control))×100%;

2) Data were input into GraphPad Prism 5.0 to plot a curve and obtain $IC_{50}$.

Result:
   See the Tables 2-4 below.

TABLE 2 in vitro cellular inhibitory activities on H1975 (NSCLC, non-small cell lung cancer)
H1975 Cells

| Compound | $IC_{50}$ (nM) |
| --- | --- |
| PF-00299804 | 356.5 |
| Erlotinib hydrochloride | 3985.0 |
| Lapatinib ditosylate | 4534.0 |
| Compound 2 | 147.8 |
| Compound 14 | 133.5 |
| Compound 15 | 179.4 |
| Compound 26 | 85.6 |
| Compound 27 | 91.9 |
| Compound 28 | 39.01 |
| Compound 29 | 57.1 |

TABLE 3 in vitro cellular inhibitory activities on SKOV3 (Ovarian carcinoma)
SKOV3 cells

| Compound | $IC_{50}$ (nM) |
| --- | --- |
| PF-00299804 | 3959.0 |
| Erlotinib hydrochloride | >10000 |
| Lapatinib ditosylate | 4329.0 |
| Compound 2 | 3218.0 |
| Compound 14 | 3711.0 |
| Compound 15 | 3645.0 |
| Compound 17 | 3063.0 |
| Compound 26 | 3074.0 |
| Compound 27 | 3186.0 |
| Compound 30 | 3348.0 |

TABLE 4 in vitro cellular inhibitory activities on A431 (Epidermoid carcinoma)
A431 cells

| Compound | $IC_{50}$ (nM) |
| --- | --- |
| PF-00299804 | 548.5 |
| Erlotinib hydrochloride | 1269.0 |
| Lapatinib ditosylate | 3282.0 |
| Compound 2 | 33.3 |

CONCLUSIONS

It can be seen from Table 2 that the cellular proliferation inhibition effect of the present compounds on H1975 (NSCLC, non-small cell lung cancer) is remarkably superior to Erlotinib hydrochloride, Lapatinib ditosylate and PF-00299804.

It can be seen from Table 3 that the cellular proliferation inhibition effect of the present compounds on SKOV3 (Ovarian carcinoma) is remarkably superior to Erlotinib hydrochloride, and is comparable with PF-00299804 and Lapatinib ditosylate.

It can be seen from Table 4 that the cellular proliferation inhibition effect of the present compounds on A431 (Epidermoid carcinoma) is remarkably superior to Erlotinib hydrochloride, Lapatinib ditosylate and PF-00299804.

The invention claimed is:

1. A compound represented by the general formula (I), and its pharmaceutically acceptable salt or stereoisomer thereof:

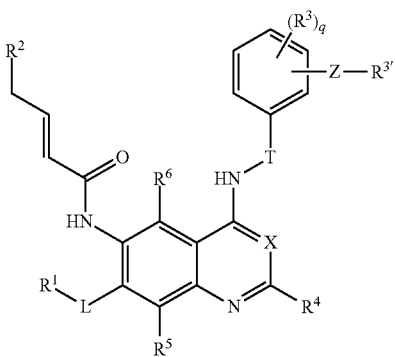

wherein:
- $R^1$ is selected from the following groups that are unsubstituted or substituted by 1-3 same or different $Q^1$: $C_{1-6}$alkyl, $C_{3-6}$alkenyl, $C_{3-6}$alkynyl, $C_{3-6}$cycloalkyl-$C_{0-6}$ alkyl, 6-10-membered fused ring-$C_{0-6}$alkyl, 7-10-membered spiro ring-$C_{0-6}$ alkyl and 7-10-membered bridged ring-$C_{0-6}$alkyl, and the carbon atom in said cycloalkyl, said fused ring, said spiro ring and said bridged ring may be optionally replaced by 1-3 same or different groups consisting of O, S(O)$_m$, N(H)$_n$ and/or C(O),
- $Q^1$ is selected from the groups consisting of halogen, hydroxy, amino, carboxyl, cyano, $C_{1-6}$alkyl, $C_{1-6}$alkoxyl, $C_{1-6}$alkylamino, di($C_{1-6}$alkyl)amino, $C_{1-6}$alkylcarbonyloxy, $C_{1-4}$alkoxylcarbonyl, $C_{1-6}$alkylacylamino, $C_{1-6}$alkylsulfonyl, $C_{1-6}$alkylsulfinyl, $C_{1-6}$alkylsulfonylamino and $C_{3-8}$cycloalkyl;
- $R^2$ is selected from the following groups that are unsubstituted or substituted by 1-2 same or different $Q^2$: $C_{3-4}$cycloalkyl-$C_{0-6}$alkyl, 6-10-membered fused ring-$C_{0-6}$alkyl, 7-10-membered spiro ring-$C_{0-6}$alkyl and 7-10-membered bridged ring-$C_{0-6}$alkyl, and the carbon atom in said cycloalkyl, said fused ring, said spiro ring and said bridged ring may be replaced by 1-3 same or different groups consisting of O, S(O)$_m$, N(H)$_n$ and/or C(O), provided that an ester structure "—O—C(O)—" is not present in the replaced ring and when $R^2$ is 7-10-membered bridged ring-$C_{0-6}$alkyl, $R^1$ is not $C_{3-4}$cycloalkyl-$C_{0-6}$alkyl or $C_{1-6}$alkyl; $Q^2$ is selected from the groups consisting of halogen, hydroxy, amino, carboxyl, cyano, nitro, trifluoromethyl, $C_{1-6}$alkyl, $C_{1-6}$alkoxyl, $C_{1-6}$alkylamino, di($C_{1-6}$alkyl)amino, $C_{1-6}$alkylcarbonyloxy, $C_{1-6}$alkoxylcarbonyl, $C_{1-6}$alkylacylamino, $C_{1-6}$alkylsulfonyl, $C_{1-6}$alkylsulfinyl and $C_{1-6}$alkylsulfonylamino;
- $R^3$ is selected from the group consisting of halogen, hydroxy, cyano, nitro, trifluoromethyl, carbamoyl, $C_{1-6}$alkyl, $C_{2-6}$alkenyl, $C_{2-6}$alkynyl, $C_{1-6}$alkoxyl, $C_{1-6}$alkyl substituted with halogen and $C_{1-6}$alkoxyl substituted with halogen, $C_{1-6}$alkylamino, di($C_{1-6}$alkyl)amino, $C_{1-6}$alkylthio, $C_{1-6}$alkylcarbamoyl, $C_{1-6}$alkylcarbonyl, $C_{1-6}$alkoxylcarbonyl, $C_{1-6}$alkylcarbonyloxy, $C_{1-6}$alkylacylamino, $C_{1-6}$alkylsulfonyl, $C_{1-6}$alkylsulfinyl and $C_{1-6}$alkylsulfonylamino;
- $R^{3'}$ is absent;
- $R^4$, $R^5$ and $R^6$ are each independently selected from the group consisting of hydrogen, halogen, $C_{1-6}$alkyl, $C_{1-6}$alkoxyl, $C_{1-6}$alkyl substituted with halogen and $C_{1-6}$alkoxyl substituted with halogen, $C_{1-6}$alkylamino and di($C_{1-6}$alkyl)amino;
- X is selected from the group consisting of cyano-substituted methenyl or a nitrogen atom;
- L is selected from the group consisting of O, S(O)$_m$, N(H), N(CH$_3$) or C(O);
- T is selected from the group consisting of a covalent bond, C(O) or CH(R'), R' is selected from the group consisting of hydrogen or $C_{1-6}$alkyl;
- Z is hydrogen;
- q is 2, and $R^3$ may be identical or different;
- m is selected from the group consisting of 0, 1 or 2; and
- n is selected from the group consisting of 0 or 1.

2. The compound of claim 1, its pharmaceutically acceptable salt or stereoisomer thereof, wherein
- $R^1$ is selected from the group consisting of the following groups that are unsubstituted or substituted by 1-3 same or different $Q^1$: $C_{1-4}$alkyl, $C_{3-8}$cycloalkyl-$C_{0-4}$alkyl, 6-10-membered fused ring-$C_{0-4}$alkyl, 7-10-membered spiro ring-$C_{0-4}$alkyl and 7-10-membered bridged ring-$C_{0-4}$alkyl, the carbon atom in said cycloalkyl, said fused ring, said spiro ring or said bridged ring may be optionally replaced by 1-3 same or different groups consisting of O, S(O)$_m$, N(H)$_n$ and/or C(O), $Q^1$ is selected from the group consisting of halogen, hydroxy, amino, carboxyl, cyano, $C_{1-4}$alkyl, $C_{1-4}$alkoxyl, $C_{1-4}$alkylamino, di($C_{1-4}$alkyl)amino, $C_{1-4}$alkylcarbonyloxy, $C_{1-4}$alkoxylcarbonyl, $C_{1-4}$alkylacylamino, $C_{1-4}$alkylsulfonyl, $C_{1-4}$alkylsulfinyl, $C_{1-4}$alkylsulfonylamino and $C_{3-8}$cycloalkyl; or
- $R^2$ is selected from the group consisting of the following groups that are unsubstituted or substituted by 1-2 same or different $Q^2$: cyclopropyl-$C_{0-4}$alkyl, cyclobutyl-$C_{0-4}$alkyl, 6-10-membered fused ring-$C_{0-4}$alkyl, 7-10-membered spiro ring-$C_{0-4}$alkyl or 7-10-membered bridged ring-$C_{0-4}$alkyl, the carbon atom in said cyclopropyl, said cyclobutyl, said fused ring, said spiro ring or said bridged ring may be optionally replaced by 1-2 same or different groups consisting of O, S(O)$_m$, N(H)$_n$ and/or C(O), provided that an ester structure "—O—C(O)—" is not present in the replaced ring, and when $R^2$ is 7-10-membered bridged ring-$C_{0-4}$alkyl, $R^1$ is not $C_{3-4}$cycloalkyl-$C_{0-4}$alkyl or $C_{1-4}$alkyl; $Q^2$ is selected from the group consisting of halogen, hydroxy, amino, cyano, $C_{1-4}$alkyl, $C_{1-4}$alkoxyl, $C_{1-4}$alkylamino, di($C_{1-4}$alkyl)amino, $C_{1-4}$alkylcarbonyloxy, $C_{1-4}$alkoxylcarbonyl, $C_{1-4}$alkylacylamino, $C_{1-4}$alkylsulfonyl, $C_{1-4}$alkylsulfinyl and $C_{1-4}$alkylsulfonylamino; or
- $R^3$ is selected from the group consisting of hydrogen, halogen, hydroxy, cyano, nitro, carbamoyl, $C_{1-4}$alkyl, $C_{2-4}$alkenyl, $C_{2-4}$alkynyl, $C_{1-4}$alkoxyl, $C_{1-4}$alkyl substituted with halogen, $C_{1-4}$alkoxyl substituted with halogen, $C_{1-4}$alkylamino, di($C_{1-4}$alkyl)amino, $C_{1-4}$alkylthio, $C_{1-4}$alkylcarbamoyl, $C_{1-4}$alkylcarbonyl, $C_{1-4}$alkoxylcarbonyl, $C_{1-4}$alkylcarbonyloxy, $C_{1-4}$alkylacylamino, $C_{1-4}$alkylsulfonyl, $C_{1-4}$alkylsulfinyl and $C_{1-4}$alkylsulfonylamino; or R⁴, R⁵ and R⁶ are each independently selected from the group consisting of hydrogen, halogen, $C_{1-4}$alkyl, $C_{1-4}$alkoxyl, $C_{1-4}$alkyl substituted with halogen, $C_{1-4}$alkoxyl substituted with halogen, $C_{1-4}$alkylamino and di($C_{1-4}$alkyl)amino; or L is selected from the group consisting of O, S(O)$_m$ or N(H); or T is selected from the group consisting of a covalent bond or CH(R'), R' is selected from the group consisting of hydrogen or methyl.

3. The compound of claim 1, and its pharmaceutically acceptable salt or stereoisomer thereof, wherein R¹ is selected from the group consisting of the following groups that are unsubstituted or substituted by 1-2 same or different Q¹:

(1) $C_{1-4}$alkyl, cyclopropyl-$C_{0-4}$alkyl, cyclobutyl-$C_{0-4}$alkyl, cyclopentyl-$C_{0-4}$alkyl, cyclohexyl-$C_{0-4}$alkyl and cycloheptyl-$C_{0-4}$alkyl, the carbon atom in said cyclopropyl, said cyclobutyl, said cyclopentyl, said cyclohexyl and said cycloheptyl may be optionally replaced by 1-2 same or different groups consisting of O, S(O)$_m$, N(H)$_n$ and/or C(O); and (2)

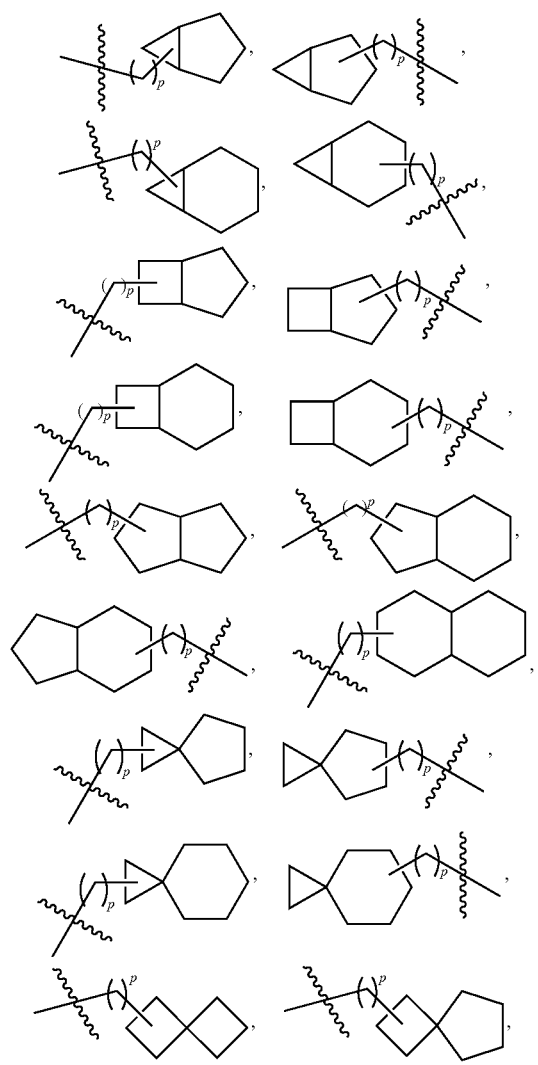

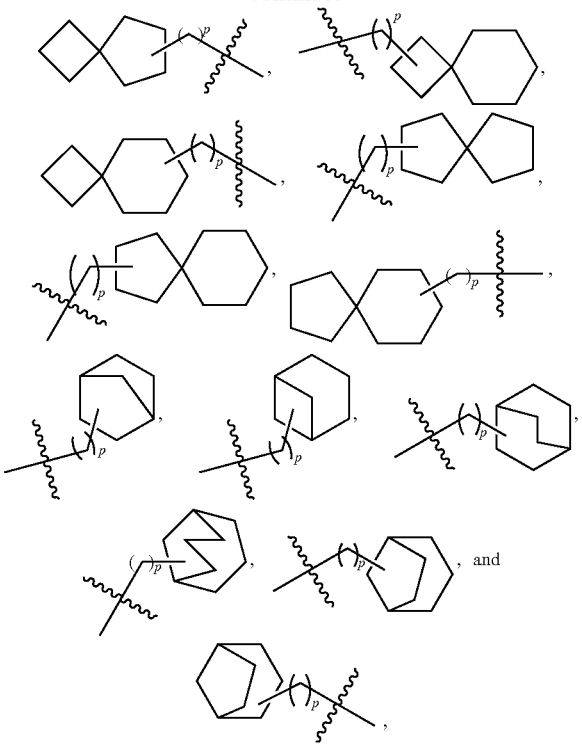

the carbon atom in said ring may be optionally replaced by 1-2 same or different groups consisting of O, S(O)$_m$, N(H)$_n$ and/or C(O), wherein p is selected from the group consisting of 0, 1 or 2; and Q¹ is selected from the group consisting of halogen, hydroxy, amino, carboxyl, cyano, methyl, ethyl, methoxy, ethoxy, methylamino, ethylamino, dimethylamino, diethylamino, acetoxy, acetylamino, methyl sulfonyl, ethyl sulfonyl, methylsulfinyl, methylsulfonylamino, ethylsulfonylamino, cyclopropyl, cyclobutyl, cyclopentyl and cyclohexyl;

R² is selected from the group consisting of (1) the following groups that are unsubstituted or substituted by 1-2 same or different Q²:

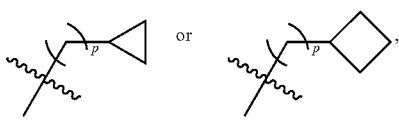

the carbon atom in said ring may be replaced by 1-2 same or different groups consisting of O, S(O)$_m$, N(H)$_n$ and/or C(O), provided that an ester structure "—O—C(O)—" is not present in the replaced ring; p is selected from the group consisting of 0, 1 or 2; and (2)

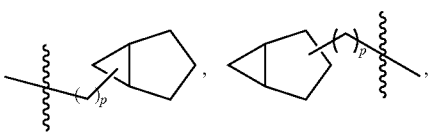

-continued

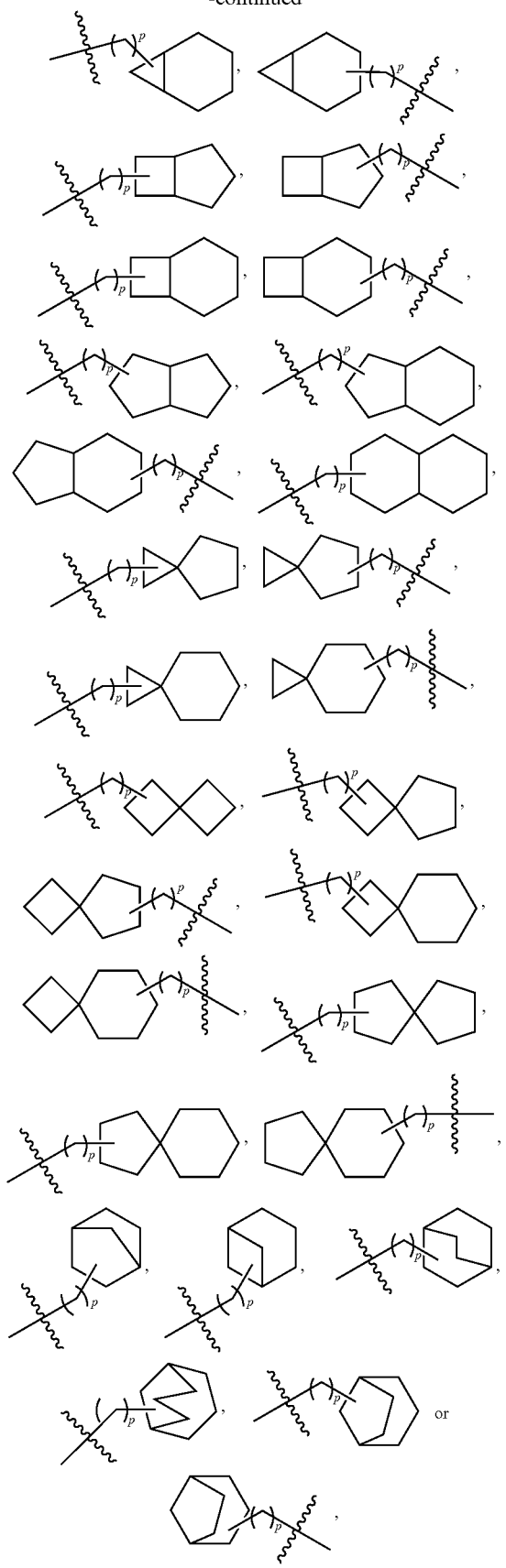

the carbon atom in said ring may be optionally replaced by 1-2 same or different groups consisting of O, $S(O)_m$, $N(H)_n$ and/or C(O), provided that an ester structure "—O—C(O)—" is not present in the replaced ring, wherein p is selected from the group consisting of 0, 1 or 2, and when $R^2$ is

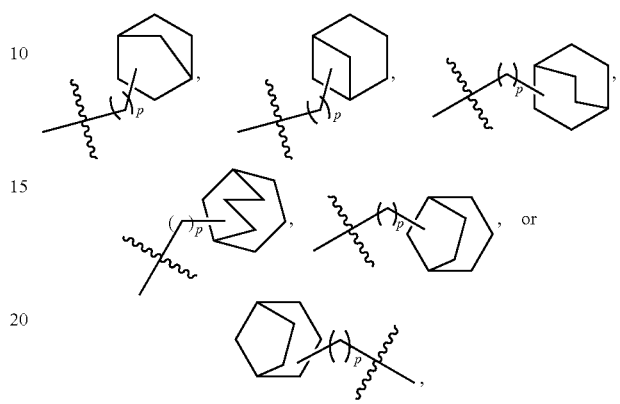

$R^1$ is not $C_{1-4}$alkyl, cyclopropyl-$C_{0-4}$alkyl or cyclobutyl-$C_{0-4}$ alkyl;

and $Q^2$ is selected from the group consisting of halogen, hydroxy, amino, methyl, ethyl, methoxy, ethoxy, methylamino, ethylamino, dimethylamino, diethylamino, acetoxy, acetylamino, methyl sulfonyl and methylsulfonylamino;

$R^3$ is selected from the group consisting of halogen, hydroxy, cyano, nitro, trifluoromethyl, carbamoyl, methyl, ethyl, ethenyl, ethynyl, methoxy, methyl substituted with halogen, methoxy substituted with halogen, methylamino, ethylamino, dimethylamino, methylthio, methylcarbamoyl, acetyl, methoxycarbonyl, acetoxy, acetylamino and methylsulfonylamino;

$R^4$, $R^5$ and $R^6$ are each independently selected from the group consisting of hydrogen, halogen, methyl, methoxy, methyl substituted with halogen, methoxy substituted with halogen, methylamino or dimethylamino;

X is selected from the group consisting of cyano-substituted methenyl or a nitrogen atom;

L is O;

T is selected from the group consisting of a covalent bond or CH(R'), R' is selected from the group consisting of hydrogen or methyl;

Z is hydrogen;

q is 2, and $R^3$ may be identical or different;

m is selected from the group consisting of 0, 1 or 2; and n is selected from the group consisting of 0 or 1.

4. The compound of claim 3, and its pharmaceutically acceptable salt or stereoisomer thereof, wherein $R^1$ is selected from the group consisting of the following groups that are unsubstituted or substituted by $Q^1$:

(1) methyl, ethyl, propyl, cyclopropyl-$C_{0-3}$alkyl, cyclobutyl-$C_{0-3}$alkyl, cyclopentyl-$C_{0-3}$alkyl, cyclohexyl-$C_{0-3}$alkyl, azetidinyl-$C_{0-3}$alkyl, tetrahydrofuryl-$C_{0-3}$alkyl, pyrrolidinyl-$C_{0-3}$alkyl, piperidinyl-$C_{0-3}$alkyl, morpholinyl-$C_{0-3}$ alkyl and piperazinyl-$C_{0-3}$alkyl; and (2)

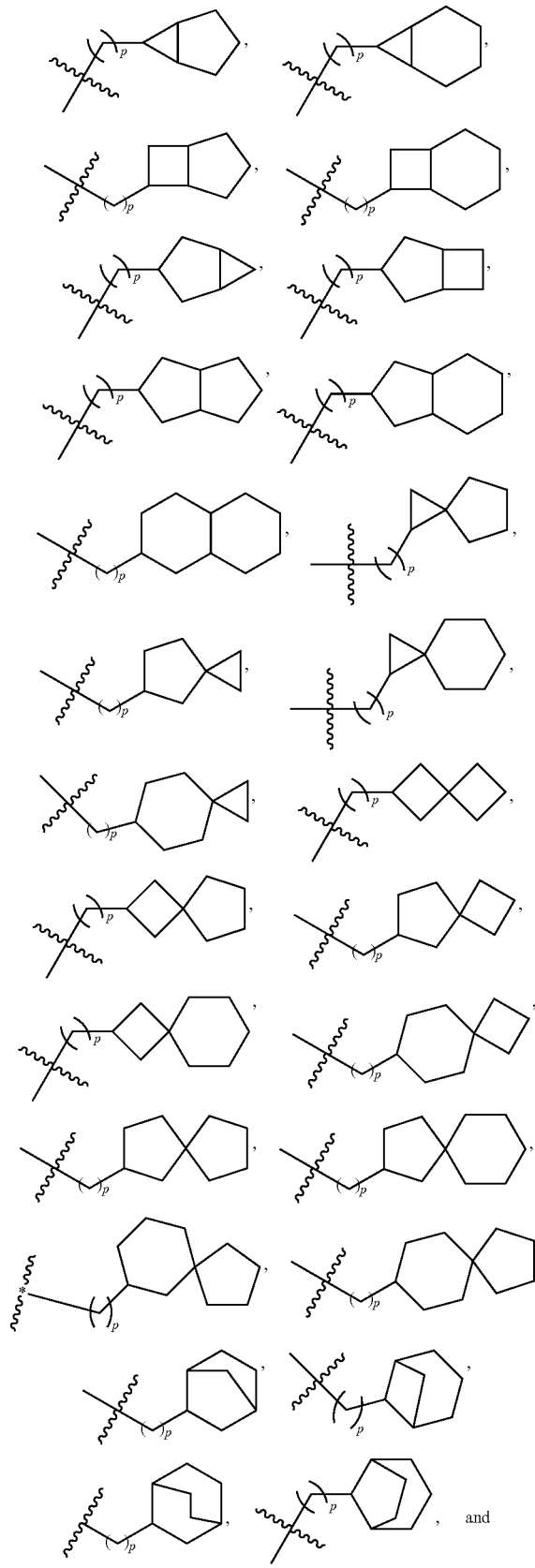

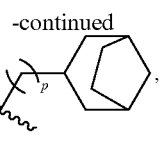

the carbon atom in said ring may be optionally replaced by 1-2 same or different groups consisting of O, $S(O)_m$, $N(H)_n$ and/or C(O), wherein p is selected from the group consisting of 0, 1 or 2;

and $Q^1$ is selected from the group consisting of halogen, hydroxy, amino, carboxyl, cyano, methyl, ethyl, methoxy, ethoxy, methylamino, ethylamino, dimethylamino, or diethylamino;

$R^2$ is selected from the group consisting of (1)

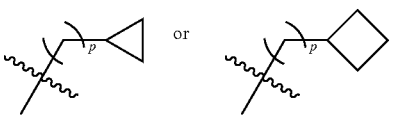

that is unsubstituted or substituted by $Q^2$, the carbon atom in said ring may be replaced by 1-2 same or different groups consisting of O, $S(O)_m$, $N(H)_n$ and/or C(O), provided that an ester structure "—O—C(O)—" is not present in the replaced ring; wherein p is selected from the group consisting of 0, 1 or 2; and (2)

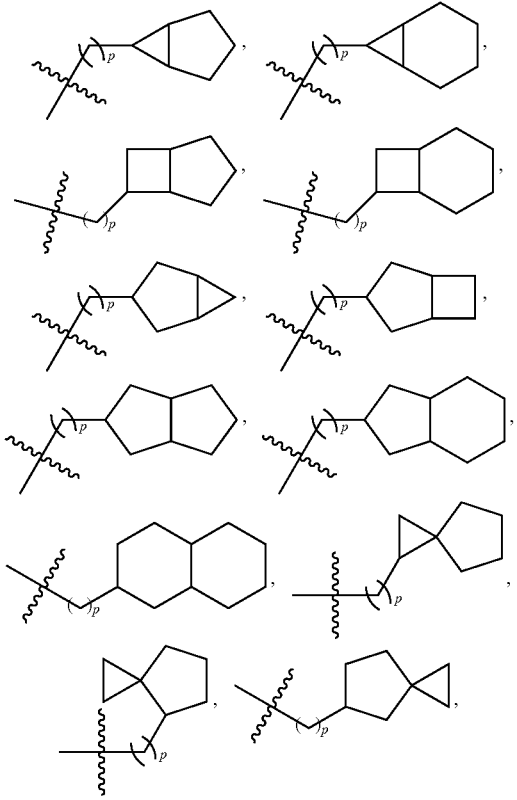

-continued

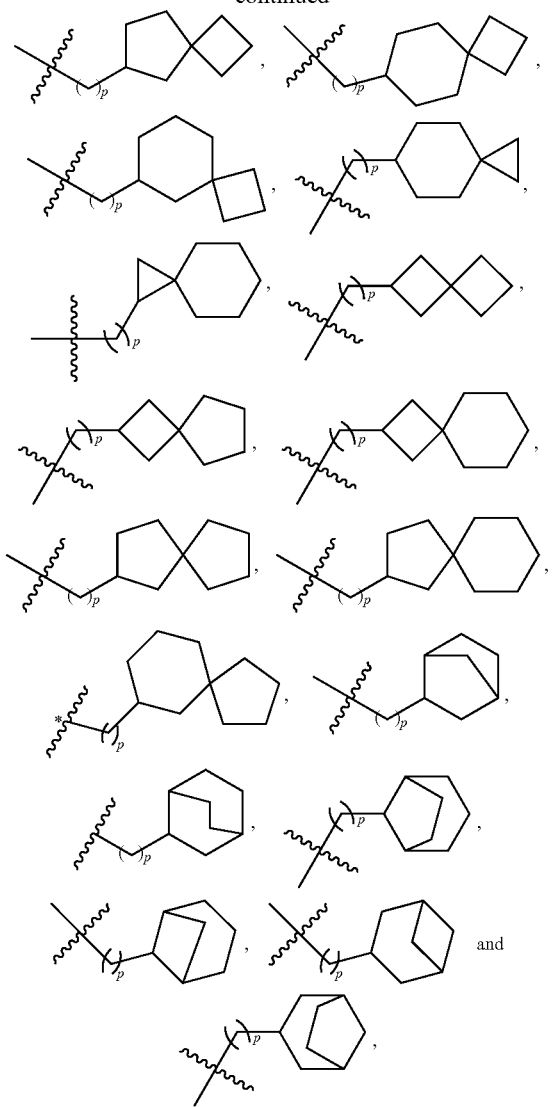

the carbon atom in said ring may be optionally replaced by 1-2 same or different groups consisting of O, S(O)$_m$, N(H)$_n$ and/or C(O), provided that an ester structure "—O—C(O)—" is not present in the replaced ring, wherein p is selected from the group consisting of 0, 1 or 2; and when R$^2$ is

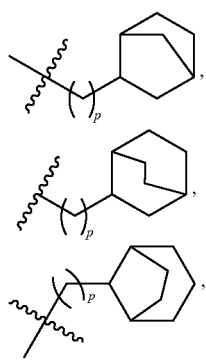

-continued

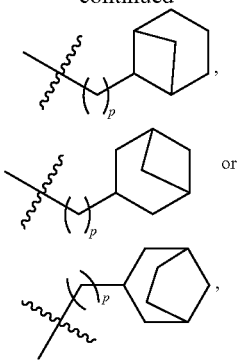

R$^1$ is not methyl, ethyl, propyl, cyclopropyl-C$_{0-3}$alkyl or cyclobutyl-C$_{0-3}$alkyl;
and Q$^2$ is selected from the group consisting of halogen, hydroxy, amino, methyl, ethyl, methoxy, ethoxy, methylamino, ethylamino, dimethylamino, diethylamino, acetoxy, acetylamino, methyl sulfonyl and methylsulfonylamino;

R$^3$ is selected from the group consisting of halogen, hydroxy, cyano, nitro, trifluoromethyl, carbamoyl, methyl, ethyl, ethenyl, ethynyl, methoxy, methyl substituted with halogen, methoxy substituted with halogen, methylamino, ethylamino, dimethylamino, methylthio, methylcarbamoyl, acetyl, methoxycarbonyl, acetoxy, acetylamino and methylsulfonylamino;

R$^4$, R$^5$ and R$^6$ are each independently selected from the group consisting of hydrogen, halogen, methyl, methoxy, methyl substituted with halogen, methoxy substituted with halogen, methylamino and dimethylamino;

X is a nitrogen atom;

L is O;

T is selected from the group consisting of a covalent bond or CH(R'), R' is hydrogen;

Z is hydrogen;

q is 2, and R$^3$ may be identical or different;

m is selected from the group consisting of 0, 1 or 2; and n is selected from the group consisting of 0 or 1.

5. The compound of claim 1, and its pharmaceutically acceptable salt or stereoisomer thereof, said compound has a structure of the following formula (I-1):

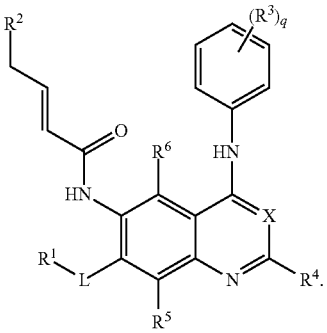

(I-1)

6. The compound of claim 5, and its pharmaceutically acceptable salt or stereoisomer thereof, wherein:

R$^1$ is selected from the group consisting of the following groups that are unsubstituted or substituted by halogen, hydroxy, amino, carboxyl, cyano, methyl, ethyl, methoxy, ethoxy, methylamino, ethylamino, dimethylamino, or diethylamino: methyl, ethyl,

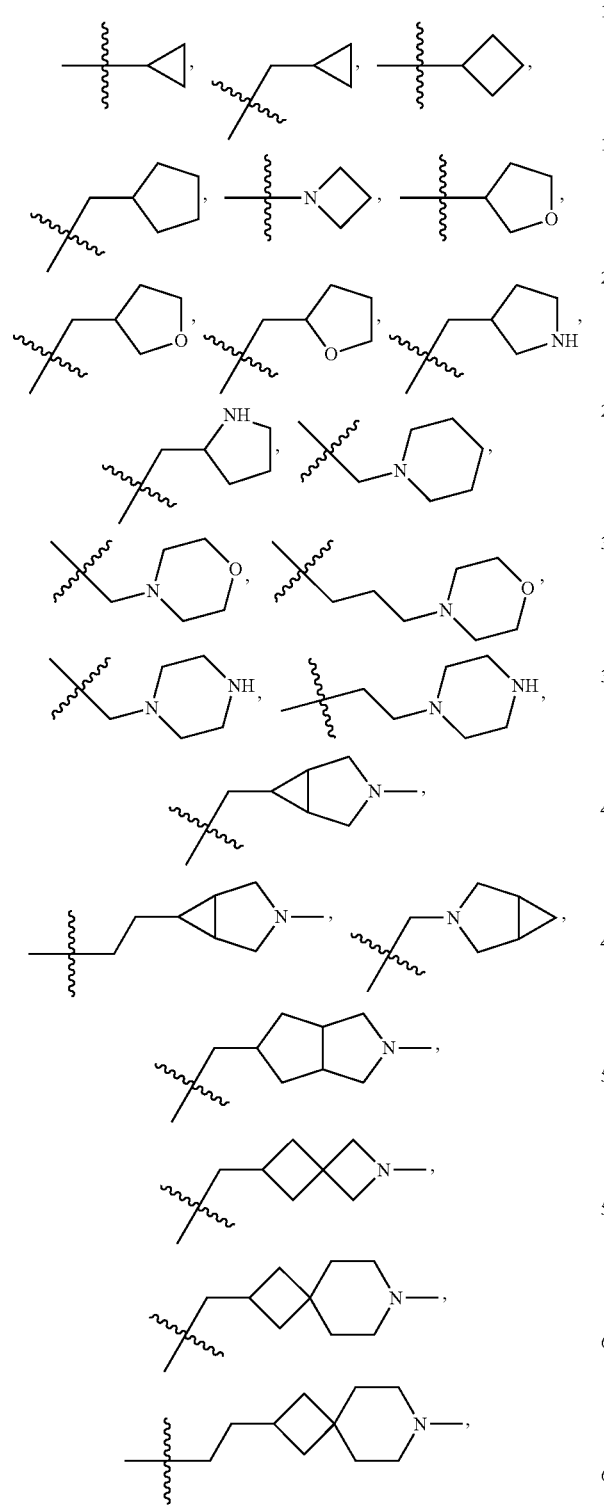

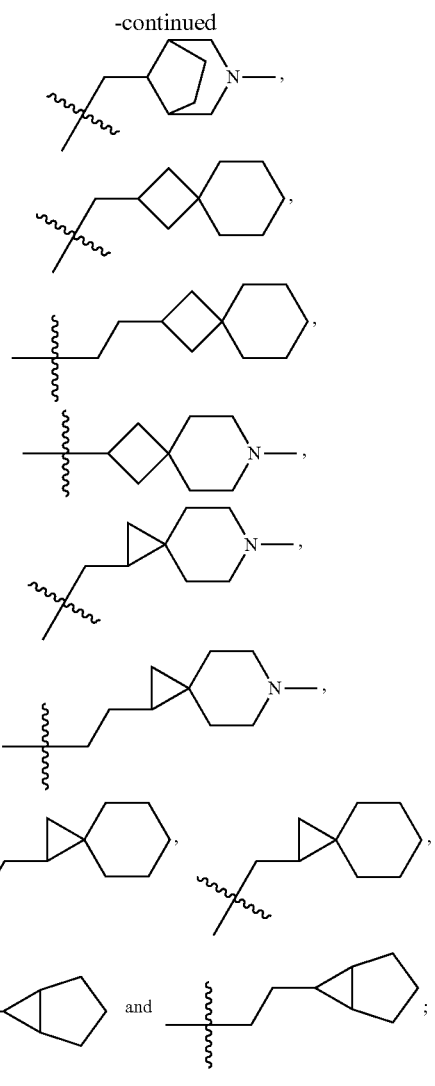

R$^2$ is selected from the group consisting of the following groups that are unsubstituted or substituted by halogen, hydroxy, amino, methyl, ethyl, methoxy, ethoxy, methylamino, ethylamino, dimethylamino, diethylamino, acetoxy, acetylamino, methylsulfonyl, or methylsulfonylamino:

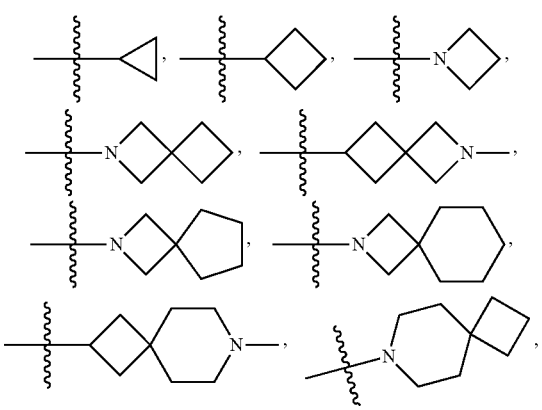

-continued
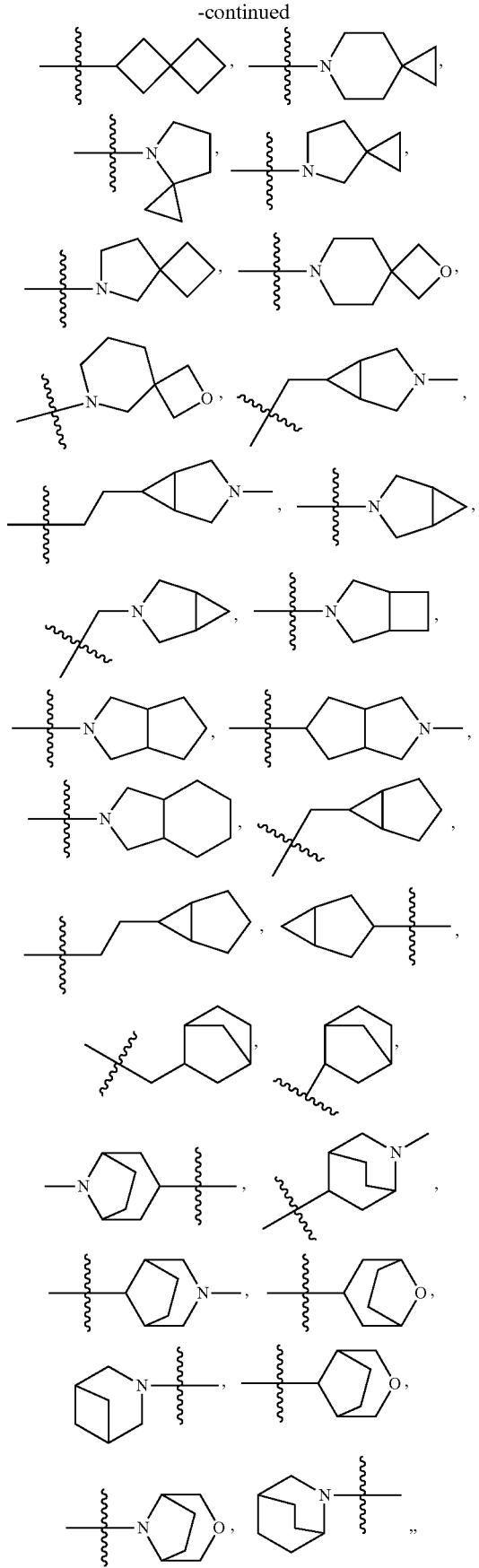
-continued
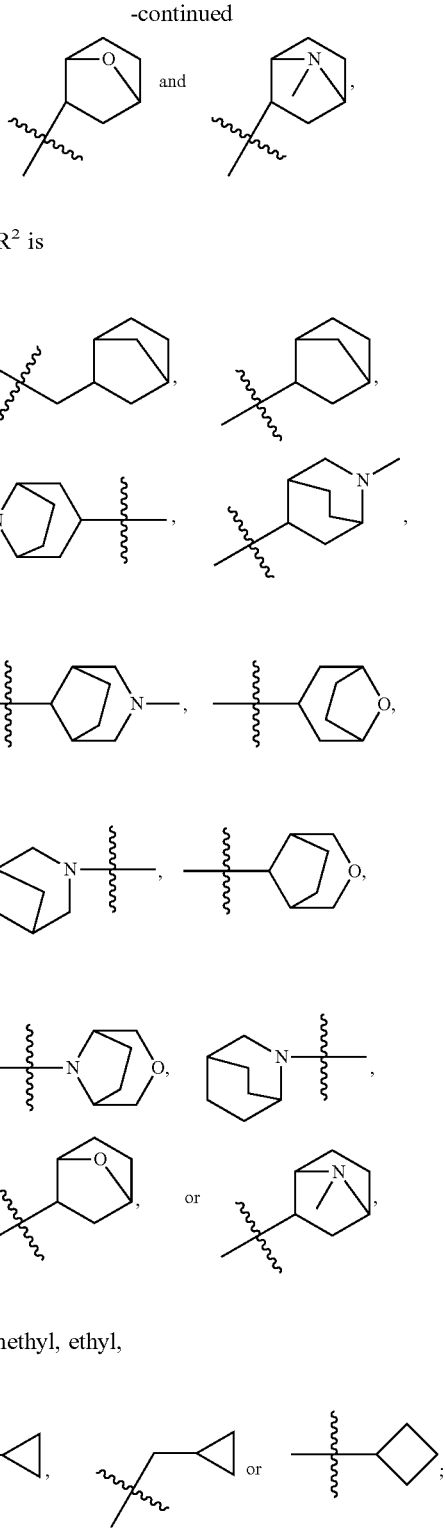
and when $R^2$ is
$R^1$ is not methyl, ethyl,
$R^3$ is halogen, which is selected from the group consisting of fluoro, chloro, bromo, or iodo;
$R^4$, $R^5$ and $R^6$ are each independently hydrogen;
X is a nitrogen atom;
L is O; and
q is 2, and $R^3$ may be identical or different.

7. The compound of claim 6, and its pharmaceutically acceptable salt or stereoisomer thereof, said compound has a structure of the following formula (I-2):

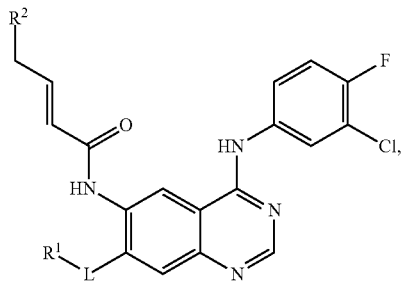

wherein
R¹ is selected from the group consisting of the following groups that are unsubstituted or substituted by halogen, hydroxy, amino, carboxyl, cyano, methyl, ethyl, methoxy, ethoxy, methylamino, ethylamino, dimethylamino, or diethylamino: methyl, ethyl,

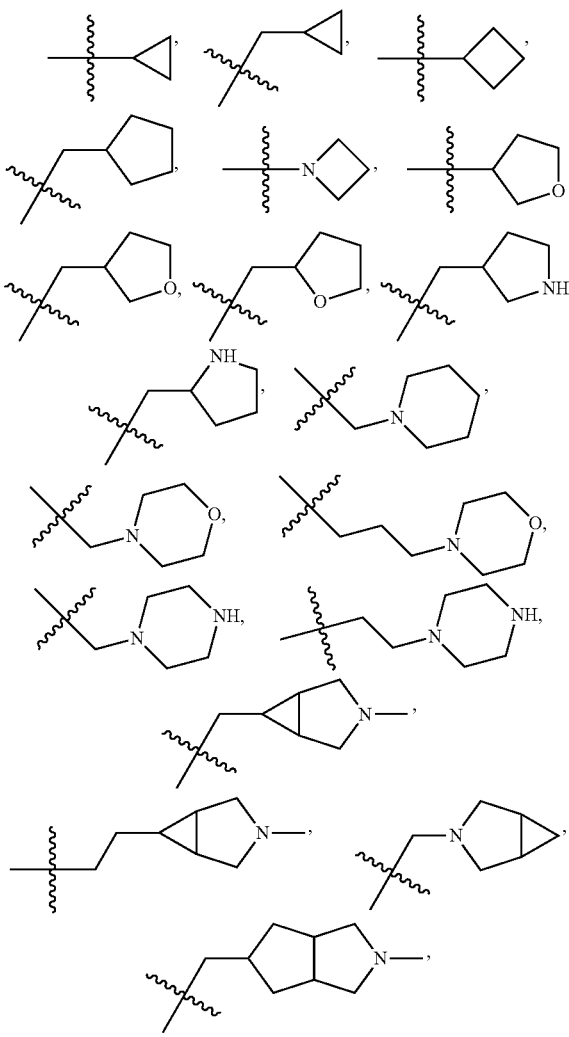

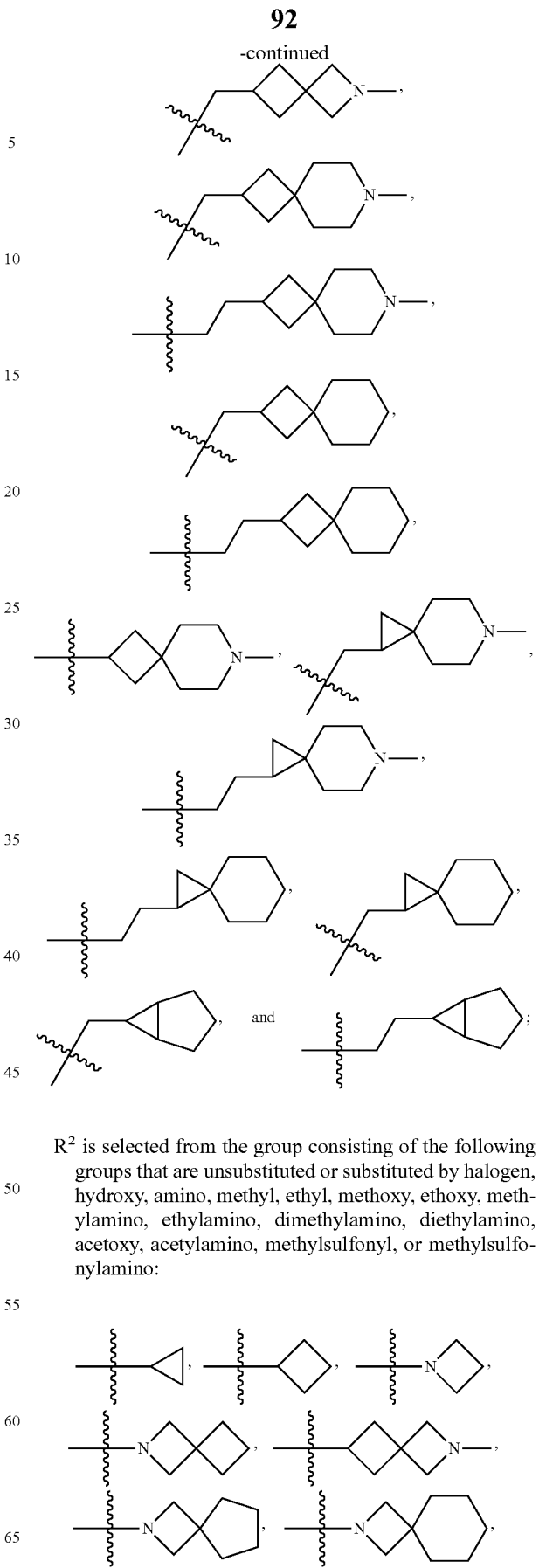

R² is selected from the group consisting of the following groups that are unsubstituted or substituted by halogen, hydroxy, amino, methyl, ethyl, methoxy, ethoxy, methylamino, ethylamino, dimethylamino, diethylamino, acetoxy, acetylamino, methylsulfonyl, or methylsulfonylamino:

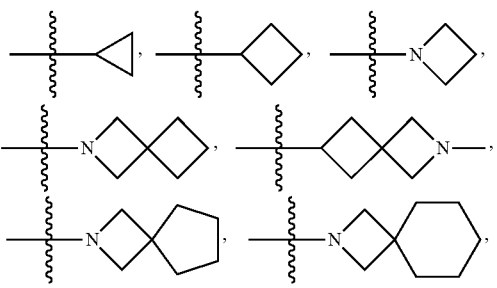

-continued and when R² is

R¹ is not methyl, ethyl, and
L is O.

8. The compound of claim 1, and its pharmaceutically acceptable salt or stereoisomer thereof, wherein said compound is selected from the group consisting of:
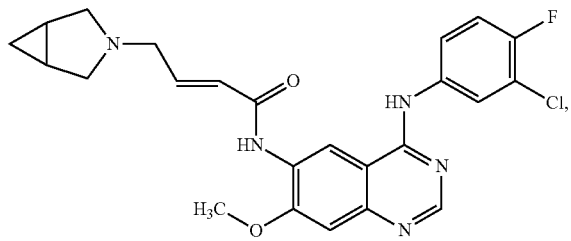
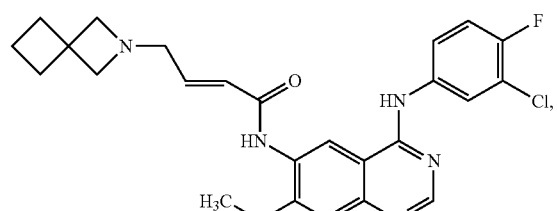
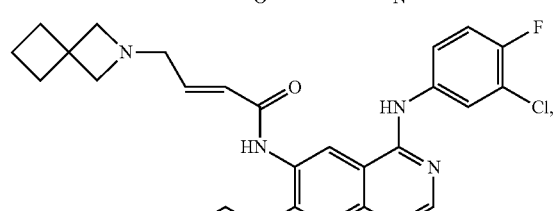
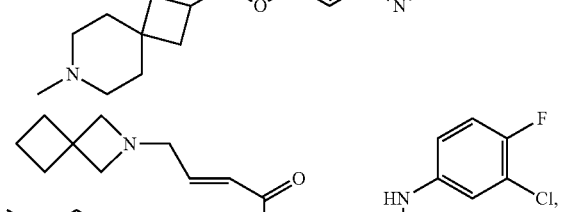
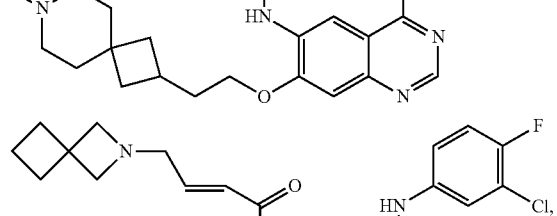
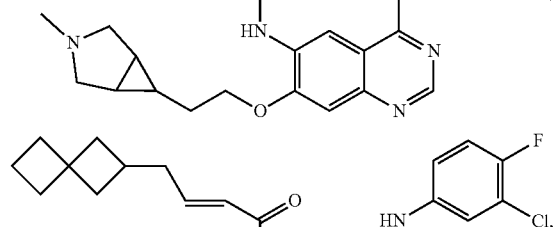
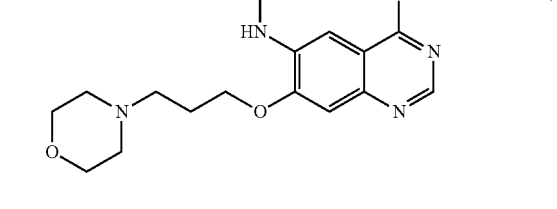
-continued
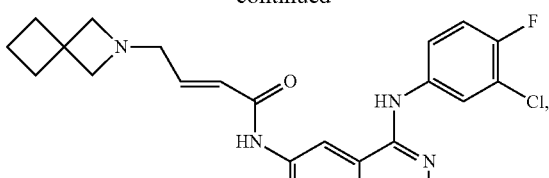
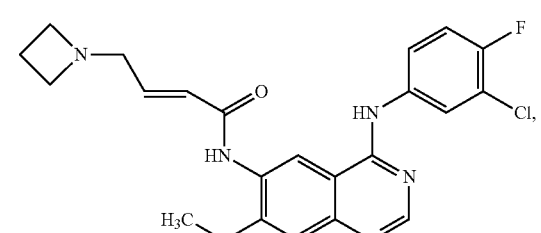
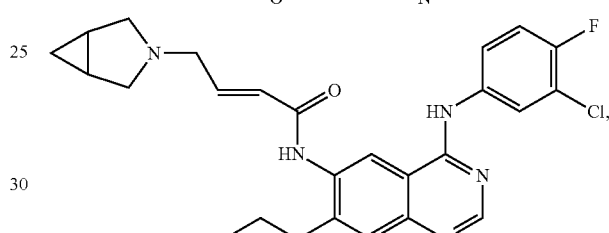
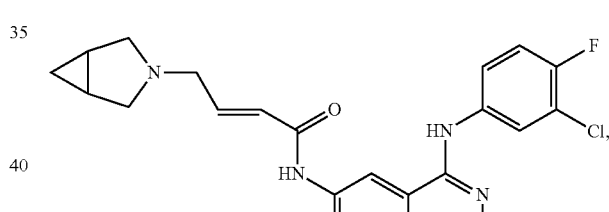
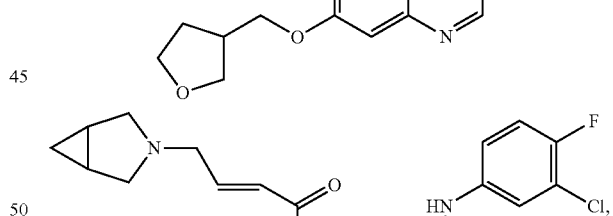
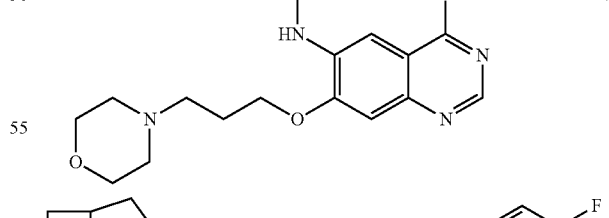
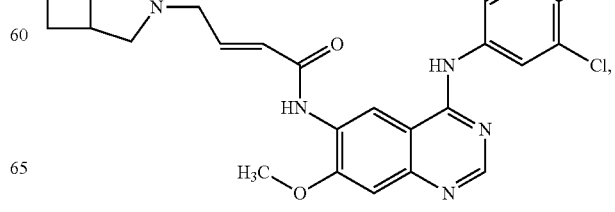

97
-continued
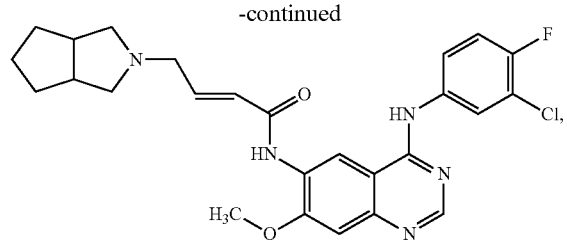
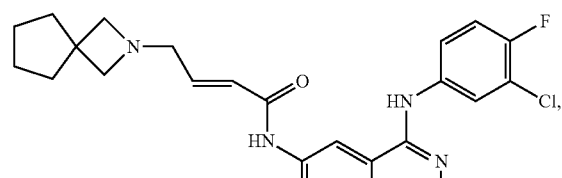
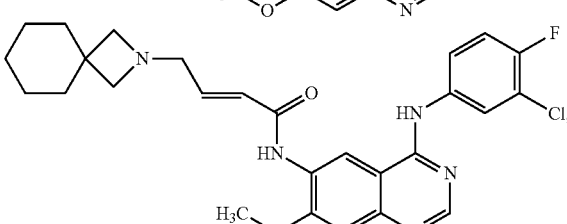
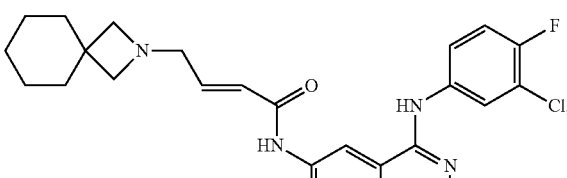
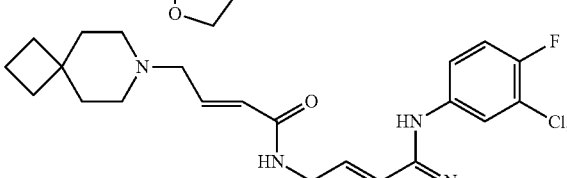
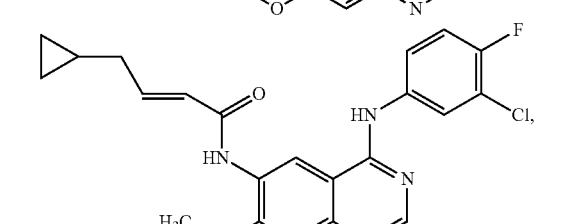
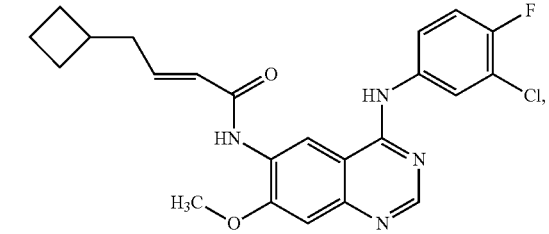
98
-continued
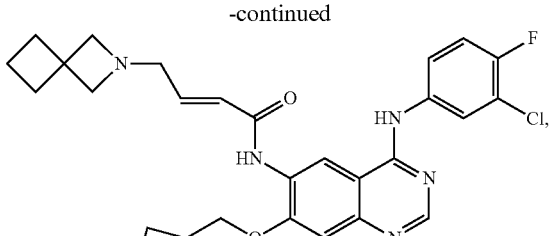
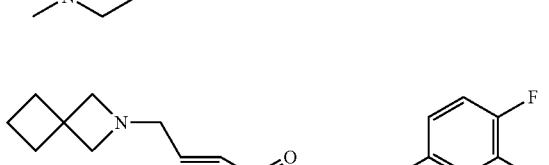
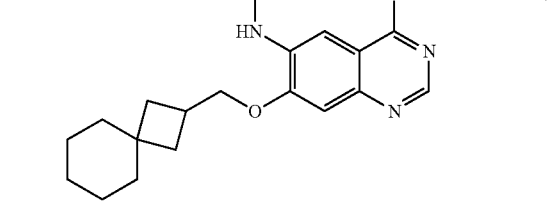
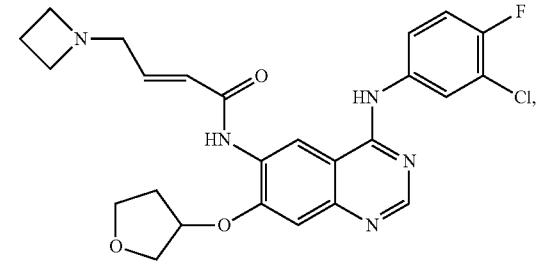
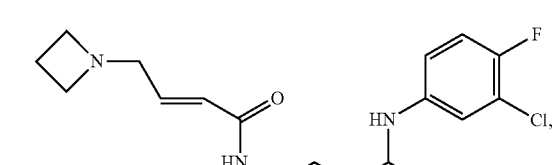
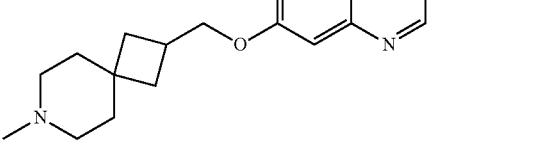
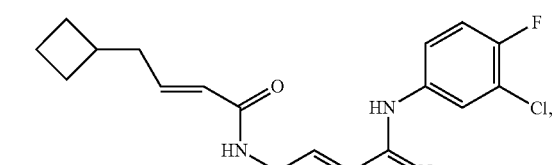
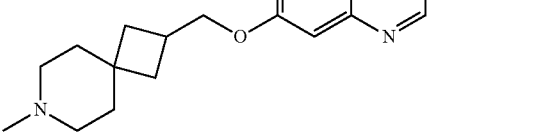

-continued

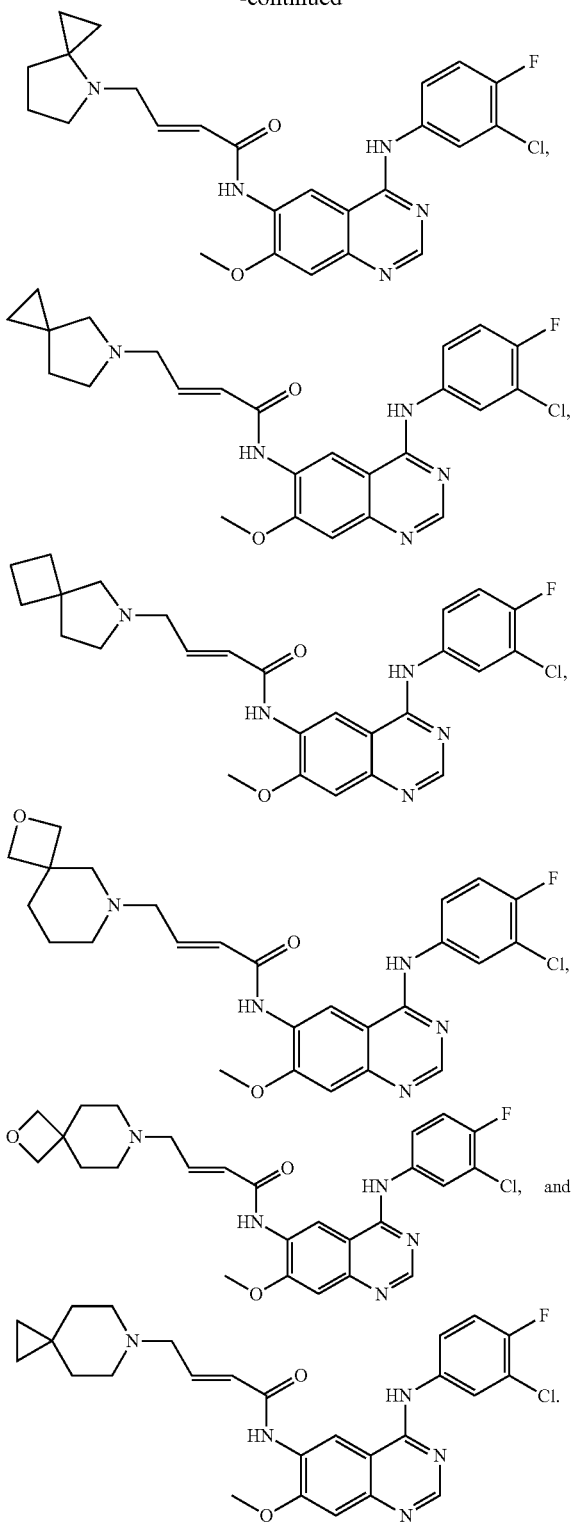

9. A pharmaceutical composition, which contains a compound of claim 1, a pharmaceutically acceptable salt thereof or a stereoisomer thereof.

10. A pharmaceutical composition of claim 9, which further contains a second therapeutical agent selected from the group consisting of an antineoplastic agent and an immunosuppressive agent, said second therapeutical agent is selected from the group consisting of an antimetabolite, including capecitabine and gemcitabine; a growth factor inhibitor, including pazopanib and imatinib; an antibody, including herceptin and bevacizumab; a mitotic inhibitor, including paclitaxel, vinorelbine, docetaxel, and doxorubicin; an antineoplastic hormone, including letrozole, tamoxifen, and fulvestrant; an alkylating agent, including cyclophosphamide and carmustine; a metal platinum, including carboplatin, cisplatin, and oxaliplatin; a topoisomerase inhibitor, including topotecan; and an immunosuppressant, including everolimus.

11. A pharmaceutical formulation containing a compound of claim 1, a pharmaceutically acceptable salt thereof or a stereoisomer thereof and one or more pharmaceutically acceptable carriers.

12. A process for preparing a compound of claim 1, comprising the following steps 1), 2), 3), and 4) in sequential order according to the following reaction procedure:

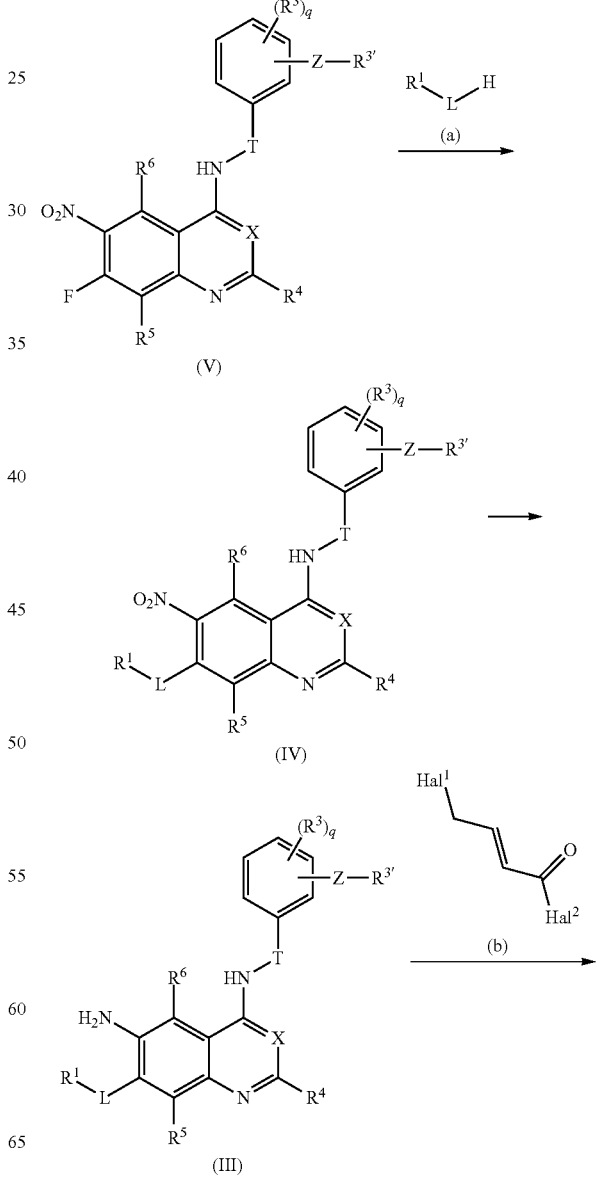

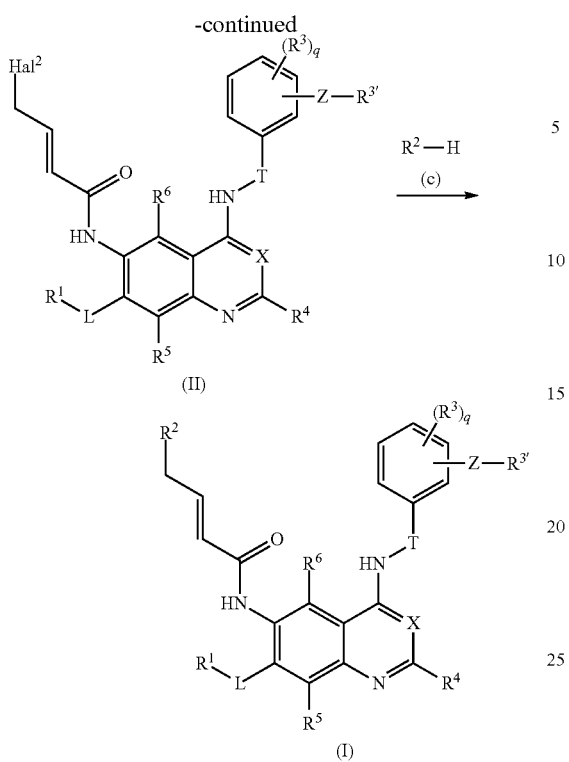

wherein $R^1$, $R^2$, $R^3$, $R^{3'}$, $R^4$, $R^5$, $R^6$, X, L, T, Z and q are as defined in claim 1, $Hal^1$ is selected from the group consisting of Cl, Br and I, $Hal^2$ is selected from the group consisting of Cl and Br, and $Hal^1$ and $Hal^2$ may be identical or different;

1) Dissolving a compound of the starting material (a) in an organic solvent, and reacting it with a compound of the formula (V) in the presence of an inorganic base to produce a compound of the formula (IV);

2) Reacting the compound of the formula (IV) and a reducing agent to produce a compound of the formula (III);

3) Dissolving the compound of the formula (III) in an organic solvent, and reacting it with a compound of the formula (b) to produce a compound of the formula (II); and 4) Reacting the compound of the formula (II) and a compound of the formula (c) in the presence of a base to produce a compound of the formula (I).

* * * * *